United States Patent
Wagner et al.

(10) Patent No.: US 7,662,958 B2
(45) Date of Patent: Feb. 16, 2010

(54) ANTI-INFECTIVE AGENTS

(76) Inventors: Rolf Wagner, 42530 Sheridan Oaks Dr., Antioch, IL (US) 60002; Pamela L. Donner, 1901 McRae La., Mundelein, IL (US) 60060; Dale J. Kempf, 256 Tyler Ct., Libertyville, IL (US) 60048; Clarence J. Maring, 1228 W. Borders, Palatine, IL (US) 60067; Vincent S. Stoll, 218 E. Winchester Rd., Libertyville, IL (US) 60048; Yi-Yin Ku, 23 River Oaks Cir. E., Buffalo Grove, IL (US) 60089; Yu-Ming Pu, 5507 Notting Hill Rd., Gurnee, IL (US) 60031

( * ) Notice: Subject to any disclaimer, the term of this patent is extended or adjusted under 35 U.S.C. 154(b) by 0 days.

(21) Appl. No.: 11/777,692

(22) Filed: Jul. 13, 2007

(65) Prior Publication Data
US 2008/0214528 A1  Sep. 4, 2008

Related U.S. Application Data

(60) Provisional application No. 60/831,853, filed on Jul. 19, 2006.

(51) Int. Cl.
  C07D 498/02 (2006.01)
  C07D 417/04 (2006.01)
  A61K 31/549 (2006.01)
(52) U.S. Cl. ..................... 544/10; 514/222.8
(58) Field of Classification Search ............... 544/10; 514/222.8
See application file for complete search history.

(56) References Cited

U.S. PATENT DOCUMENTS

| | | | |
|---|---|---|---|
| 6,348,587 B1 | 2/2002 | Schinazi et al. | 536/25.3 |
| 2004/0087577 A1 | 5/2004 | Pratt et al. | 514/222.8 |
| 2004/0097492 A1 | 5/2004 | Pratt et al. | 514/222.8 |
| 2004/0162285 A1 | 8/2004 | Pratt et al. | 514/222.3 |
| 2004/0167123 A1 | 8/2004 | Pratt et al. | 424/623 |
| 2005/0075331 A1 | 4/2005 | Pratt et al. | 514/223.2 |
| 2008/0193413 A1 | 8/2008 | Hutchinson et al. | 424/85.5 |

FOREIGN PATENT DOCUMENTS

| | | |
|---|---|---|
| EP | 01162196 A1 | 12/2001 |
| WO | WO0132153 A2 | 5/2001 |
| WO | WO0132153 A3 | 5/2001 |
| WO | WO0160315 A2 | 8/2001 |
| WO | WO0160315 A3 | 8/2001 |
| WO | WO0190121 A2 | 11/2001 |
| WO | WO0190121 A3 | 11/2001 |
| WO | WO0204425 A2 | 1/2002 |
| WO | WO0204425 A3 | 1/2002 |
| WO | WO03059356 A2 | 7/2003 |
| WO | WO03059356 A3 | 7/2003 |
| WO | WO2004041818 A1 | 5/2004 |
| WO | WO200519191 A2 | 3/2005 |
| WO | WO200519191 A3 | 3/2005 |
| WO | WO2008011337 A1 | 1/2008 |

OTHER PUBLICATIONS

M. Barbero et al, Synthetic Application of Tris(methylthio)methyl Salts. An Efficient Route to Trithioorthocarboxylic Esters from Strongly Activated Aromatic and Heteroaromatic Systems, Synthesis pp. 22-25 (Jan. 1988).
K.J. Blight et al., Efficient Initiation of HCV RNA Replication in Cell Culture, Science 290:1972-4 (2000).
M. Ikeda et al., Selectable Subgenomic and Genome-Length Dicistronic RNAs Derived from an Infectious Molecular Clone of the HCV-N Strain of Hepatitis C Virus Replicate Efficiently in cultured Huh7 Cells, J. Virol. 76(6):2997-3006 (2002).
A.C. Krueger et al., Inhibitors of HCV NS5B Polymerase: Synthesis and Structure-activity Relationships of N-alyl-4-hydroxyquinolon-3-yl-benzothiadiazine Sulfamides, Bioorg. & Med. Chem. Let. 16(13): 3367-70 (2006).
J.K. Pratt et al., Inhibitors of HCV NS5B Polymerase: Synthesis and Structure-activity Relationships of N-1-heteroalkyl-4-hydroxyquinolon-3-yl-benzothiadiazine, Bioorg. & Med. Chem. Let. 15(6): 1577-82 (2005).
P. Stanetty et al., An Improved Synthetic Approach to Thieno[2,3-d]-1,2,3-thiadiazole-carboxylates via Diazotization of Aminothiophene Derivatives, J. Het. Chem 36:761-5(1999).

Primary Examiner—Kahsay T Habte
(74) Attorney, Agent, or Firm—Lydia N. Nenow

(57) ABSTRACT

The present invention provides HCV polymerase inhibiting compounds having the formula (I):

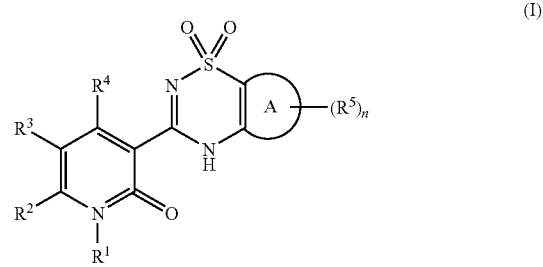

where $R^1$ is cyclobutyl-N($R_a$)—, n is 1, 2, 3 or 4, and at least one $R^5$ is $R_a SO_2 N(R_j)$alkyl-. In a non-limiting example, a compound of the present invention is N-[(3-{1-[(cyclobutyl)amino])-4-hydroxy -2-oxo-1,2-dihydro-quinolin-3-yl}-1,1-dioxo-1,4-dihydro-1$\lambda^6$-thieno[2,3-e][1,2,4]thiadiazin-7-yl)methyl]methane-sulfonamide. The present invention also features compositions comprising the compounds of the present invention or pharmaceutically acceptable salts, stereoisomers or tautomers thereof, and methods of using the same to treat or prevent HCV infection.

2 Claims, 1 Drawing Sheet

ANTI-INFECTIVE AGENTS

CROSS-REFERENCE TO RELATED PATENT APPLICATIONS

This patent application claims priority to U.S. Provisional Patent Application No. 60/831,853 (filed Jul. 19, 2006). The entire text of that application is incorporated by reference into this application.

TECHNICAL FIELD

The present invention features hepatitis C virus (HCV) polymerase inhibiting compounds and compositions comprising the same. The present invention also features methods of using these compounds to inhibit HCV polymerase and HCV viral replication. In addition, the present invention feature methods of using these compounds to treat or prevent HCV infection. Processes for making these compounds, and synthetic intermediates employed in said processes, are also provided.

BACKGROUND OF THE INVENTION

Infection with hepatitis C virus (HCV) is a major cause of human liver disease throughout the world. More than 85% of all infected individuals become chronically infected. Chronic HCV infection accounts for 30% of all cirrhosis, end-stage liver disease, and liver cancer in the United States. The CDC estimates that the number of deaths due to HCV will increase to 38,000 per year by the year 2010.

While initially therapy consisted of interferon alone, the combination of interferon alpha-2b with ribavirin for either 24 or 48 weeks is currently the most efficacious approved therapy for the treatment of chronic HCV infection. However, there are many adverse side effects associated with this therapy (flu-like symptoms, leukopenia, thrombocytopenia, and depression from interferon, as well as anemia induced by ribavirin). Furthermore, this therapy is less effective against infections caused by HCV genotype 1 which constitutes about 75% of all HCV infections.

Based on the foregoing, there exists a significant need to identify new compounds with the ability to inhibit HCV. The present invention provides novel anti-infective agents capable of inhibiting HCV polymerase.

SUMMARY OF THE INVENTION

The present invention features compounds of formula (I)

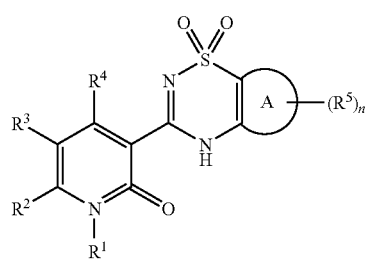

(I)

or pharmaceutically acceptable salt forms, stereoisomers or tautomers thereof, wherein:
A is a monocyclic or bicyclic ring selected from the group consisting of aryl, cycloalkyl, cycloalkenyl, heteroaryl and heterocycle;

$R^1$ is cyclobutyl-N($R_a$)—, and is optionally substituted with at least 1, 2 or 3 substituents each of which is independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alky)(NR$_c$R$_c$), —SR$_c$, —S(O)R$_c$, —S(O)$_2$R$_c$, —OR$_c$, —N(R$_c$)(R$_c$), —C(O)R$_c$, —C(O)OR$_c$ and —C(O)NR$_c$R$_c$;

$R^2$ and $R^3$ are each independently selected from the group consisting of hydrogen, alkenyl, alkynyl, alkoxyalkyl, alkoxycarbonyl, alkyl, aryl, arylalkyl, heteroaryl, heterocycle, heteroarylalkyl, cyano, halo, —N(R$_a$)(R$_b$), R$_a$R$_b$NC(O)—, —SR$_a$, —S(O)R$_a$, —S(O)$_2$R$_a$ and R$_a$C(O)—, wherein $R^2$ and $R^3$ are each independently optionally substituted with at least 1, 2 or 3 substituents each of which is independently selected from the group consisting of R$_a$, alkyl, alkenyl, alkynyl, oxo, halo, cyano, nitro, haloalkyl, -(alkyl)(OR$_k$), -(alkyl)(NR$_a$R$_b$), —SR$_a$, —S(O)R$_a$, —S(O)$_2$R$_a$, —OR$_k$, —N(R$_a$)(R$_b$), —C(O)R$_a$, —C(O)OR$_a$ and —C(O)NR$_a$R$_b$;
alternatively, $R^2$ and $R^3$, together with the carbon atoms to which they are attached, form a five- or six-membered ring selected from the group consisting of aryl, cycloalkyl, heteroaryl and heterocycle, wherein each said aryl, cycloalkyl, heteroaryl and heterocycle is optionally substituted with $(R^6)_m$;

$R^4$ is selected from the group consisting of alkoxy, aiylalkoxy, aryloxy, halo, hydroxy, R$_a$R$_b$N—, N$_3$— and R$_e$S—, and is optionally substituted with at least 1 or 2 substituents each of which is independently selected from the group consisting of halo, nitro, cyano, —OH, —NH$_2$, and —COOH;

$R^5$ is independently selected at each occurrence from the group consisting of alkenyl, alkoxy, alkyl, alkynyl, aryl, arylalkyl, arylcarbonyl, aryloxy, azidoalkyl, formyl, halo, haloalkyl, halocarbonyl, heteroaryl, heteroarylalkyl, heterocycle, heterocyclealkyl, hydoxyalkyl, cycloalkyl, cyano, cyanoalkyl, nitro, R$_a$R$_b$N—, R$_a$C(O)—, R$_a$S—, R$_a$(O)S—, R$_a$(O)$_2$S—, R$_a$R$_b$Nalkyl-, R$_a$(O)SN(R$_f$)—, R$_a$SO$_2$N(R$_f$)—, R$_a$(O)SN(R$_f$)alkyl-, R$_a$SO$_2$N(R$_f$)alkyl-, R$_a$R$_b$NSO$_2$N(R$_f$)—, R$_a$R$_b$NSO$_2$N(R$_f$)alkyl-, R$_a$R$_b$NC(O)—, R$_k$OC(O)—, R$_k$OC(O)alkyl-, R$_k$Oalkyl-, R$_a$R$_b$NSO$_2$—, R$_a$R$_b$NSO$_2$alkyl-, (R$_b$O)(R$_a$)P(O)O— and —OR$_k$, wherein each $R^5$ is independently optionally substituted at each occurrence with at least 1, 2 or 3 substituents each of which is independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

$R^6$ is independently selected at each occurrence from the group consisting of alkyl, alkenyl, alkynyl, halo, cyano, nitro, haloalkyl, haloalkoxy, aryl, heteroaryl, heterocycle, arylalkyl, heteroarylalkyl, heterocyclealkyl, -(alkyl)(OR$_k$), -(alkyl)(NR$_a$R$_b$), —SR$_a$, —S(O)R$_a$, —S(O)$_2$R$_a$, —OR$_k$, —N(R$_a$)(R$_b$), —C(O)R$_a$, —C(O)OR$_a$ and —C(O)NR$_a$R$_b$; wherein each $R^6$ is independently optionally substituted with at least 1, 2 or 3 substituents each of which is independently selected from the group consisting of alkyl, alkenyl, alkynyl, oxo, halo, haloalkyl, cyano, nitro, —OR$_a$, —NR$_a$R$_b$, —SR$_a$, —SOR$_a$, —SO$_2$R$_a$, —C(O)OR$_a$, —C(O)NR$_a$R$_b$ and —NC(O)R$_a$;

$R_a$ and $R_b$ are each independently selected at each occurrence from the group consisting of hydrogen, alkenyl, alkyl, alkylsulfanylalkyl, aryl, arylalkenyl, arylalkyl, cyanoalkyl, cycloalkenyl, cycloalkenylalkyl, cycloalkyl, cycloalkylalkyl, cycloalkylalkenyl, formylalkyl, haloalkyl, heteroaryl, heteroarylalkenyl, heteroarylalkyl, heterocycle, heterocyclealkenyl, heterocyclealkyl, hydroxyalkylcarbonyl, nitroalkyl, $R_cR_dN$—, $R_pO$—, $R_pO$alkyl-, $R_cR_d$Nalkyl-, $R_cR_d$NC(O)alkyl-, $R_cSO_2$—, $R_cSO_2$alkyl-, $R_cC(O)$—, $R_cC(O)$alkyl-, $R_cOC(O)$—, $R_cOC(O)$alkyl-, $R_cR_d$NalkylC(O)—, $R_cR_d$NC(O)—, $R_cR_d$NC(O)Oalkyl-, and $R_cR_d$NC(O)N($R_e$)alkyl-, wherein $R_a$ and $R_b$ are each independently optionally substituted at each occurrence with at least 1 or 2 substituents each of which is independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), —$SR_c$, —$S(O)R_c$, —$S(O)_2R_c$, —$OR_c$, —$N(R_c)(R_d)$, —$C(O)R_c$, —$C(O)OR_c$ and —$C(O)NR_cR_d$;

alternatively, $R_a$ and $R_b$, together with the nitrogen atom to which they are attached, form a three- to six-membered ring selected from the group consisting of heteroaryl and heterocycle, wherein the heteroaryl and heterocycle are each independently optionally substituted at each occurrence with at least 1, 2 or 3 substituents each of which is independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), -alkyl$SO_2NR_cR_d$, -alkylC(O)$NR_cR_d$, —$SR_c$, —$S(O)R_c$, —$S(O)_2R_c$, —$OR_c$, —$N(R_c)(R_d)$, —$C(O)R_c$, —$C(O)OR_c$, and —$C(O)NR_cR_d$;

$R_c$ and $R_d$ are each independently selected at each occurrence from the group consisting of hydrogen, —$NR_fR_h$, —$OR_f$, —$CO(R_f)$, —$SR_f$, —$SOR_f$, —$SO_2R_f$, —$C(O)NR_fR_h$, —$SO_2NR_fR_h$, —$C(O)OR_f$, alkenyl, alkyl, alkynyl, cycloalkyl, cycloalkylalkyl, cycloalkenyl, cycloalkenylalkyl, aryl, arylalkyl, haloalkyl, heteroaryl, heteroarylalkyl, heterocycle and heterocyclealkyl; wherein each $R_c$ and $R_d$ is independently optionally substituted at each occurrence with at least 1, 2, or 3 substituents each of which is independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_f$), -(alkyl)($NR_fR_h$), —$SR_f$, —$S(O)R_f$, —$S(O)_2R_f$, —$OR_f$, —$N(R_f)(R_h)$, —$C(O)R_f$, —$C(O)OR_f$, —$C(O)NR_fR_h$, —$C(O)N(H)NR_fR_h$, —$N(R_c)C(O)OR_f$, —$N(R_c)SO_2NR_fR_h$, —$N(R_c)C(O)NR_fR_h$, -alkylN($R_c$)C(O)$OR_f$, -alkylN($R_e$)$SO_2NR_fR_h$, and -alkylN($R_c$)C(O)$NR_fR_h$;

alternatively, $R_c$ and $R_d$, together with the nitrogen atom to which they are attached, form a three- to six-membered ring selected from the group consisting of heteroaryl and heterocycle, wherein the heteroaryl and heterocycle are each independently optionally substituted at each occurrence with at least 1, 2 or 3 substituents each of which is independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_f$), -(alkyl)($NR_fR_h$), —$SR_f$, —$S(O)R_f$, —$S(O)_2R_f$, —$OR_f$, —$N(R_f)(R_h)$, —$C(O)R_f$, —$C(O)OR_f$ and —$C(O)NR_fR_h$;

$R_e$ is independently selected at each occurrence from the group consisting of hydrogen, alkenyl, alkyl and cycloalkyl;

$R_f$ and $R_h$ are each independently selected at each occurrence from the group consisting of hydrogen, alkyl, alkenyl, aryl, arylalkyl, cycloalkyl, cycloalkylalkyl, cycloalkenyl, cycloalkenylalkyl, heterocycle, heterocyclealkyl, heteroaryl and heteroarylalkyl; wherein each $R_f$ and $R_h$ is independently optionally substituted at each occurrence with at least 1, 2 or 3 substituents each of which is independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —$NH_2$, —N(H)(alkyl), —N(alkyl)$_2$, —S(alkyl), —S(O)(alkyl), —$SO_2$alkyl, -alkyl-OH, -alkyl-O-alkyl, -alkyl$NH_2$, -alkylN(H)(alkyl), -alkylN(alkyl)$_2$, -alkylS(alkyl), -alkylS(O)(alkyl), -alkyl$SO_2$alkyl, —N(H)C(O)$NH_2$, —C(O)OH, —C(O)O(alkyl), —C(O)alkyl, —C(O)$NH_2$, —C(O)$NH_2$, —C(O)N(H)(alkyl), and —C(O)N(alkyl)$_2$;

alternatively, $R_f$ and $R_h$ together with the nitrogen atom to which they are attached, form a three- to seven-membered ring selected from the group consisting of heterocycle and heteroaryl; wherein the heterocycle and heteroaryl are each independently optionally substituted at each occurrence with at least 1, 2 or 3 substituents each of which is independently selected from the group consisting of alkyl, alkenyl, alkynyl, cyano, halo, oxo, nitro, aryl, arylalkyl, cycloalkyl, cycloalkenyl, heterocycle, heteroaryl, heteroaryialkyl, —OH, —O(alkyl), —$NH_2$, —N(H)(alkyl), —N(alkyl)$_2$, —S(alkyl), —S(alkyl), —S(O)(alkyl), -alkyl-OH, -alkyl-O-alkyl, -alkyl$NH_2$, -alkylN(H)(alkyl), -alkylS(alkyl), -alkylS(O)(alkyl), -alkyl$SO_2$alkyl, -alkylN(alkyl)$_2$, —N(H)C(O)$NH_2$, —C(O)OH, —C(O)(alkyl), —C(O)alkyl, —C(O)$NH_2$, —C(O)$NH_2$, —C(O)N(H)(alkyl), and —C(O)N(alkyl)$_2$;

$R_k$ is independently selected at each occurrence from the group consisting of hydrogen, alkenyl, alkyl, aryl, arylalkyl, cyanoalkyl, cycloalkenyl, cycloalkenylalkyl, cycloalkyl, cycloalkylalkyl, formylalkyl, haloalkyl, heteroaryl, heteroarylalkyl, heterocycle, heterocyclealkyl, nitroalkyl, $R_aR_b$Nalkyl-, $R_a$Oalkyl-, $R_aR_b$NC(O)—, $R_aR_b$NC(O)alkyl, $R_aS$—, $R_aS(O)$—, $R_aSO_2$—, $R_aS$-alkyl-, $R_a(O)$Salkyl-, $R_aSO_2$alkyl-, $R_aOC(O)$—, $R_aOC(O)$alkyl-, $R_aC(O)$—, and $R_aC(O)$alkyl-, wherein each $R_k$ is independently optionally substituted at each occurrence with at least 1, 2, or 3 substituents each of which is independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), —$SR_c$, —$S(O)R_c$, —$SO_2R_c$, —$OR_c$, —$N(R_c)(R_d)$, —$C(O)R_c$, —$C(O)OR_c$ and —$C(O)NR_cR_d$;

$R_p$ is independently selected at each occurrence from the group consisting of hydrogen, alkenyl, alkyl, aryl, arylalkyl, cyanoalkyl, cycloalkenyl, cycloalkenylalkyl, cycloalkyl, cycloalkylalkyl, formylalkyl, haloalkyl, heteroaryl, heteroarylalkyl, heterocycle, heterocyclealkyl, and nitroalkyl, wherein each $R_p$ is independently optionally substituted at each occurrence with at least 1, 2, or 3 substituents each of which is independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)R$_c$, —SO$_2$R$_c$, —OR$_c$, —N(R$_c$)(R$_d$), —C(O)R$_c$, —C(O)OR$_c$ and —C(O)NR$_c$R$_d$;

m is 1, 2, 3, or 4;

n is 1, 2, 3, or 4; and wherein at least one R$^5$ is R$_a$SO$_2$N(R$_f$)alkyl-.

In one embodiment, A is a monocyclic ring selected from the group consisting of aryl and heteroaryl.

In another embodiment, A is heteroaryl, and R$^2$ and R$^3$ together with the carbon atoms to which they are attached form a five- or six-membered ring selected from the group consisting of phenyl, pyridyl, pyrimidinyl, pyridazinyl, thienyl, furanyl, pyrrolyl, pyrazolyl, oxazolyl, thiazolyl, imidazolyl, isoxazolyl, isothiazolyl, triazolyl, thiadiazolyl, tetrazolyl, cyclopentyl and cyclohexyl.

In yet another embodiment, A is thienyl, and R$^2$ and R$^3$ together with the carbon atoms to which they are attached form a five- or six-membered ring selected from the group consisting of phenyl, pyridyl, pyrimidinyl, pyridazinyl, thienyl, furanyl, pyrrolyl, pyrazolyl, oxazolyl, thiazolyl, imidazolyl, isoxazolyl, isothiazolyl, triazolyl, thiadiazolyl, tetrazolyl, cyclopentyl and cyclohexyl. For example, A can be thienyl, and R$^2$ and R$^3$, together with the carbon atoms to which they are attached, form a phenyl ring.

In still another embodiment, A is pyridyl, phenyl, thienyl, imidazolyl, benzimidazolyl, benzoxazolyl or benzoxazinyl, R$^2$ and R$^3$ together with the carbon atoms to which they are attached form a five- or six-membered ring selected from the group consisting of phenyl, pyridyl, thienyl, pyrimidinyl, pyrazolyl, pyridazinyl, cyclohexyl and cyclopentyl, and R$^4$ is hydroxy.

In a further embodiment, A is pyridyl, phenyl, thienyl, imidazolyl, benzimidazolyl, benzoxazolyl or benzoxazinyl, R$^2$ and R$^3$ together with the carbon atoms to which they are attached form a five- or six-membered ring (hereinafter the "B" ring) selected from the group consisting of phenyl, pyridyl, thienyl, pyrimidinyl, pyrazolyl, pyridazinyl, cyclohexyl and cyclopentyl, R$^4$ is hydroxy, R$^1$ is cyclobutyl-N(H)—, n is 1, and R$^5$ is R$_a$SO$_2$N(H)—R$_j$—, wherein R$_a$ is defined above or, preferably, CH$_3$—or C$_2$-C$_4$alkyl, and R$_j$ is —CH$_2$—or C$_2$-C$_4$alkylene. In one example, A is phenyl, and the B ring is pyridyl. In another example, A is phenyl, and the B ring is thienyl. In yet another example, A is phenyl, and the B ring is phenyl. In a further example, A is thienyl (e.g.,

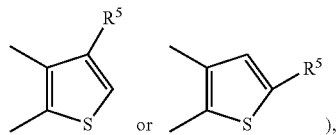

and the B ring is phenyl. In still another example, A is thienyl (e.g.,

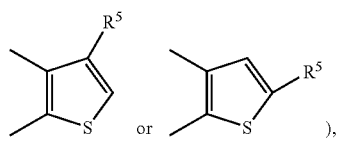

and the B ring is pyridyl. In still yet another example, A is pyridyl, and the B ring is phenyl. The B ring can be optionally substituted with at least one R$^6$ which is independently selected at each occurrence from the group consisting of alkyl, alkenyl, alkynyl, halo, cyano, nitro, haloalkyl, haloalkoxy, aryl, heteroaryl, heterocycle, arylalkyl, heteroarylalkyl, heterocyclealkyl, -(alkyl)(OR$_k$), -(alkyl)(NR$_a$R$_b$), —SR$_a$, —S(O)R$_a$, —S(O)$_2$R$_a$, —OR$_k$, —N(R$_a$)(R$_b$), —C(O)R$_a$, —C(O)OR$_a$ and —C(O)NR$_a$R$_b$. Each R$^6$ can also be independently optionally substituted with at least 1, 2 or 3 substituents each of which is independently selected from the group consisting of alkyl, alkenyl, alkynyl, oxo, halo, haloalkyl, cyano, nitro, —OR$_a$, —NR$_a$R$_b$, —SR$_a$, —SOR$_a$, —SO$_2$R$_a$, —C(O)OR$_a$, —C(O)NR$_a$R$_b$ and —NC(O)R$_a$.

In yet another embodiment, a compound of the present invention is N-[(3-{1-[(cyclobutyl)amino]-4-hydroxy-2-oxo-1,2-dihydro-quinolin-3-yl}-1,1-dioxo-1,4-dihydro-1λ$^6$-thieno[2,3-e][1,2,4]thiadiazin-7-yl)methyl]methanesulfonamide (hereinafter "compound I"). The present invention has discovered that compound I has unexpectedly improved pharmacokinetic profiles, including increased concentrations of the compounds in liver after oral administration, as compared to other compounds.

In another embodiment, the present invention provides pure or substantially pure compound I, or a pure or substantially pure pharmaceutically acceptable salt, stereoisomer or tautomer thereof.

The present invention also features pharmaceutical compositions comprising the compounds of the present invention or pharmaceutically acceptable salt forms thereof, and a pharmaceutically acceptable carrier. A pharmaceutical composition of the present invention can include at least 1,2, 3 or more compounds of the present invention and, optionally, at least 1, 2, 3 or more other therapeutic agents, such as immune modulators or other anti-viral agents (e.g., anti-HCV, anti-HBV or anti-HIV agents) or a combination thereof.

The present invention further features methods of using the compounds of the present invention to inhibit HCV RNA-dependent RNA polymerase. The methods comprise contacting a compound of the present invention (e.g., compound I), or a pharmaceutically acceptable salt, stereoisomer or tautomer thereof, with an HCV RNA-dependent RNA polymerase, thereby inhibiting the activity of the RNA polymerase.

In addition, the present invention features methods of using the compounds of the present invention to inhibit HCV replication. The methods comprise contacting HCV virus, or cells infected with HCV virus, with an effective amount of a compound of the present invention (e.g., compound I) or a pharmaceutically acceptable salt, stereoisomer or tautomer thereof, thereby inhibiting HCV virus replication.

The present invention also features methods of using the compounds of the present invention to treat or prevent HCV infection. The methods comprise administering to a patient in need of such treatment an effective amount of a compound of the present invention (e.g., compound I) or a pharmaceutically acceptable salt, stereoisomer or tautomer thereof, thereby treating or preventing HCV infection in the patient.

The present invention further provides processes of making the compounds of the present invention, and intermediates employed in the processes.

Other features, objects, and advantages of the present invention are apparent in the detailed description that follows. It should be understood, however, that the detailed description, while indicating preferred embodiments of the invention, are given by way of illustration only, not limitation. Various changes and modifications within the scope of the invention will become apparent to those skilled in the art from the detailed description.

BRIEF DESCRIPTION OF THE DRAWINGS

The drawing is provided for illustration, not limitation.

DETAILED DESCRIPTION OF THE INVENTION

Figure 1:
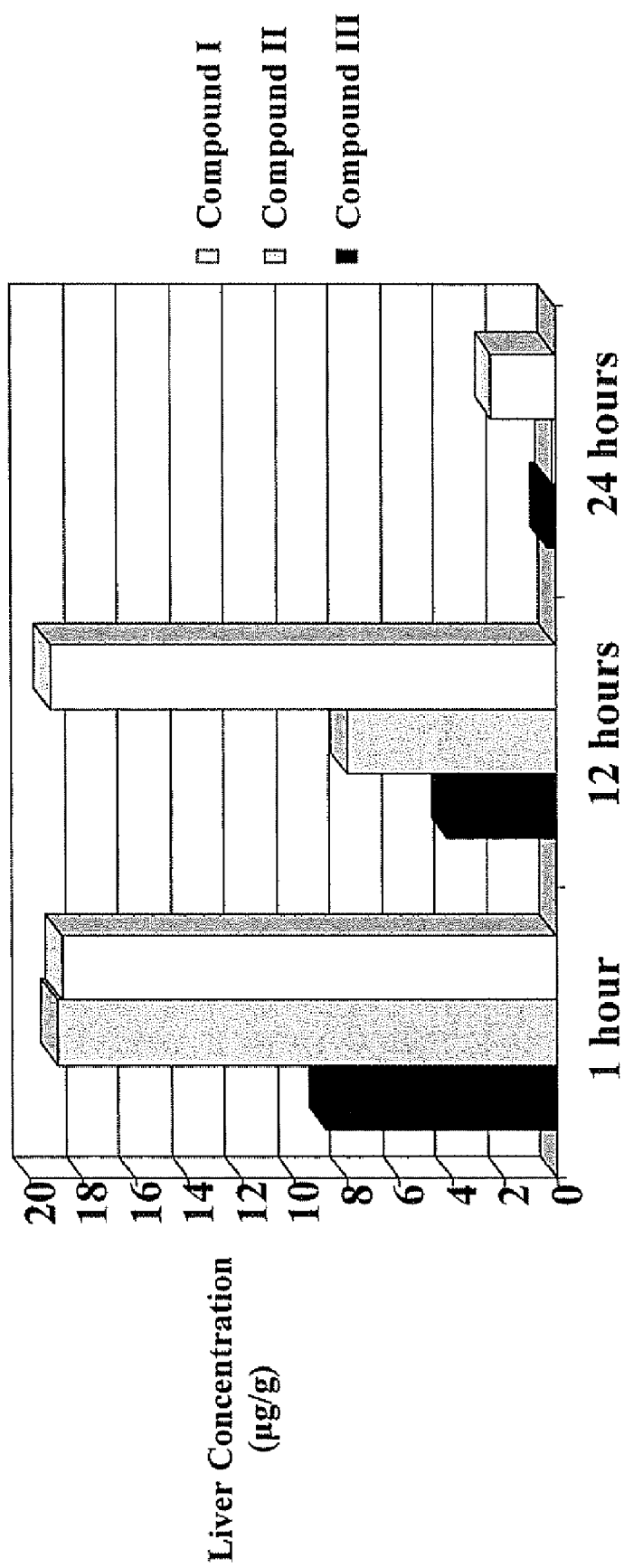
FIG. 1 shows liver concentrations of compounds I, II and III at different time points after oral dosing in rats.

As used in the present specification the following terms have the meanings indicated below, As used herein, the singular forms "a" and "an" may include plural reference unless the context clearly dictates otherwise.

The term "alkyl," as used herein, refers to a saturated straight or branched hydrocarbon chain group containing 1, 2, 3, 4, 5, 6, 7, 8, 9 or 10 carbon atoms. Examples of alkyl groups include butyl, methyl, 2-methylbutyl, and the like.

The terms "alkylene" or "alkylenyl," as used herein, refer to a divalent group derived from a straight or branched saturated hydrocarbon chain having 1, 2, 3, 4, 5, 6, 7, 8, 9 or 10 carbon atoms. Representative examples of alkylene include, but are not limited to, —$CH_2$—, —$CH_2CH_2$—, —$CH_2CH_2CH_2$—, —$CH_2CH_2CH_2CH_2$—, and —$CH_2CH(CH_3)CH_2$—.

The term "alkenyl," as used herein, refers to a straight or branched hydrocarbon chain group of 2, 3, 4, 5, 6, 7, 8, 9 or 10 carbon atoms containing at least one carbon-carbon double bond. Examples of alkenyl groups include allyl, propenyl, 3-methyl-2-butenyl, and the like.

The term "alkynyl," as used herein, refers to a straight or branched chain hydrocarbon of 2, 3, 4, 5, 6, 7, 8, 9 or 10 carbon atoms containing at least one carbon-carbon triple bond. Examples of alkynyl groups include ethynyl, 2-methyl-3-butynyl, 3-pentynyl, and the like.

The term "alkoxy," as used herein, refers to an alkyl group attached to the parent molecular moiety through an oxygen atom. Examples of alkoxy groups include tert-butoxy, methoxy, isopropoxy, and the like.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxy methoxy, 2-ethoxyethoxy, 2-methoxyethoxy, and methoxymethoxy.

The term "alkoxyalkoxyalkyl" as used herein, means an alkoxyalkoxy group, as defined herein, appended to the parent molecular moiety through an alkyl group, as defined herein. Representative examples of alkoxyalkoxyalkyl include, but are not limited to, tert-butoxymethoxy methyl, ethoxymethoxymethyl, (2-methoxyethoxy)methyl, and 2-(2-methoxyethoxy)ethyl.

The term "alkoxyalkyl," as used herein, refers to an alkyl group substituted by at least one alkoxy group.

The term "alkoxycarbonyl," as used herein, refers to an alkoxy group attached to the parent molecular moiety through a carbonyl group. Examples of alkoxycarbonyl groups include tert-butoxycarbonyl, ethoxycarbonyl, methoxycarbonyl, and the like.

The term "alkoxycarbonylalkyl," as used herein, refers to an alkoxycarbonyl group attached to the parent molecular moiety through an alkyl group.

The term "alkylcarbonyl," as used herein, refers to an alkyl group attached to the parent molecular moiety through a carbonyl group. Examples of alkylcarbonyl groups include acyl, butanoyl, 2,2-dimethylpropanoyl, and the like.

The term "alkylcarbonylaikyi" as used herein, means an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylsulfanyl," as used herein, refers to an alkyl group attached to the parent molecular moiety through a sulfur atom. Examples of alkylsulfanyl groups include methylsulfanyl, (1-methylethyl)sulfanyl, (2-methylpropyl)sulfanyl, and the like.

The term "alkylsulfanylalkyl," as used herein, refers to an alkylsulfanyl group attached to the parent molecular moiety through an alkyl group.

The term "alkylsulfinyl," as used herein, refers to an alkyl group attached to the parent molecular moiety through a —S(O)— group, The term "alkylsulfinylalkyl," as used herein, refers to an alkylsulfinyl group attached to the parent molecular moiety through an alkyl group.

The term "alkylsulfonyl," as used herein, refers to an alkyl group attached to the parent molecular moiety through a —$S(O)_2$— group.

The term "alkylsulfonylalkyl," as used herein, refers to an alkylsulfonyl group attached to the parent molecular moiety through an alkyl group.

The term "aryl" as used herein, refers to a phenyl group, or a bicyclic or tricyclic hydrocarbon fused ring systems wherein one or more of the rings is a phenyl group. Bicyclic fused ring systems have a phenyl group fused to a monocyclic cycloalkenyl group, as defined herein, a monocyclic cycloalkyl group, as defined herein, or another phenyl group. Tricyclic fused ring systems are exemplified by a bicyclic fused ring system fused to a monocyclic cycloalkenyl group, as defined herein, a monocyclic cycloalkyl group, as defined herein, or another phenyl group. Examples of aryl groups include anthracenyl, azulenyl, fluorenyl, indanyl, indenyl, naphthyl, phenyl, tetrahydronaphthyl, and the like. The aryl groups of the present invention can be connected to the parent molecular moiety through any substitutable carbon atom of the group. The aryl groups of the present invention can be substituted with 0, 1, 2, 3, 4 or 5 substituents independently selected from the group consisting of alkyl, alkenyl, alkynyl, cyano, formyl, halo, nitro, oxo, —$OR_a$, —$OC(O)R_a$, —$OC(O)OR_a$, —$OC(O)NR_aR_b$, —$OSO_2R_a$, —$OSO_2NR_aR_b$, —$SR_a$, —$SOR_a$, —$SO_2R_a$, —$SO_2OR_a$, —$SO_2NR_aR_b$, —$NR_aR_b$, —$N(R_e)C(O)R_a$, —$N(R_e)C(O)OR_a$, —$N(R_e)C(O)NR_aR_b$, —$N(R_e)SO_2R_a$, —$N(R_e)SO_2NR_aR_b$, —$N(R_e)SO_2N(R_e)C(O)OR_a$, —$C(O)R_a$, —$C(O)OR_a$, —$C(O)NR_aR_b$, cycloalkyl, cycloalkenyl, heterocycle, a second aryl group and heteroaryl; wherein each of the alkyl, alkenyl and alkynyl is independently substituted with 0, 1, 2 or 3 substituents independently selected from the group consisting of cyano, formyl, halo, nitro, oxo, —$OR_a$, —$OC(O)R_a$, —$OC(O)OR_a$, —$OC(O)NR_aR_b$, —$OSO_2R_a$, —$OSO_2NR_aR_b$, —$SR_a$, —$SOR_a$, —$SO_2R_a$, —$SO_2OR_a$, —$SO_2NR_aR_b$, —$NR_aR_b$, —$N(R_e)C(O)R_a$, —$N(R_c)C(O)OR_a$, —$N(R_e)C(O)NR_aR_b$, —$N(R_e)SO_2R_a$, —$N(R_e)SO_2NR_aR_b$, —$N(R_e)SO_2N(R_e)C(O)OR_a$, —$C(O)R_a$, —$C(O)OR_a$, —$C(O)NR_aR_b$, cycloalkyl, cycloalkenyl, heterocycle, a second aryl group and heteroaryl; wherein $R_a$, $R_b$ and $R_c$ are defined hereinabove, and wherein the second aryl group, the heteroaryl, the cycloalkyl, the cycloalkenyl and the heterocycle can be substituted with 0, 1, 2 or 3 substituents independently selected from the group consisting of —OH, —O(alkyl), alkyl, alkenyl, alkynyl, cyano, formyl, halo, haloalkoxy, haloalkyl, nitro, —$NH_2$, —N(H)(alkyl), —$N(alkyl)_2$, —C(O)OH, —C(O)O(alkyl), —$C(O)NH_2$, —C(O)N(H)(alkyl), —$C(O)N(alkyl)_2$ and oxo, The term "arylalkenyl," as used herein, refers to an aryl group attached to the parent molecular moiety through an alkenyl group.

The term "arylalkoxy," as used herein, refers to an arylalkyl group attached to the parent molecular moiety through an oxygen atom.

The term "arylalkyl," as used herein, refers to an aryl group attached to the parent molecular moiety through an alkyl group, The term "arylcarbonyl," as used herein, refers to an aryl group attached to the parent molecular moiety through a carbonyl group.

The term "arylcarbonylalkyl" as used herein, means an arylcarbonyl group, as defined herein, appended to the parent molecular moiety through an alkyl group, as defined herein.

The term "aryloxy," as used herein, refers to an aryl group attached to the parent molecular moiety through an oxygen atom.

The term "aryloxyalkyl," as used herein, refers to an aryloxy group attached to the parent molecular moiety through an alkyl atom.

The term "arylsulfanyl," as used herein, refers to an aryl group attached to the parent molecular moiety through a sulfur atom.

The term "arylsulfonylalkyl," as used herein, refers to an arylsulfanyl group attached to the parent molecular moiety through an alkyl group.

The term "arylsulfonyl," as used herein, refers to an aryl group attached to the parent molecular moiety through a sulfonyl group.

The term "arylsulfonylalkyl," as used herein, refers to an arylsulfonyl group attached to the parent molecular moiety through an alkyl group.

The term "carboxy," as used herein, refers to —$CO_2H$.

The term "carboxyalkyl," as used herein, refers to a carboxy group attached to the parent molecular moiety through an alkyl group.

The term "cyano," as used herein, refers to —CN.

The term "cyanoalkyl," as used herein, refers to a cyano group attached to the parent molecular moiety through an alkyl group.

The term "cycloalkenyl," as used herein, refers to a non-aromatic, partially unsaturated, monocyclic, bicyclic or tricyclic ring system, having three to fourteen carbon atoms and zero heteroatom, Examples of cycloalkenyl groups include cyclohexenyl, octahydronaphthalenyl, norbornylenyl, and the like. The cycloalkenyl groups of the present invention can be substituted with 0, 1, 2, 3, 4 or 5 substituents independently selected from the group consisting of alkyl, alkenyl, alkynyl, cyano, formyl, halo, nitro, oxo, —$OR_a$, —$OC(O)R_a$, —$OC(O)OR_a$, —$OC(O)NR_aR_b$, —$OSO_2R_a$, —$OSO_2NR_aR_b$, —$SR_a$, —$SOR_a$, —$SO_2R_a$, —$SO_2OR_a$, —$SO_2NR_aR_b$, —$NR_aR_b$, —$N(R_c)C(O)R_a$, —$N(R_c)C(O)OR_a$, —$N(R_c)C(O)NR_aR_b$, —$N(R_c)SO_2R_a$, —$N(R_c)SO_2NR_aR_b$, —$N(R_c)SO_2N(R_c)C(O)OR_a$, —$C(O)R_a$, —$C(O)OR_a$, —$C(O)NR_aR_b$, cycloalkyl, a second cycloalkenyl, heterocycle, aryl and heteroaryl; wherein $R_a$, $R_b$ and $R_c$ are defined hereinabove, and wherein the cycloalkyl, the second cycloalkenyl, the heterocycle, the aryl and the heteroaryl can be substituted with 0, 1, 2 or 3 substituents independently selected from the group consisting of —OH, —O(alkyl), alkyl, alkenyl, alkynyl, cyano, formyl, halo, oxo, haloalkoxy, haloalkyl, nitro, oxo, —$NH_2$, —N(H)(alkyl), —$N(alkyl)_2$, —C(O)OH, —C(O)O(alkyl), —$C(O)NH_2$, —C(O)N(H)(alkyl), and —$C(O)N(alkyl)_2$.

The term "cycloalkenylalkyl," as used herein, refers to a cycloalkenyl group attached to the parent molecular moiety through an alkyl group.

The term "cycloalkyl," as used herein, refers to a saturated monocyclic, bicyclic, or tricyclic hydrocarbon ring system having three to fourteen carbon atoms and zero heteroatom. Examples of cycloalkyl groups include cyclopropyl, cyclobutyl, cyclopentyl, cyclohexyl, cycloheptyl, bicyclo[3.1.1]heptyl, 6,6-dimethylbcyclo[3.1.1]heptyl, adamantyl, and the like. The cycloalkyl groups of the present invention can be substituted with 0, 1, 2, 3, 4 or 5 substituents independently selected from the group consisting of alkyl, alkenyl, alkynyl, cyano, formyl, halo, nitro, oxo, —$OR_a$, —$OC(O)R_a$, —$OC(O)OR_a$, —$OC(O)NR_aR_b$, —$OSO_2R_a$, —$OSO_2NR_aR_b$, —$SR_a$, —$SOR_a$, —$SO_2R_a$, —$SO_2OR_a$, —$SO_2NR_aR_b$, —$NR_aR_b$, —$N(R_c)C(O)R_a$, —$N(R_c)C(O)OR_a$, —$N(R_c)C(O)NR_aR_b$, —$N(R_c)SO_2R_a$, —$N(R_c)SO_2NR_aR_b$, —$N(R_c)SO_2N(R_c)C(O)OR_a$, —$C(O)R_a$, —$C(O)OR_a$, —$C(O)NR_aR_b$, a second cycloalkyl, cycloalkenyl, heterocycle, aryl, heteroaryl and ethylenedioxy; wherein each of the alkyl, alkenyl and alkynyl is independently substituted with 0, 1, 2 or 3 substituents independently selected from the group consisting of cyano, formyl, halo, nitro, oxo, —$OR_a$, —$OC(O)R_a$, —$OC(O)OR_a$, —$OC(O)NR_aR_b$, —$OSO_2R_a$, —$OSO_2NR_aR_b$, —$SR_a$, —$SOR_a$, —$SO_2R_a$, —$SO_2OR_a$, —$SO_2NR_aR_b$, —$NR_aR_b$, —$N(R_c)C(O)R_a$, —$N(R_c)C(O)OR_a$, —$N(R_c)C(O)NR_aR_b$, —$N(R_c)SO_2R_a$, —$N(R_c)SO_2NR_aR_b$, —$N(R_c)SO_2(R_a)C(O)OR_a$, —$C(O)R_a$, —$C(O)OR_a$, —$C(O)NR_aR_b$, a second cycloalkyl, cycloalkenyl, heterocycle, aryl and heteroaryl; wherein $R_a$, $R_b$ and $R_c$ are defined hereinabove, and wherein the second cycloalkyl, the cycloalkenyl, the heterocycle, the aryl and the heteroaryl can be substituted with 0, 1, 2 or 3 substituents independently selected from the group consisting of —OH, —O(alkyl), alkyl, alkenyl, alkynyl, cyano, formyl, halo, haloalkoxy, haloalkyl, nitro, oxo, —$NH_2$, —N(H)(alkyl), —$N(alkyl)_2$, —C(O)OH, —C(O)(alkyl), —$C(O)NH_2$, —C(O)N(H)(alkyl), and —$C(O)N(alkyl)_2$.

The term "cycloalkylalkenyl," as used herein, refers to a cycloalkyl group attached to the parent molecular moiety through an alkenyl group.

The term "cycloalkylalkyl," as used herein, refers to a cycloalkyl group attached to the parent molecular moiety through an alkyl group The term "formyl," as used herein, refers to —CHO.

The term "formylalkyl," as used herein, refers to a formyl group attached to the parent molecular moiety through an alkyl group.

The terms "halo," and "halogen," as used herein, refer to F, Cl, Br, and I.

The term "haloalkoxy," as used herein, refers to a haloalkyl group attached to the parent molecular moiety through an oxygen atom.

The term "haloalkoxyalkyl," as used herein, refers to a haloalkoxy group attached to the parent molecular moiety through an alkyl group.

The term "haloalkyl," as used herein, refers to an alkyl group substituted by one, two, three, or four halogen atoms.

The term "heteroaryl," as used herein, refers to an aromatic five- or six-membered ring where at least one atom is selected from the group consisting of N, O, and S, and the remaining atoms are carbon. The term "heteroaryl" also includes bicyclic systems where a heteroaryl ring is fused to a phenyl group, a monocyclic cycloalkyl group, as defined herein, a heterocycle group, as defined herein, or an additional heteroaryl group. The term "heteroaryl" also includes tricyclic systems where a bicyclic system is fused to a phenyl group, a monocyclic cycloalkyl group, as defined herein, a heterocycle group, as defined herein, or an additional heteroaryl group. The heteroaryl groups are connected to the parent molecular moiety through any substitutable carbon or nitrogen atom in the groups. Examples of heteroaryl groups include benzothienyl, benzoxazolyl, benzimidazolyl, benzoxadiazolyl, dibenzofuranyl, dihydrobenzothiazolyl, furanyl, imidazolyl, indazolyl, indolyl, isoindolyl, isoxazolyl, isoquinolinyl, isothiazolyl, oxadiazolyl, oxazolyl, thiazolyl, thienopyridinyl, thienyl, triazolyl, thiadiazolyl, tetrazolyl, pyridyl, pyridazinyl, pyrimidinyl, pyrazinyl, pyrazolyl, pyrrolyl, quinolinyl, tetrahydroquinolinyl, tetrahydropyranyl, triazinyl, and the like. The heteroaryl groups of the present invention can be substituted with 0, 1, 2, 3, 4 or 5 substituents independently selected from the group consisting of alkyl, alkenyl, alkynyl, cyano, formyl, halo, nitro, oxo, —$OR_a$, —$OC(O)R_a$, —$OC(O)OR_a$, —$OC(O)NR_aR_b$, —$OSO_2R_a$, —$OSO_2NR_aR_b$, —$SR_a$, —$SOR_a$, —$SO_2R_a$, —$SO_2OR_a$, —$SO_2NR_aR_b$, —$NR_aR_b$, —$N(R_c)C(O)R_a$, —$N(R_c)C(O)OR_a$, —$N(R_c)C(O)NR_aR_b$, —$N(R_c)SO_2R_a$, —$N(R_c)SO_2NR_aR_b$, —$N(R_c)SO_2N(R_c)C(O)OR_a$, —$C(O)R_a$, —$C(O)OR_a$, —$C(O)NR_aR_b$, cycloalkyl, cycloalkenyl, heterocycle, aryl and a second heteroaryl group; wherein each of the alkyl, alkenyl and alkynyl is independently substituted with 0, 1, 2 or 3 substituents independently selected from the group consisting of cyano, formyl, halo, nitro, oxo, —$OR_a$, —$OC(O)R_a$, —$OC(O)OR_a$, —$OC(O)NR_aR_b$, —$OSO_2R_a$, —$OSO_2NR_aR_b$, —$SR_a$, —$SOR_a$, —$SO_2R_a$, —$SO_2OR_a$, —$SO_2NR_aR_b$, —$NR_aR_b$, —$N(R_e)C(O)R_a$, —$N(R_e)C(O)OR_a$, —$N(R_c)C(O)NR_aR_b$, —$N(R_e)SO_2R_a$, —$N(R_e)SO_2N(R_e)C(O)OR_a$, —$C(O)R_a$, —$C(O)OR_a$, —$C(O)NR_aR_b$, cycloalkyl, cycloalkenyl, heterocycle, aryl and a second heteroaryl group; wherein $R_a$, $R_b$ and $R_c$ are defined hereinabove, and wherein the second heteroaryl group, the aryl, the cycloalkyl, the cycloalkenyl and the heterocycle can be independently substituted with 0, 1, 2 or 3 substituents independently selected from the group consisting of —OH, —O(alkyl), alkyl, alkenyl, alkynyl, cyano, formyl, halo, haloalkoxy, haloalkyl, nitro, —$NH_2$, —N(H)(alkyl), —N(alkyl)$_2$, —C(O)OH, —C(O)O(alkyl), —C(O)NH$_2$, —C(O)N(H)(alkyl), —C(O)N(alkyl)$_2$ and oxo. In addition, the nitrogen heteroatoms can be optionally quaternized or oxidized to the N-oxide,. Also, the nitrogen containing rings can be optionally N-protected, The term "heteroarylalkenyl," as used herein, refers to a heteroaryl group attached to the parent molecular moiety through an alkenyl group, The term "heteroarylalkyl," as used herein, refers to a heteroaryl group attached to the parent molecular moiety through an alkyl group.

The term "heteroarylsulfonyl," as used herein, refers to a heteroaryl group attached to the parent molecular moiety through a sulfonyl group.

The term "heteroarylsulfonylalkyl," as used herein, refers to a heteroarylsulfonyl group attached to the parent molecular moiety through an alkyl group.

The term "heterocycle," as used herein, refers to cyclic, non-aromatic, saturated or partially unsaturated, three, four, five-, six-, or seven-membered rings containing at least one atom selected from the group consisting of oxygen, nitrogen, and sulfur. The term "heterocycle" also includes bicyclic systems where a heterocycle ring is fused to a phenyl group, a monocyclic cycloalkenyl group, as defined herein, a monocyclic cycloalkyl group, as defined herein, or an additional monocyclic heterocycle group The term "heterocycle" also includes tricyclic systems where a bicyclic system is fused to a phenyl group, a monocyclic cycloalkenyl group, as defined herein, a monocyclic cycloalkyl group, as defined herein, or an additional monocyclic heterocycle group. The heterocycle groups of the invention are connected to the parent molecular moiety through any substitutable carbon or nitrogen atom in the group. Examples of heterocycle groups include benzoxazinyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, tetrahydropyranyl, and the like. The heterocycle groups of the present invention can be substituted with 0, 1, 2, 3, 4 or 5 substituents independently selected from the group consisting of alkyl, alkenyl, alkynyl, cyano, formyl, halo, nitro, oxo, —$OR_a$, —$OC(O)R_a$, —$OC(O)OR_a$, —$OC(O)NR_aR_b$, —$OSO_2R_a$, —$OSO_2NR_aR_b$, —$SR_a$, —$SOR_a$, —$SO_2R_a$, —$SO_2OR_a$, —$SO_2NR_aR_b$, —$NR_aR_b$, —$N(R_c)C(O)R_a$, —$N(R_e)C(O)OR_a$, —$N(R_e)C(O)NR_aR_b$, —$N(R_e)SO_2R_a$, —$N(R_e)SO_2NR_aR_b$, —$N(R_e)SO_2N(R_e)C(O)OR_a$, —$C(O)R_a$, —$C(O)OR_a$, —$C(O)NR_aR_b$, cycloalkyl, cycloalkenyl, a second heterocycle, aryl, heteroaryl and ethylenedioxy; wherein each of the alkyl, alkenyl and alkynyl is independently substituted with 0, 1, 2 or 3 substituents independently selected from the group consisting of cyano, formyl, halo, nitro, oxo, —$OR_a$, —$OC(O)R_a$, —$OC(O)OR_a$, —$OC(O)NR_aR_b$, —$OSO_2R_a$, —$OSO_2NR_aR_b$, —$SR_a$, —$SOR_a$, —$SO_2R_a$, —$SO_2OR_a$, —$SO_2NR_aR_b$, —$NR_aR_b$, —$N(R_e)C(O)R_a$, —$N(R_e)C(O)OR_a$, —$N(R_e)C(O)NR_aR_b$, —$N(R_e)SO_2R_a$, —$N(R_e)SO_2NR_aR_b$, —$N(R_e)SO_2N(R_e)C(O)OR_a$, —$C(O)R_a$, —$C(O)OR_a$, —$C(O)NR_aR_b$, cycloalkyl, cycloalkenyl, a second heterocycle, aryl and heteroaryl; wherein $R_a$, $R_b$ and $R_c$ are defined hereinabove, and wherein the cycloalkyl, cycloalkenyl, the second heterocycle, the aryl and the heteroaryl can be independently substituted with 0, 1, 2 or 3 substituents independently selected from the group consisting of —OH, —O(alkyl), alkyl, alkenyl, alkynyl, cyano, formyl, halo, haloalkoxy, haloalkyl, nitro, oxo, —$NH_2$, —N(H)(alkyl), —N(alkyl)$_2$, —C(O)OH, —C(O)O(alkyl), —C(O)NH$_2$, —C(O)N(H)(alkyl), and —C(O)N(alkyl)$_2$. In addition, the nitrogen heteroatoms can be optionally quatemized or oxidized to the N-oxide, Also, the nitrogen containing heterocyclic rings can be optionally N-protected.

The term "hetetocyclealkenyl," as used herein, refers to a heterocycle group attached to the parent molecular moiety through an alkenyl group, The term "heterocyclealkyl," as used herein, refers to a heterocycle group attached to the parent molecular moiety through an alkyl group, The term "heterocyclecarbonyl" as used herein, means a heterocycle, as defined herein, appended to the parent molecular moiety through a carbonyl group, as defined herein. Representative examples of heterocyclecarbonyl include, but are not limited to, pyrrolidinylcarbonyl and piperazin-1-ylcarbonyl The term "hydroxy," as used herein, refers to —OH.

The term "hydroxyalkyl," as used herein, refers to an alkyl group substituted by at least one hydroxy group.

The term "nitro," as used herein, refers to —$NO_2$.

The term "nitroalkyl," as used herein, refers to an alkyl group substituted by at least one nitro group The term "oxo," as used herein, refers to =O.
The term "sulfanyl," as used herein, refers to —S—.
The term "sulfinyl," as used herein, refers to —SO—.
The term "sulfonyl," as used herein, refers to —SO$_2$.

It is understood that alkenyl, alkoxy, alkoxyalkoxy, alkoxyalkoxyalkyl, alkoxyalkyl, alkoxycarbonyl, alkoxycarbonylalkyl, alkyl, alkylcarbonyl, alkylcarbonylalkyl, alkynyl, alkylsulfanyl, alkylsulfanylalkyl, alkylsulfinyl, alkylsulfinylalkyl, alkylsulfonyl, alkylsulfonylalkyl, arylalkenyl, arylalkoxy, arylalkyl, aryloxyalkyl, arylsulfanylalkyl, arylsulfonylalkyl, carboxyalkyl, cyanoalkyl, cycloalkenylalkyl, cycloalkenylalkenyl, cycloalkylalkyl, formylalkyl, haloalkoxy, haloalkoxyalkyl, haloalkyl, heteroarylalkenyl, heteroarylalkyl, heterosulfonylalkyl, heterocyclealkenyl, heterocyclealkyl, hydroxyalkyl and nitroalkyl may optionally be substituted.

The number of carbon atoms in a hydrocarbyl substituent can be indicated by the prefix "$C_x$-$C_y$," where x is the minimum and y is the maximum number of carbon atoms in the substituent. A prefix attached to a multiple-component substituent only applies to the first component that immediately follows the prefix. To illustrate, the term "alkylaryl" contains two components: alkyl and aryl. Thus, $C_1$-$C_6$alkylaryl refers to a $C_1$-$C_6$alkyl appended to the parent molecular moiety through an aryl group The present invention features compounds of formula (I) as described above, and pharmaceutically acceptable salts, stereoisomers or tautomers thereof.

In one embodiment, the present invention provides a compound of formula (II)

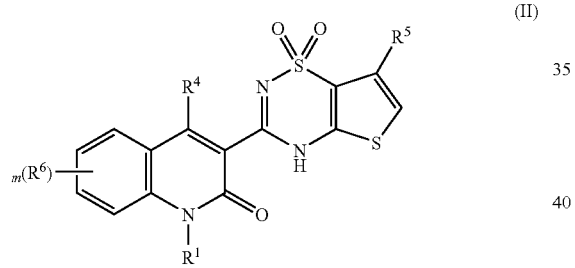

(II)

or a pharmaceutically acceptable salt form, stereoisomer or tautomer thereof wherein:

$R^1$ is cyclobutyl-N(H)—;

$R^4$ is hydroxy;

$R^5$ is $R_aSO_2NH$—$R_j$—, wherein $R_a$ is as defined immediately below or, preferably, $CH_3$— or $C_2$-$C_4$(alkyl, and $R_j$ is —$CH_2$— or $C_2$-$C_4$alkylene;

$R^6$ is independently selected at each occurrence from the group consisting of alkyl, alkenyl, alkynyl, halo, cyano, nitro, haloalkyl, haloalkoxy, aryl, heteroaryl, heterocycle, arylalkyl, heteroarylalkyl, heterocyclealkyl, -(alkyl)(OR$_k$), -(alkyl)(NR$_a$R$_b$), —SR$_a$, —S(O)R$_a$, —S(O)$_2$R$_a$, —OR$_k$, —N(R$_a$)(R$_b$), —C(O)R$_a$, —C(O)OR$_a$ and —C(O)NR$_a$R$_b$; wherein each $R^6$ is independently optionally substituted at each occurrence with at least 1, 2 or 3 substituents each of which is independently selected from the group consisting of alkyl, alkenyl, alkynyl, oxo, halo, haloalkyl, cyano, nitro, —OR$_a$, —NR$_a$R$_b$, —SR$_a$, —SOR$_a$, —SO$_2$R$_a$, —C(O)OR$_a$, —C(O)NR$_a$R$_b$ and —NC(O)R$_a$;

$R_a$ and $R_b$ are each independently selected at each occurrence from the group consisting of hydrogen, alkenyl, alkyl, alkylsulfanylalkyl, aryl, arylalkenyl, arylalkyl, cyanoalkyl, cycloalkenyl, cycloalkenylalkyl, cycloalkyl, cycloalkylalkyl, cycloalkylalkenyl, formylalkyl, haloalkyl, heteroaryl, heteroarylalkenyl, heteroarylalkyl, heterocycle, heterocyclealkenyl, heterocyclealkyl, hydroxyalkylcarbonyl, nitroalkyl, $R_cR_dN$—, $R_pO$—, $R_pO$alkyl-, $R_cR_d$Nalkyl-, $R_cR_d$NC(O)alkyl-, $R_cSO_2$—, $R_cSO_2$alkyl-, $R_cC(O)$—, $R_cC(O)$alkyl-, $R_cOC(O)$—, $R_cOC(O)$alkyl-, $R_eR_d$NalkylC(O)—, $R_cR_d$NC(O)—, $R_cR_d$NC(O)Oalkyl-, and $R_cR_d$NC(O)N(R$_e$)alkyl-, wherein $R_a$ and $R_b$ are each independently optionally substituted at each occurrence with at least 1 or 2 substituents each of which is independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

alternatively, $R_a$ and $R_b$, together with the nitrogen atom to which they are attached, form a three- to six-membered ring selected from the group consisting of heteroaryl and heterocycle, wherein the heteroaryl and heterocycle are each independently optionally substituted at each occurrence with at least 1, 2 or 3 substituents each of which is independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alky)(NR$_c$R$_d$), -alkylSO$_2$NR$_c$R$_d$, -alkylC(O)NR$_c$R$_d$, —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

$R_c$ and $R_d$ are each independently selected at each occurrence from the group consisting of hydrogen, —NR$_f$R$_h$, —OR$_f$, —CO(R$_f$), —SR$_f$, —SOR$_f$, —SO$_2$R$_f$, —C(O)NR$_f$R$_h$, —SO$_2$NR$_f$R$_h$, —C(O)OR$_f$, alkenyl, alkyl, alkynyl, cycloalkyl, cycloalkylalkyl, cycloalkenyl, cycloalkenylalkyl, aryl, arylalkyl, haloalkyl, heteroaryl, heteroarylalkyl, heterocycle and heterocyclealkyl; wherein each $R_c$ and $R_d$ is independently optionally substituted at each occurrence with at least 1, 2, or 3 substituents each of which is independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_f$), -(alkyl)(NR$_f$R$_h$), —SR$_f$, —S(O)R$_f$, —S(O)$_2$R$_f$, —OR$_f$, —N(R$_f$)(R$_h$), —C(O)R$_f$, —C(O)OR$_f$, —C(O)NR$_f$R$_h$, —C(O)N(H)NR$_f$R$_h$, —N(R$_c$)C(O)OR$_f$, —N(R$_c$)SO$_2$NR$_f$R$_h$, —N(R$_c$)C(O)NR$_f$R$_h$, -alkylN(R$_e$)C(O)OR$_f$, -alkylN(R$_c$)SO$_2$NR$_f$R$_h$, and -alkylN(R$_e$)C(O)NR$_f$R$_h$;

alternatively, $R_c$ and $R_d$, together with the nitrogen atom to which they are attached, form a three- to six-membered ring selected from the group consisting of heteroaryl and heterocycle, wherein the heteroaryl and heterocycle are each independently optionally substituted at each occurrence with at least 1, 2 or 3 substituents each of which is independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_f$), -(alkyl)(NR$_f$R$_h$), —SR$_f$, —S(O)R$_f$, —S(O)$_2$R$_f$, —OR$_f$, —N(R$_f$)(R$_h$), —C(O)R$_f$, —C(O)OR$_f$ and —C(O)NR$_f$R$_h$;

$R_e$ is selected from the group consisting of hydrogen, alkenyl, alkyl and cycloalkyl;

$R_f$ and $R_h$ are each independently selected at each occurrence from the group consisting of hydrogen, alkyl, alkenyl, aryl, arylalkyl, cycloalkyl, cycloalkylalkyl, cycloalkenyl, cycloalkenylalkyl, heterocycle, heterocyclealkyl, heteroaryl and heteroarylalkyl; wherein each $R_f$ and $R_h$ is independently optionally substituted at each occurrence with at least 1, 2 or 3 substituents each of which is independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —NH$_2$, —N(H)(alkyl), —N(alkyl)$_2$, —S(alkyl), —S(O)(alkyl), —SO$_2$alkyl, -alkyl—OH, -alkyl-O-alkyl, -alkylNH$_2$, -alkylN(H)(alkyl), -alkylN(alkyl)$_2$, -alkylS(alkyl), -alkylS(O)(alkyl), -alkylSO$_2$alkyl, —N(H)C(O)NH$_2$, —C(O)OH, —C(O)O(alkyl), —C(O)alkyl, —C(O)NH$_2$, —C(O)NH$_2$, —C(O)N(H)(alkyl), and —C(O)N(alkyl)$_2$;

alternatively, $R_f$ and $R_h$ together with the nitrogen atom to which they are attached, form a three- to seven-membered ring selected from the group consisting of heterocycle and heteroaryl; wherein the heterocycle and heteroaryl are each independently optionally substituted at each occurrence with at least 1, 2 or 3 substituents each of which is independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —NH$_2$, —N(H)(alkyl), —N(alkyl)$_2$, —S(alkyl), —S(alkyl), —S(O)(alkyl), -alkyl—OH, -alkyl-O-alkyl, -alkylNH$_2$, -alkylN(H)(alkyl), -alkylS(alkyl), -alkylS(O)(alkyl), -alkylSO$_2$alkyl, -alkylN(alkyl)$_2$, —N(H)C(O)NH$_2$, —C(O)OH, —C(O)(alkyl), —C(O)alkyl, —C(O)NH$_2$, —C(O)NH$_2$, —C(O)N(H)(alkyl), and —C(O)N(alkyl)$_2$;

$R_k$ is independently selected at each occurrence from the group consisting of hydrogen, alkenyl, alkyl, aryl, arylalkyl, cyanoalkyl, cycloalkenyl, cycloalkenylalkyl, cycloalkyl, cycloalkylalkyl, formylalkyl, haloalkyl, heteroaryl, heteroarylalkyl, heterocycle, heterocyclealkyl, nitroalkyl, $R_aR_bN$alkyl-, $R_aO$alkyl-, $R_aR_bNC(O)$—, $R_aR_bNC(O)$alkyl, $R_aS$—, $R_aS(O)$—, $R_aSO_2$—, $R_aS$-alkyl-, $R_a(O)S$alkyl-, $R_aSO_2$alkyl-, $R_aOC(O)$—, $R_aOC(O)$alkyl-, $R_aC(O)$— and $R_aC(O)$alkyl-, wherein each $R_k$ is independently optionally substituted at each occurrence with at least 1, 2, or 3 substituents each of which is independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$;

$R_p$ is independently selected at each occurrence from the group consisting of hydrogen, alkenyl, alkyl, aryl, arylalkyl, cyanoalkyl, cycloalkenyl, cycloalkenylalkyl, cycloalkyl, cycloalkylalkyl, formylalkyl, haloalkyl, heteroaryl, heteroarylalkyl, heterocycle, heterocyclealkyl, and nitroalkyl, wherein each $R_p$ is independently optionally substituted at each occurrence with at least 1, 2, or 3 substituents each of which is independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_e$), -(alkyl)(NR$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$ and —C(O)NR$_c$R$_d$; and m is 0, 1, 2, 3, or 4.

A non-limiting example of a compound of this embodiment is N-[(3-{1-[(cyclobutyl)amino]-4-hydroxy-2-oxo-1,2-dihydro-quinolin-3-yl}-1,1-dioxo-1,4-dihydro-1$\lambda^6$-thieno [2,3-e][1,2,4] thiadiazin -7-yl)methyl]methanesulfonamide (compound I). As demonstrated below, compound I showed an unexpectedly improved pharmacokinetic profile as compared to compounds such as N-[(3-{1-[(cyclopropylmethyl) amino]-4-hydroxy-2-oxo-1,2-dihydroquinolin-3-yl}-1,1-dioxido-4H-thieno [2,3-e][1,2,4]thiadiazin-7-yl)methyl] methanesulfonamide (hereinafter "compound II") and N-{3-[1-(cyclobutylamino)-4-hydroxy-2-oxo-1,2-dihydroquinolin-3-yl]-1,1-dioxido-4H-1,2,4-benzothiadiazin -7-yl}methanesulfonamide (hereinafter "compound III"), where $R^1$ and $R^5$ are not cyclobutyl-N ($R_a$)— and $R_aSO_2N(R_f)$alkyl-, respectively, and in particular, $R^1$ and $R^5$ are not cyclobutyl-N(H)— and CH$_3$SO$_2$N(H)—CH$_2$—, respectively.

Compound I also exhibited an unexpectedly high potency in the inhibition of HCV RNA polymerase and HCV replication when compared to compounds such as 1-Benzyl-4-hydroxy-3-[7-(hydroxymethyl) 1,1-dioxido-4H-thieno[2,3-e] [1,2,4]thiadiazin-3-yl]quinolin-2(1H)-one, where $R^5$ is not $R_aSO_2N(R_f)$alkyl- (e.g., CH$_3$SO$_2$N(H)—CH$_2$—). For instance, compound I exhibited about 100-fold higher potency in the inhibition of HCV replication as compared to 1-Benzyl-4-hydroxy-3-[7-(hydroxymethyl)-1,1-dioxido -4H-thieno[2,3-e][1,2,4]thiadiazin-3-yl]quinolin-2(1H)-one.

The present invention also features pure or substantially pure compound I, or a pure or substantially pure pharmaceutically acceptable salt, stereoisomer or tautomer of compound I. As used herein, the term "substantially pure," when used in reference to a compound, refers to a preparation or composition where the preparation/composition contains more than 90% by weight of the compound, preferably more than 95% by weight of the compound, and more preferably more than 97% by weight of the compound The present invention further features pharmaceutical compositions comprising the compounds of the present invention or pharmaceutically acceptable salts thereof, and a pharmaceutically acceptable carrier. Each pharmaceutical composition of the invention can include 1, 2, 3 or more compounds of the invention, or their respective pharmaceutically acceptable salts. Any compound described herein can be included in a pharmaceutical composition of the present invention, e.g., a compound having formula I or II.

In one embodiment, a pharmaceutical composition of the present invention comprises compound I or a pharmaceutically acceptable salt thereof, and a pharmaceutically acceptable carrier. In another embodiment, a pharmaceutical composition of the present invention comprises compound I or a pharmaceutically acceptable salt thereof, at least another compound of the present invention or a pharmaceutically acceptable salt thereof, and a pharmaceutically acceptable carrier.

A pharmaceutical composition of the present invention can further comprise one or more other therapeutic agents, Non-limiting examples of suitable therapeutic agents include immune modulators (such as interferon-alpha, pegylated-interferon-alpha, interferon-beta, interferon-gamma, cytokine, and vaccine (e.g., vaccine comprising an antigen and an adjuvant)), or antiviral agents (such as anti-HCV agents which inhibit the replication of HCV by inhibiting host cellular functions associated with viral replication or by targeting proteins of the viral genome, anti-HCV agents which treat or alleviate symptoms of HCV infection including cirrhosis and inflammation of liver, anti-HBV agents which treat patients for disease caused by hepatitis B (HBV) infection (e.g., L-deoxythymidine, adefovir, lamivudine, or tenofovir), and anti-HIV agent which treat patients for disease caused by human immunodeficiency virus (HIV) infection (e.g., ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20), and T-1249)). As a non-limiting example, a pharmaceutical composition of the present invention can comprise compound I or a pharmaceutically acceptable salt thereof, and one or more other therapeutic agents described above.

In one embodiment, a pharmaceutical composition of the present invention comprises a compound of the present invention (e.g., compound 1) or a pharmaceutically acceptable salt thereof, and one or more HCV protease inhibitors. Non-limiting examples of suitable HCV protease inhibitors include

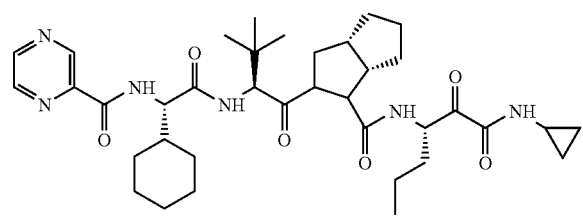

(hereinafter compound VX-950, Vertex Pharmaceuticals Inc.),

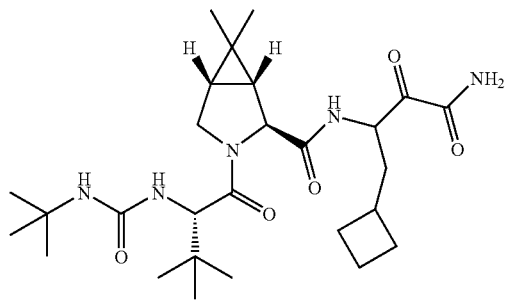

(hereinafter compound SCH503034, Schering-Plough Co.), and pharmaceutically acceptable salts thereof.

In another embodiment, a pharmaceutical composition of the invention comprises a compound of the present invention (e.g., compound I) or a pharmaceutically acceptable salt thereof, and one or more additional HCV polymerase inhibitors These additional polymerase inhibitors can be nucleoside or non-nucleoside inhibitors, such as

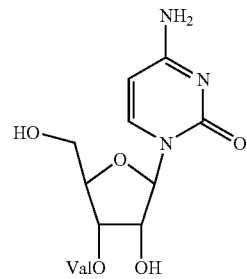

(hereinafter compound NM283, Idenix Pharmaceuticals, Inc.).

In still another embodiment, a pharmaceutical composition of the invention comprises a compound of the present invention (e.g., compound I) or a pharmaceutically acceptable salt thereof, and one or more HCV replication or translation inhibitors. Examples of these inhibitors include, but are not limited to, IRES inhibitors, antisense RNA, or siRNA In yet another embodiment, a pharmaceutical composition of the invention comprises a compound of the present invention (e.g., compound I) or a pharmaceutically acceptable salt thereof, and interferon. Non-limiting examples of interferons suitable for this purpose include interferon alpha 2a, interferon alpha 2b, consensus interferon alpha, and pegylated interferon In many instances, a pharmaceutical composition of this embodiment also includes 1-(β-D-ribofuranosyl)-1H-1,2,4-triazole-3-carboxamide (ribavirin).

In one example, a pharmaceutical composition of the present invention comprises compound I or a pharmaceutically acceptable salt thereof, and compound VX-950 or a pharmaceutically acceptable salt thereof. In another example, a pharmaceutical composition of the present invention comprises compound I or a or a pharmaceutically acceptable salt thereof, and compound SCH503034 or a pharmaceutically acceptable salt thereof.

The present invention further features methods of using the compounds or compositions of the present invention to treat or prevent infection caused by an RNA-containing virus (e.g., HCV). In one embodiment, these methods comprise administering to a patient in need of such treatment a therapeutically effective amount of a pharmaceutical composition of the present invention, thereby treating or preventing infection of the RNA-containing virus (e.g., HCV) in the patient. Any pharmaceutical composition described herein can be used for this purpose.

In another embodiment, these methods comprise administering to a patient in need of such treatment a therapeutically effective amount of a compound of the present invention or a pharmaceutically acceptable salt thereof, thereby treating or preventing infection of the RNA-containing virus (e.g., HCV) in the patient In one example, the methods comprise administering to a patient in need of such treatment a therapeutically effective amount of compound I or a pharmaceutically acceptable salt thereof, thereby treating or preventing infection of the RNA-containing virus (e.g., HCV) in the patient.

In still another embodiment, the methods comprise administering to a patient in need of such treatment a therapeutically effective amount of two or more compounds of the present invention or pharmaceutically acceptable salts thereof (e.g., compound I and another compound of the present invention, or pharmaceutically acceptable salts thereof), thereby treating or preventing infection of the RNA-containing virus (eg., HCV) in the patient.

In yet another embodiment, the methods comprise administering to a patient in need of such treatment a therapeutically effective amount of one or more compounds of the present invention (or pharmaceutically acceptable salt or salts thereof) and one or more other therapeutic agents, thereby treating or preventing infection of the RNA-containing virus (e.g., HCV) in the patient. Each of the other therapeutic agents can be independently selected from immune modulators (such as interferon-alpha, pegylated-interferon-alpha, interferon-beta, interferon-gamma, cytokine, and vaccine (e.g., vaccine comprising an antigen and an adjuvant)), or antiviral agents (such as anti-HCV agents which inhibit the replication of HCV by inhibiting host cellular functions associated with viral replication or by targeting proteins of the viral genome, anti-HCV agents which treat or alleviate symptoms of HCV infection including cirrhosis and inflammation of liver, anti-HBV agents which treat patients for disease caused by hepatitis B (HBV) infection (e.g., L-deoxythymidine, adefovir, lamivudine, or tenofovir), and anti-HfV agents which treat patients for disease caused by human immunodeficiency virus (HIV) infection (e.g., ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20), or T-1249)). A compound of the present invention and another therapeutic agent can be administered to a patient in need thereof either simultaneously or sequentially.

In one example, a method of the present invention comprises administering a therapeutically effective amount of compound I (or a pharmaceutically acceptable salt thereof) and an HCV protease inhibitor to a patient in need thereof, thereby treating or preventing HCV infection in the patient. Non-limiting examples of HCV protease inhibitors suitable for this purpose include compound VX-950, compound SCH503034, and pharmaceutically acceptable salts thereof.

In another example, a method of the present invention comprises administering a therapeutically effective amount of compound I (or a pharmaceutically acceptable salt thereof) and another HCV polymerase inhibitor to a patient in need thereof, thereby treating or preventing HCV infection in the patient. Non-limiting polymerase inhibitors suitable for this purpose include nucleoside or non-nucleoside inhibitors.

In yet another example, a method of the present invention comprises administering a therapeutically effective amount of compound I (or a pharmaceutically acceptable salt thereof) and an HCV replication or translation inhibitor to a patient in need thereof, thereby treating or preventing HCV infection in the patient. Non-limiting examples of HCV replication/translation inhibitors suitable for this purpose include, but are not limited to, IRES inhibitors, antisense RNA, or siRNA.

In still yet another example, a method of the present invention comprises administering a therapeutically effective amount of compound I (or a pharmaceutically acceptable salt thereof) and interferon (e.g., interferon alpha 2a, interferon alpha 2b, consensus interferon alpha, or pegylated interferon) to a patient in need thereof, thereby treating or preventing HCV infection in the patient.

In a further example, a method of the present invention comprises administering a therapeutically effective amount of compound I (or a pharmaceutically acceptable salt thereof), interferon (e.g., interferon alpha 2a, interferon alpha 2b, consensus interferon alpha, or pegylated interferon), and 1-(β-D-ribofuranosyl)-1H-1,2,4-triazole-3-carboxamide (ribavirin) to a patient in need thereof, thereby treating or preventing HCV infection in the patient.

The present invention also features methods of inhibiting the replication of an RNA-containing virus (e.g., HCV). The methods comprise contacting the virus, or cells infected by the virus, with an effective amount of a compound of the present invention or a pharmaceutically acceptable salty thereof, thereby inhibiting the replication of the virus. In one embodiment, the methods comprise contacting HCV virus with an effective amount of compound I or a pharmaceutically acceptable salt thereof, thereby inhibiting the replication of the virus. In another embodiment, the methods comprise contacting cells infected by HCV virus with an effective amount of compound I or a pharmaceutically acceptable salt thereof, thereby inhibiting the replication of the virus in the cells. In yet another embodiment, the methods comprise contacting HCV virus with an effective amount of two or more compounds of the present invention or pharmaceutically acceptable salts thereof (e.g., compound I and at least another compound of the present invention, or pharmaceutically acceptable salts thereof), thereby inhibiting the replication of the virus. In still yet another embodiment, the methods comprise contacting cells infected by HCV virus with an effective amount of two or more compounds of the present invention or pharmaceutically acceptable salts thereof (e.g., compound I and at least another compound of the present invention, or pharmaceutically acceptable salts thereof), thereby inhibiting the replication of the virus in the cells. In still another embodiment, the methods comprise contacting HCV virus with an effective amount of compound I and an HCV protease inhibitor (e.g., VX-950 or SCH503034), thereby inhibiting the replication of the virus, In yet another embodiment, the methods comprise contacting cells infected by HCV virus with an effective amount of compound I and an HCV protease inhibitor (e.g , VX-950 or SCH503034), thereby inhibiting the replication of the virus in the cells In a further embodiment, the methods comprise contacting HCV virus with an effective amount of compound I and another HCV polymerase inhibitor (e.g., a nucleoside or non-nucleoside inhibitor), thereby inhibiting the replication of the virus. In another embodiment, the methods comprise contacting cells infected by HCV virus with an effective amount of compound I and another HCV polymerase inhibitor (e.g., a nucleoside or non-nucleoside inhibitor), thereby inhibiting the replication of the virus in the cells. In still another embodiment, the methods comprise contacting HCV virus with an effective amount of compound I and an HCV replication or translation inhibitor (e.g., IRES inhibitors, antisense RNA, or siRNA), thereby inhibiting the replication of the virus. In still yet another embodiment, the methods comprise contacting cells infected by HCV virus with an effective amount of compound I and an HCV replication or translation inhibitor (e.g., IRES inhibitors, antisense RNA, or siRNA), thereby inhibiting the replication of the virus in the cells. In another embodiment, the methods comprise contacting HCV virus with an effective amount of compound I and interferon (e.g., interferon alpha 2a, interferon alpha 2b, consensus interferon alpha, or pegylated interferon), thereby inhibiting the replication of the virus. In still another embodiment, the methods comprise contacting cells infected by HCV virus with an effective amount of compound I and interferon (e.g., interferon alpha 2a, interferon alpha 2b, consensus interferon alpha, or pegylated interferon), thereby inhibiting the replication of the virus in the cells. In yet another embodiment, the methods comprise contacting HCV virus with an effective amount of compound I, interferon, and 1-(β-D-ribofuranosyl)-1H-1,2,4-triazole-3-carboxamide (ribavirin), thereby inhibiting the replication of the virus. In still a further embodiment, the methods comprise contacting cells infected by HCV virus with an effective amount of compound I, interferon, and 1(β-D-ribofuranosyl)-1H-1,2,4-triazole-3-carboxamide (ribavirin), thereby inhibiting the replication of the virus in the cells.

As used herein, "inhibiting" means abolishing or significantly reducing the original activity For instance, a compound of the present invention inhibits the replication of HCV if the compound can reduce the level or activity of HCV replication by at least 10%, 20%, 30%, 40%, 50%, 60%, 70%, 80%, 90%, 95% or more.

The present invention also features methods of inhibiting HCV RNA polymerase. The methods comprise contacting HCV RNA polymerase with an effective amount of a compound of the present invention or a pharmaceutically acceptable salty thereof, thereby inhibiting the activity of the HCV RNA polymerase. In one embodiment, the methods comprise contacting HCV RNA polymerase with an effective amount of compound I or a pharmaceutically acceptable salt thereof, thereby inhibiting the activity of the HCV RNA polymerase. In another embodiment, the methods comprise contacting HCV RNA polymerase with an effective amount of two or more compounds of the present invention or pharmaceutically acceptable salts thereof (e.g., compound I and at least another compound of the present invention, or pharmaceutically acceptable salts thereof), thereby inhibiting the activity of the HCV RNA polymerase.

The present invention further features use of a compound of the present invention, or a pharmaceutically acceptable salt thereof, to prepare a medicament for treating or preventing infection caused by an RNA-containing virus (e.g., HCV) in a patient. In one embodiment, the present invention provides the use of compound I or a pharmaceutically acceptable salt thereof, to prepare a medicament for treating or preventing HCV infection. In another embodiment, the present invention provides the use of compound I and at least another compound of the present invention, or pharmaceutically acceptable salts thereof, to prepare a medicament for treating or preventing HCV infection.

In still another embodiment, the present invention provides the use of one or more compounds of the present invention or pharmaceutically acceptable salt(s) thereof, and one or more other therapeutic agents, to prepare a medicament for treating or preventing viral infection (e.g., HCV infection). In many examples, the compound(s) employed in this embodiment includes compound I, and each of the other therapeutic agents is independently selected from immune modulators (such as interferon-alpha, pegylated-interferon-alpha, interferon-beta, interferon-gamma, cytokine, or vaccine (e.g., vaccine comprising an antigen and an adjuvant)), or antiviral agents (such as anti-HCV agents which inhibit the replication of HCV by inhibiting host cellular functions associated with viral replication or by targeting proteins of the viral genome, anti-HCV agent which treat or alleviate symptoms of HCV infection including cirrhosis and inflammation of liver, anti-HBV agents which treat patients for disease caused by hepatitis B (HBV) infection (e.g., L-deoxythymidine, adefovir, lamivudine, or tenofovir), or anti-HIV agents which treat patients for disease caused by human immunodeficiency virus (HIV) infection (e.g., ritonavir, lopinavir, indinavir, neifinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20), or T-1249)).

In one example, the present invention provides the use of compound I (or a pharmaceutically acceptable salt thereof) and an HCV protease inhibitor, to prepare a medicament for treating or preventing HCV infection. Non-limiting examples of HCV protease inhibitors suitable for this purpose include compound VX-950, compound SCH503034, and pharmaceutically acceptable salts thereof In another example, the present invention provides the use of compound I (or a pharmaceutically acceptable salt thereof) and another HCV polymerase inhibitor, to prepare a medicament for treating or preventing HCV infection. Non-limiting polymerase inhibitors suitable for this purpose include nucleoside or non-nucleoside inhibitors.

In yet another example, the present invention provides the use of compound I (or a pharmaceutically acceptable salt thereof) and an HCV replication or translation inhibitor, to prepare a medicament for treating or preventing HCV infection. Non-limiting examples of HCV replication/translation inhibitors suitable for this purpose include, but are not limited to, IRES inhibitors, antisense RNA, or siRNA.

In still yet another example, the present invention provides the use of compound I (or a pharmaceutically acceptable salt thereof) and interferon, to prepare a medicament for treating or preventing HCV infection. Non-limiting examples of interferon suitable for this purpose include interferon alpha 2a, interferon alpha 2b, consensus interferon alpha, and pegylated interferon In a further example, the present invention provides the use of compound I (or a pharmaceutically acceptable salt thereof), interferon and 1-(β-D-ribofuranosyl)-1H-1,2,4-triazole-3-carboxamide (ribavirin), to prepare a medicament for treating or preventing HCV infection.

The present invention also features processes for the preparation of the compounds of the invention. In one embodiment, the present invention provides a process for preparing a compound of formula (I) as described above, which process comprises:

(a) contacting a compound of formula (26)

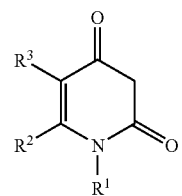

(26)

with carbon disulfide and a methylating agent in the presence of a base to provide a compound of formula (27)

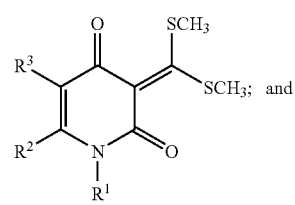

(27)

(b) contacting the compound of formula (27) with a compound of formula (13)

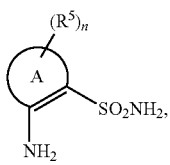

(13)

wherein A, $R^1$, $R^2$, $R^3$, and $R^5$ are as defined above.

In another embodiment, the present invention provides another process for preparing a compound of formula (I), which process comprises:

(a) contacting a compound of formula (26)

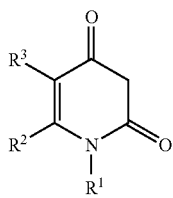

(26)

with tris(methylthio)methyl methyl sulfate or tris(methylthio)methyl methyl tetrafluoroborate in the presence of a base to provide a compound of formula (27)

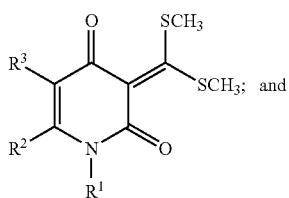

(27)

(b) contacting the compound of formula (27) with a compound of formula (13)

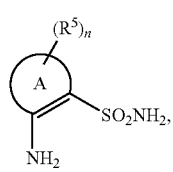

(13)

wherein A, $R^1$, $R^2$, $R^3$, $R^5$ and n are as defined above.

In some embodiments of the above processes, the compound of formula (13) is 2-amino-4-(methanesulfonyl-amino-methyl)-thiophene-3-sulfonic acid amide:

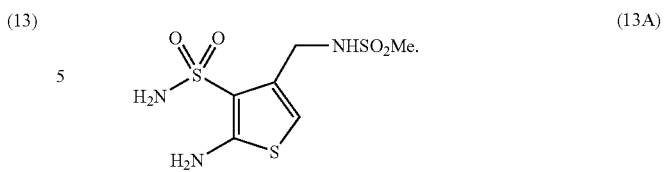

(13A)

In another embodiment, the present invention provides a process for preparing a compound of formula (13A). The process comprises:

(a) reacting compound of formula (A) with an agent selected from the group consisting of (1) isopropyl magnesium chloride, (2) isopropyl magnesium bromide, and (3) magnesium metal to obtain a compound of formula (B) in which X is selected from the group consisting of chloro and bromo:

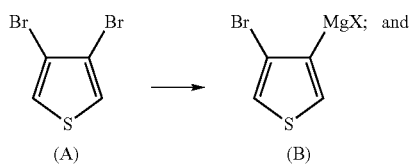

(b) reacting the compound of formula (B) with 4-methyl-benzenesulfonyl cyanide (also known as TsCN or TosCN) or ClC(O)O-alkyl to obtain a compound of formula (C) in which E is CN or C(O)O-alkyl (depending on whether TosCN or C(O)O-alkyl is used):

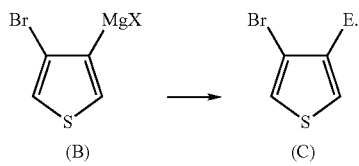

In some embodiments of the process for preparing compound of formula (13A), compound (C) is prepared as described in Example 2A (Part A), In other embodiments, compound (C) is prepared as described in Example 2B (Part A).

The compounds of the invention can comprise asymmetrically substituted carbon atoms, As a result, all stereoisomers of the compounds of the invention are meant to be included in the invention, including racemic mixtures, mixtures of diastereomers, mixtures of enantiomers, as well as individual optical isomers, including, enantiomers and single diastereomers of the compounds of the invention substantially free from other enantiomers or diastereomers. By "substantially free" is meant greater than about 80% free of other enantiomers or diastereomers of the compound, more preferably greater than about 90% free of other enantiomers or diastereomers of the compound, even more preferably greater than about 95% free of other enantiomers or diastereomers of the compound, even more highly preferably greater than about 98% free of other enantiomers or diastereomers of the compound and most preferably greater than about 99% free of other enantiomers or diastereomers of the compound.

In addition, compounds comprising the possible geometric isomers of carbon-carbon double bonds and carbon-nitrogen double are also meant to be included in this invention.

Individual stereoisomers of the compounds of this invention can be prepared by any suitable methods as appreciated by one of ordinary skill in the art. These methods include stereospecific synthesis, chromatographic separation of diastereomers, chromatographic resolution of enantiomers, conversion of enantiomers in an enantiomeric mixture to diastereomers and then chromatographically separating the diastereomers and regeneration of the individual enantiomers, enzymatic resolution and the like.

Stereospecific synthesis involves the use of appropriate chiral starting materials and synthetic reactions, which do not cause racemization, or inversion of stereochemistry at the chiral centers.

Diastereomeric mixtures of compounds resulting from a synthetic reaction can often be separated by chromatographic techniques that are well known to those of ordinary skill in the art Chromatographic resolution of enantiomers can be accomplished on chiral chromatography resins. Chromatography columns containing chiral resins are commercially available. In practice, the racemate may be placed in solution and loaded onto the column containing the chiral stationary phase. The enantiomers are then separated by HPLC.

Resolution of enantiomers can also be accomplished by converting the enantiomers in the mixture to diastereomers by reaction with chiral auxiliaries. The resulting diastereomers can then be separated by column chromatography. This technique is especially useful when the compounds to be separated contain a carboxyl, amino or hydroxyl group that will form a salt or covalent bond with the chiral auxiliary. Chirally pure amino acids, organic carboxylic acids or organosulfonic acids are especially useful as chiral auxiliaries. Once the diastereomers have been separated by chromatography, the individual enantiomers can be regenerated. Frequently, the chiral auxiliary can be recovered and used again.

Enzymes, such as esterases, phosphatases and lipases, can be useful for resolution of derivatives of the enantiomers in an enantiomeric mixture. For example, an ester derivative of a carboxyl group in the compounds to be separated can be prepared. Certain enzymes will selectively hydrolyze only one of the enantiomers in the mixture. Then the resulting enantiomerically pure acid can be separated from the unhydrolyzed ester.

The present compounds may exhibit the phenomena of tautomerism or structural isomerism. As the drawings/formulas within this specification can only represent one possible tautomeric or structural isomeric form, it should be understood that the invention encompasses any tautomeric or structural isomeric form, or mixtures thereof, which possess the ability to inhibit hepatitis C, and is not limited to any one tautomeric or structural isomeric form utilized within the drawings/formulas.

In addition, solvates and hydrates of the compounds of the invention are meant to be included in this invention When any variable (for example $R^1$, $R^2$, $R^3$, m, n, etc ) occurs more than one time in a substituent, compound or formula described herein, its definition on each occurrence is independent of its definition at every other occurrence. In addition, combinations of substituents are permissible if such combinations result in stable compounds Stable compounds can be isolated in a useful degree of purity from a reaction mixture.

The compounds of the present invention can exist as pharmaceutically acceptable salts. The term "pharmaceutically acceptable salt," as used herein, represents acid or base salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use The salts can be prepared during the final isolation and purification of the compounds or separately by reacting a basic group (for example, a nitrogen containing group) with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxy ethansulfonate, lactate, maleate, mesitylenesulfonate, methanesulfonate, naphthylenesulfonate, nicotinate, 2-naphthalenesulfonate, oxalate, pamoate, pectinate, persuifate, 3-phenylproprionate, picrate, pivalate, propionate, succinate, tartrate, trichloroacetate, tifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides.

Basic addition salts can be prepared during the final isolation and purification of the compounds by reacting an acidic group (for example, a carboxy group or an enol) with a suitable base such as the hydroxide, carbonate, or bicarbonate of a metal cation or with ammonia or an organic primary, secondary, or tertiary amine The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of basic addition salts include ethylenediamine, ethanolamine, diethanolamine, piperidine, and piperazine.

Preferred salts of the compounds of the present invention include monosodium, disodium, triethylamine salt, trifluoroacetate and hydrochloride.

The present compounds can also exist as pharmaceutically acceptable prodrugs. The term "pharmaceutically acceptable prodrug," refers to those prodrugs or zwitterions which are suitable for use in contact with the tissues of patients without undue toxicity, irritation, and allergic response, are commensurate with a reasonable benefitVrisk ratio, and are effective for their intended use. "Prodrugs" are considered to be covalently bonded carriers, which release the active parent drug of formula I or II in vivo when such prodrugs are administered to a mammalian subject. Prodrugs of the compounds of formula I or II (including but not limited to compound I) can be prepared by modifying functional groups present in the compounds in such a way that the modifications can be cleaved either during routine manipulation or in vivo. Prodrugs include compounds wherein hydroxy, amine, carboxy, or sulfhydryl groups are bonded to another group, which is cleavable when administered to a mammalian subject, thereby forming free hydroxyl, amino, carboxy, or sulfhydryl groups. Examples of prodrugs include, but are not limited to, acetate, formate, and benzoate derivatives of the hydroxy, carboxy and amine functional groups in the compounds of the present invention (e.g., the hydroxyl or amino groups in compound I).

A compound of the present invention can be administered alone or in combination with other antiviral or therapeutic agents. When using a compound, the specific pharmaceutically effective dose level for any particular patient will depend upon factors such as the disorder being treated and the severity of the disorder; the activity of the particular compound used; the specific composition employed; the age, body weight, general health, sex, and diet of the patient; the time of administration; the route of administration; the rate of excretion of the compound employed; the duration of treatment; and drugs used in combination with or coincidently with the compound used. The compounds can be administered orally, parenterally, osmotically (nasal sprays), rectally, vaginally, or topically in unit dosage formulations containing carriers, adjuvants, diluents, vehicles, or combinations thereof. The term "parenteral" includes infusion as well as subcutaneous, intravenous, intramuscular, and intrasternal injection.

Parenterally administered aqueous or oleaginous suspensions of the compounds can be formulated with dispersing, wetting, or suspending agents. The injectable preparation can also be an injectable solution or suspension in a diluent or solvent. Among the acceptable diluents or solvents employed are water, saline, Ringer's solution, buffers, monoglycerides, or diglycerides.

Transdermal patches can provide controlled delivery of the compounds. The rate of absorption can be slowed by using rate-controlling membranes Absorption enhancers can be used to increase absorption.

Solid dosage forms for oral administration include capsules, tablets, pills, powders, and granules, These solid dosage forms can optionally comprise diluents such as sucrose, lactose, starch, talc, silicic acid, aluminum hydroxide, calcium silicates, polyamide powder, tableting lubricants, and tableting aids such as magnesium stearate or microcrystalline cellulose. Capsules, tablets and pills can also comprise buffering agents, and tablets and pills can be prepared with enteric coatings or other release-controlling coatings Powders and sprays can also contain excipients such as talc, silicic acid, aluminum hydroxide, calcium silicate, polyamide powder, or mixtures thereof Sprays can additionally contain customary propellants such as chlorofluorohydrocarbons or substitutes therefore.

Liquid dosage forms for oral administration include emulsions, microemulsions, solutions, suspensions, syrups, and elixirs comprising inert diluents. These compositions can also comprise adjuvants such as wetting, emulsifying, suspending, sweetening, flavoring, and perfuming agents, Topical dosage forms include ointments, pastes, creams, lotions, gels, powders, solutions, sprays, inhalants, and transdermal patches. The compound is mixed under sterile conditions with a carrier and any needed preservatives or buffers. These dosage forms can also include excipients such as cellulose derivatives, polyethylene glycols, silicones, bentonites, silicic acid, or mixtures thereof. Suppositories for rectal or vaginal administration can be prepared by mixing the compounds with a suitable non-irritating excipient such as cocoa butter or polyethylene glycol, each of which is solid at ordinary temperature but fluid in the rectum or vagina. Ophthalmic formulations comprising eye drops, eye ointments, powders, and solutions are also contemplated as being within the scope of this invention.

The compounds of the invention can inhibit HCV RNA-dependent RNA polymerase, an enzyme essential for HCV viral replication. They can be administered as the sole active pharmaceutical agent, or used in combination with one or more other agents to treat hepatitis C infections or the symptoms associated with HCV infection. Other agents to be administered in combination with a compound of the present invention include drugs that can suppress HCV viral replication by direct or indirect mechanisms. These drugs include, but are not limited to, host immune modulators, for example, interferon-alpha, pegylated intei feion-alpha, CpG oligonucleotides and the like, or antiviral compounds that inhibit host cellular functions such as inosine monophosphate dehydrogenase, for example, ribavirin and the like. Also included are cytokines that modulate immune function Also included are vaccines comprising HCV antigens or antigen adjuvant combinations directed against HCV. Also included are agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7 and the like, Other agents to be administered in combination with a compound of the present invention include any agent or combination of agents that inhibit the replication of HCV by targeting proteins of the viral genome involved in the viral replication. These agents include but are not limited to other inhibitors of HCV RNA-dependent RNA polymerase such as, for example, nucleoside type polymerase inhibitors described in WO0190121(A2), or U.S. Pat. No. 6,348,587B1 or WO0160315 or WO0132153 or non-nucleoside inhibitors such as, for example, benzimidazole polymerase inhibitors described in EP1162196A1 or WO0204425 or inhibitors of HCV protease such as, for example, peptidomimetic type inhibitors such as BILN2061 and the like or inhibitors of HCV helicase.

Other agents to be administered in combination with a compound of the present invention include any agent or combination of agents that inhibit the replication of other viruses for co-infected individuals. These agent include but are not limited to therapies for disease caused by hepatitis B (HBV) infection such as, for example, adefovir, lamivudine, LdT (L-deoxythymidine) and tenofovir or therapies for disease caused by human immunodeficiency virus (HIV) infection such as, for example, protease inhibitors: ritonavir, lopinavir, indinavir, nelfinavir, saquinavir, amprenavir, atazanavir, tipranavir, TMC-114, fosamprenavir; reverse transcriptase inhibitors: zidovudine, lamivudine, didanosine, stavudine, tenofovir, zalcitabine, abacavir, efavirenz, nevirapine, delavirdine, TMC-125; integrase inhibitors: L-870812, S-1360, or entry inhibitors: enfuvirtide (T-20), T-1249.

Other agents to be administered in combination with a compound of the present invention include any agent or combination of agents that treat or alleviate symptoms of HCV infection including cirrhosis and inflammation of the liver.

When administered as a combination, the therapeutic agents can be formulated as separate compositions, which are given at the same time or within a predetermined period of time, or the therapeutic agents can be given as a single unit dosage form.

The total daily dose of a compound administered to a host in single or divided doses can be, without limitation, in the amount of from about 0.001 to about 100 mg/kg body weight. Single dose compositions can contain these amounts or submultiples thereof to make up the daily dose.

The biological activities of the compounds of the invention (e.g., compound I) can be evaluated using the methods described in U.S. patent application Ser. No. 10/699,513, now U.S. Patent Application Publication No. 20040167123, which is incorporated herein by reference in its entirety For instance, the 50% inhibitory concentration ($IC_{50}$) of an HCV polymerase inhibitor can be evaluated according to the following biochemical HCV polymerase inhibition assays. Either two-fold serial dilutions (fractional inhibition assay) or a narrower range of dilutions spanning the $IC_{50}$ (tight binding assay) of the inhibitors are incubated with 20 mM Tris—Cl pH 7.5, 5 mM $MgCl_2$, 50 mM NaCl, 1 mM dithiothreitol, 1 mM ethylene diamine tetraacetic acid (EDTA), 300 µM GTP, and 150 to 300 nM NS5B (HCV Strain 1B (J4, GenBank accession number AF054247, or H77, GenBank accession number AF011751)) for 15 minutes at room temperature, The reaction can be initiated by the addition of 20 µM CTP, 20 µl ATP, 1 µM 3H-UTP (10 mCi/µmol), 150 nM template RNA (see and 0.4 U/µl RNase inhibitor (RNasin, Promega), and allowed to proceed for 2 to 4 hours at room temperature. Reaction volume is 50 µl The reaction is terminated by the addition of 1 volume of 4 mM spermine in 10 mM Tris—Cl pH 8.0, 1 mM EDTA. After incubation for at least 15 minutes at room temperature, the precipitated RNA is captured by filtering through a GF/B filter (Millipore) in a 96 well format. The filter plate is washed three times with 200 µl each of 2 mM spermine, 10 mM Tris-Cl pH 8.0, 1 mM EDTA, and 2 times with ethanol. After air drying, 30 µl of Microscint 20 scintillation cocktail (Packard) is added to each well, and the retained cpm is determined by scintillation counting. $IC_{50}$ values are calculated by a two-variable nonlinear regression equation using an uninhibited control and a fully inhibited control sample to determine the minimum and maximum for the curve. Tight-binding assays are performed on those compounds exhibiting $IC_{50}$ values less than 0.15 µM in the fractional inhibition assay in order to more precisely measure the $IC_{50}$ values. Retained cpm are plotted vs. inhibitor concentration and fit to equation 1 using non-linear regression (Morrison and Stone, COMMENTS MOL. CELL. BIOPHYS., 2: 347-368 (1985)) to obtain the $IC_{50}$ values.

$$\text{Retained cpm}=A[\text{sqrt}\{(IC_{50}+I_t-E_t)^2+4IC_{50}E_t\}-(IC_{50}+I_t-E_t)] \quad \text{equation 1}$$

where $A=V_{max}[S]/2(K_m+[S])$; $I_t$=total inhibitor concentration and $E_t$=total active concentration of enzyme. The sequence of the template RNA is identical to the sequence described in paragraph 847 of U.S. Patent Application Publication No. 20040167123.

The 50% inhibitory concentration of an HCV inhibitor ($EC_{50}$) can also be evaluated using HCV replicon assays as described in Ikeda et al., J. VIROL., 76: 2997-3006 (2002), and Blight et al, SCIENCE, 290:1972-1974 (2000), with the following modifications. Replicon cells are plated at $3\times10^3$ cells per well in 96-well plate in DMEM medium containing 5% fetal calf serum. At day 1, culture medium is removed and replaced with fresh medium containing eight serial 2-fold dilutions of the compound of interest. The final concentration of DMSO in medium is 0.5%, The untreated control culture is treated in an identical manner except no inhibitor is added to the medium. Plates are incubated in a $CO_2$ incubator at 37° C. On Day 4, 100 µl lysis buffer (RTL) (Qiagen) is added to each well after removal of culture medium. RNA is purified according to manufacturer's recommendations (Qiagen RNAeasy) and eluted in 200 µl of water. The HCV RNA level is quantified from a portion (5 µl out of 200 µ) of the purified RNA by real-time RT-PCR method. The primers and probe are derived from specific sequence in the 5'UTR region. RT-PCR reaction is performed at 48° C. for 30 min, followed by 40 cycles set to 95° C., 15 s; 54° C., 30 s; and 72° C., 40 s. The percentage reduction of HCV RNA in the presence of compound is calculated and the 50% inhibitory concentration ($EC_{50}$) is calculated by non-linear regression analysis using the Prism program.

When tested using the biochemical HCV polymerase inhibition assays, representative compounds of the present invention (including compound I) inhibited HCV polymerase IB with the 50% inhibitory concentrations in the range of from about 0.001 µM to about 50 µM. When tested using the HCV replicon assays, representative compounds of the present invention (including compound I) inhibited the replicon production with the 50% inhibitory concentrations in the range of from about 0.001 µM to about 50 µM.

The compounds of the invention are named by ACD/ChemSketch version 5.0 (developed by Advanced Chemistry Development, Inc., Toronto, ON, Canada) or are given names consistent with ACD nomenclature. As used hereinbelow, DMF refers to N,N-dimethyiformamide, DMSO refers to dimethylsulfoxide, and THF refers to tetrahydrofuran.

The compounds and processes of the present invention will be better understood in connection with the following synthetic schemes, which illustrate the methods by which the compounds of the invention may be prepared. Starting materials can be obtained from commercial sources or prepared by well-established literature methods known to those of ordinary skill in the art. The groups A, $R^1$, $R^2$, $R^3$, $R^4$, $R^5$, and n are as defined above unless otherwise noted below.

This invention is intended to encompass compounds having formula (I) when prepared by synthetic processes or by metabolic processes. Preparation of the compounds of the invention by metabolic processes includes those occurring in the human or animal body (in vivo) or processes occurring in vitro.

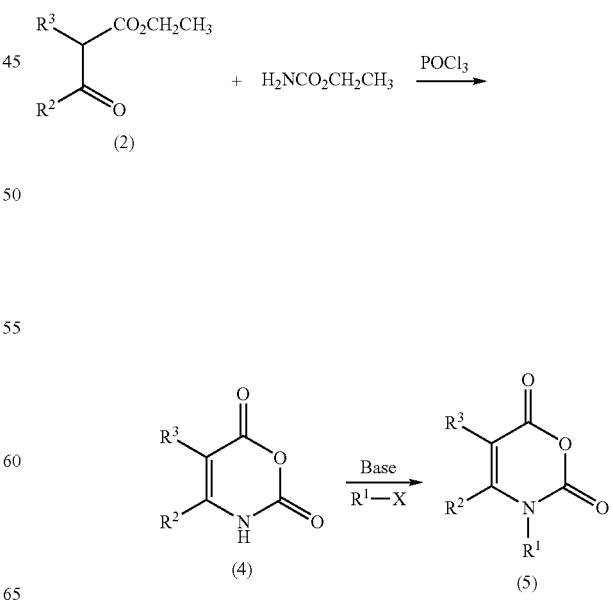

As shown in Scheme 1, compounds of formula (2) can be reacted with compounds of formula (3) in the presence of phosphorous oxychforide under heating conditions to provide compounds of formula (4). Compounds of formula (4) can be reacted with a base such as sodium hydride, potassium hydride, lithium hexamethyldisiiazide, and the like in solvent such as but not limited to dimethylacetamide, dimethylformamide, THF, and the like, followed by the addition of $R^1$-X, (wherein X is Br, Cl, I, $CF_3S(O)_2$—, $CH_3S(O)_2$—, or tosyl) to provide compounds of formula (5).

In addition, compounds of formula (9) can also be reacted with reagents including but not limited to phosgene, diphosgene, triphosgene, carbonyldiimidazole, ethyl chloroformate and the like in the presence of a base such as potassium hydroxide, pyridine, lithium hydroxide, and the like in solvents such as but not limited to water, toluene, benzene, and the like under heating conditions to provide compounds of formula (5).

Scheme 2

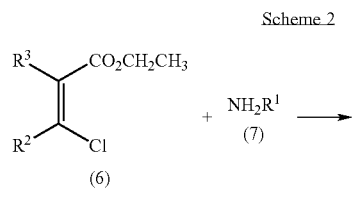

Scheme 4

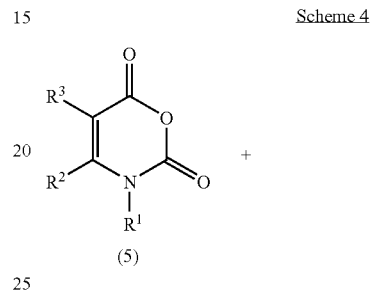

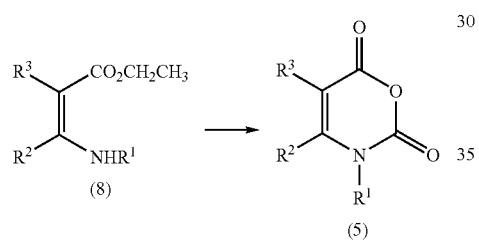

Alternatively, compounds of formula (6) can be treated with compounds of formula (7) under heating conditions optionally in the presence of a base such as potassium carbonate and a catalyst such as copper bromide, to provide compounds of formula (8). Compounds of formula (8) can be treated with reagents including but not limited to phosgene, diphosgene, triphosgene in solvents such as but not limited to 1,2-dichloroethane, carbon tetrachloride, 1,4-dioxane or mixtures thereof, under heating conditions to provide compounds of formula (5).

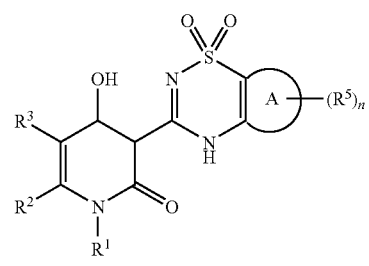

Scheme 3

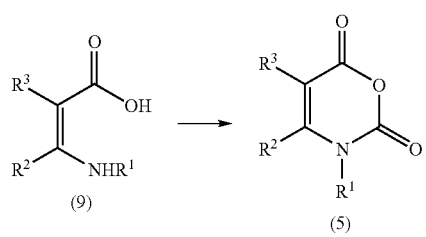

Compounds of formula (5) can be treated with compounds of formula (10) in the presence of a base such as sodium hydride, potassium hydride, lithium hexamethyldisilazide, and the like in a solvent such as but not limited to THF, diethyl ether, methyl tert-butyl ether followed by the treatment with an acid such as acetic acid, dichloroacetic acid or sulfuric acid to provide compounds of formula (11) which are representative of a compound of formula (I), where $R^4$ is hydroxy.

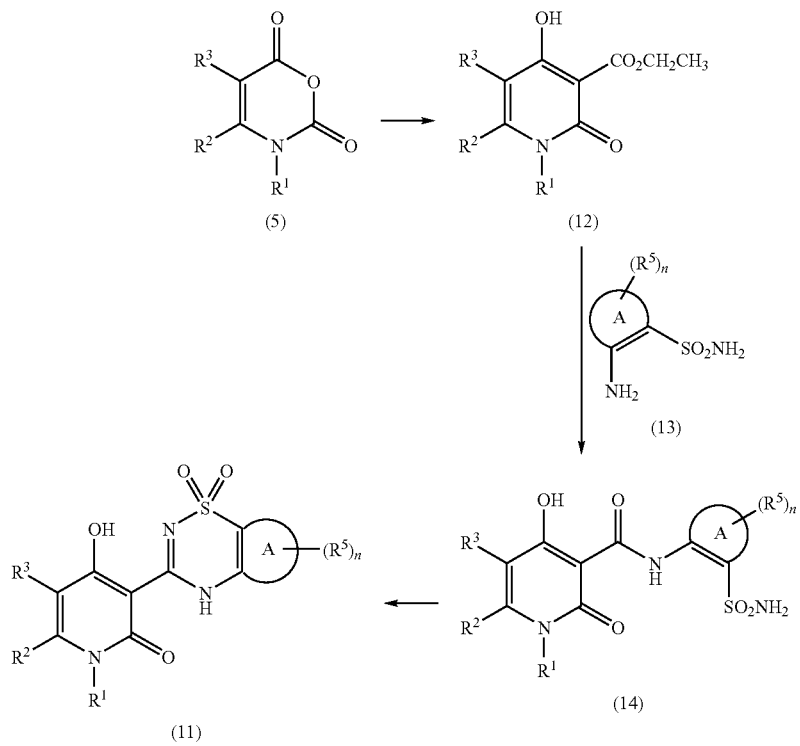

Scheme 5

Compounds of formula (5) can be reacted with diethyl malonate that has been pretreated with a base such as sodium hydride, potassium hydride, and the like in solvents such as dimethylacetamide, dimethylformamide, THF, and the like under heated conditions to provide compounds of formula (12). Compounds of formula (12) can be treated with compounds of formula (13) in solvents such as toluene, mesitylene, benzene, and the like under heated conditions to provide compounds of formula (14). Compounds of formula (14) can be treated with a base such as sodium hydroxide, potassium hydroxide, lithium hydroxide, and the like in water under heated conditions to provide compounds of formula (11).

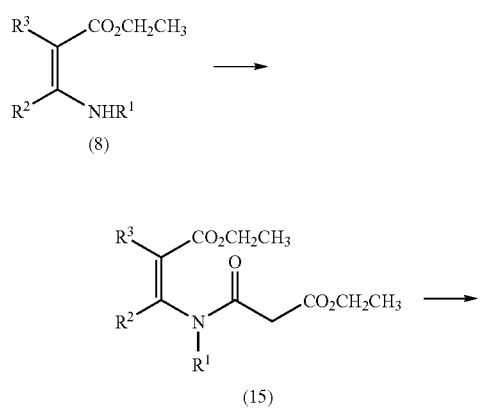

Scheme 6

-continued

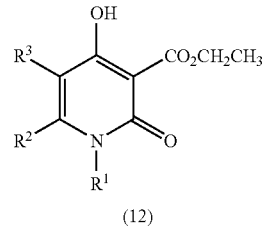

Alternatively, compounds of formula (8) can be treated with ethyl chloromalonate in the presence of a base such as triethylamine, diisopropylethylamine, pyridine, and the like in solvents such as dichloromethane, chloroform, carbon tetrachloride to provide compounds of formula (15). Alternatively, compounds of the formula (8) can be treated with ethyl chloromalonate in solvents such as benzene, toluene under heating conditions to provide compounds of formula (15). Compounds of formula (15) can be treated with sodium ethoxide in ethanoi to provide compounds of formula (12).

Scheme 7

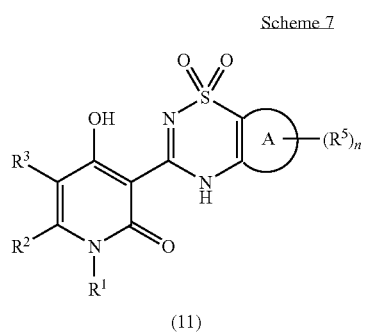

(11)

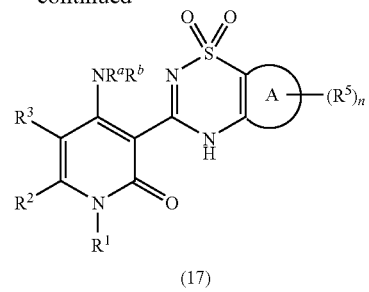

(I)

Scheme 7 shows the preparation of compounds of formula (I) where $R^4$ is halo. Compounds of formula (11) can be treated with reagents known to those skilled in the art, which are commonly used to convert alcohols to chlorides For example, compounds of formula (11) can be treated with reagents including but not limited to $PCl_5$, $PCl_3$, $POCl_3$, or thionyl chloride, with or without solvents such as but not limited to dichloromethane, chloroform and benzene, to provide compounds of formula (I) which are representative of compounds where $R^4$ is chlorine. Similar transformations are possible using $PBr_3$ or DAST to convert the said alcohol to the corresponding compound of formula (I) where $R^4$ is bromide and fluoride, respectively. Alternatively, compound of formula (I) wherein $R^4$ is iodo can be prepared by (a), reacting compound of formula (11) with a mesylating reagent such as methanesulfonyl chloride or methanesulfonyl anhydride in the presence of an amine base such as triethylamine, pyridine or diisopropylethylamine in solvents such as but not limited to dichloromethane, acetonitrile, carbon tetrachloride, chloroform, and (b) treatment of the mesylate thus formed with N-iodosuccinimide.

Scheme 8

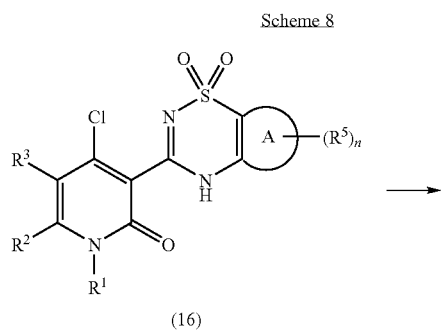

(16)

-continued (17)

As shown in Scheme 8, compounds of formula (16) can be converted to compounds of formula (17) which are representative of compounds of formula (I) where $R^4$ is $R_aR_bN$—, by treatment with an amine having the formula $R_aR_bNH$, (where $R_a$ and $R_b$ are as defined hereinabove) in a polar solvent such as methanol, ethanol, and the like, under heating conditions to provide compounds of formula (17)

Scheme 9

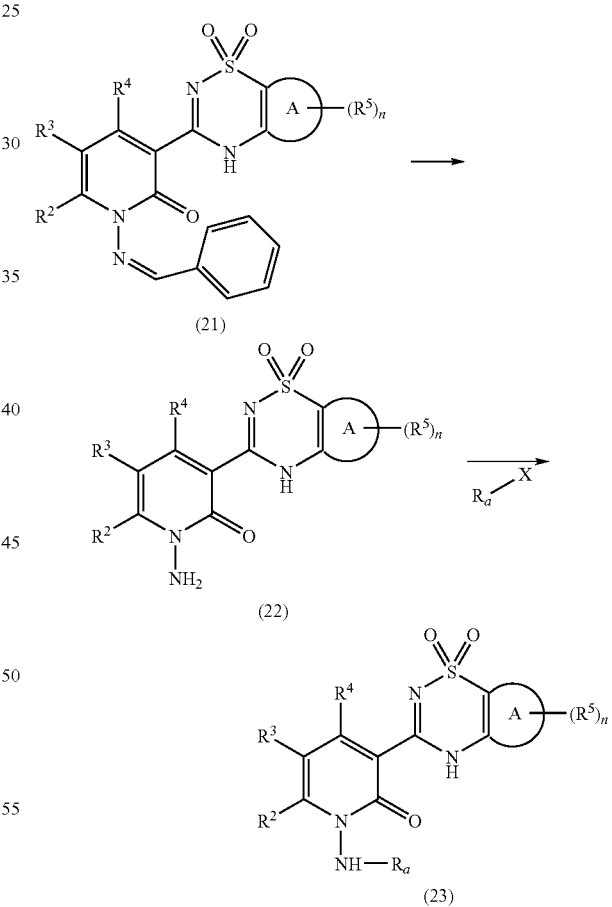

Compounds of formula (21) can be treated with aqueous base such as but not limited to potassium hydroxide, sodium hydroxide and the like, to provide compounds of formula (22) Compounds of formula (22) can be treated with a metal hydride base such as sodium hydride, an organolithium reagent (e.g. t-BuLi, n-BuLi, or s-BuLi), or lithium hexamethyldisilazide in an appropriate solvent or a mixture of solvents selected from THF, DMSO, DMF, dioxane, ether, dichloromethane, and the like, followed by the addition of RaX wherein X is Br, Cl, I, $CF_3S(O)_2$—, $CH_3S(O)_2$—, or tosyl to provide compounds of formula (23) which are representative of compounds of formula (I) wherein $R^1$ is —NHRa.

ylimidazole, 2-isopropylimidazole, 4-methylimidazole, 4-nitroimidazole, pyridine, N,N-dimethylaminopyridine, 1,2,4-triazole, pyrrole, 3-methylpyrrole, triethylamine, diisopropylethylamine or N-methylmorpholine and the like.

Compounds of formula (27) can be treated with compounds such as (13) in a solvent or a mixture of solvents, such as but not limited to, toluene, benzene, dioxane or tetrahydrofuran, and the like, at a temperature of about 50° C. to about 150° C. to provide compounds of formula (11).

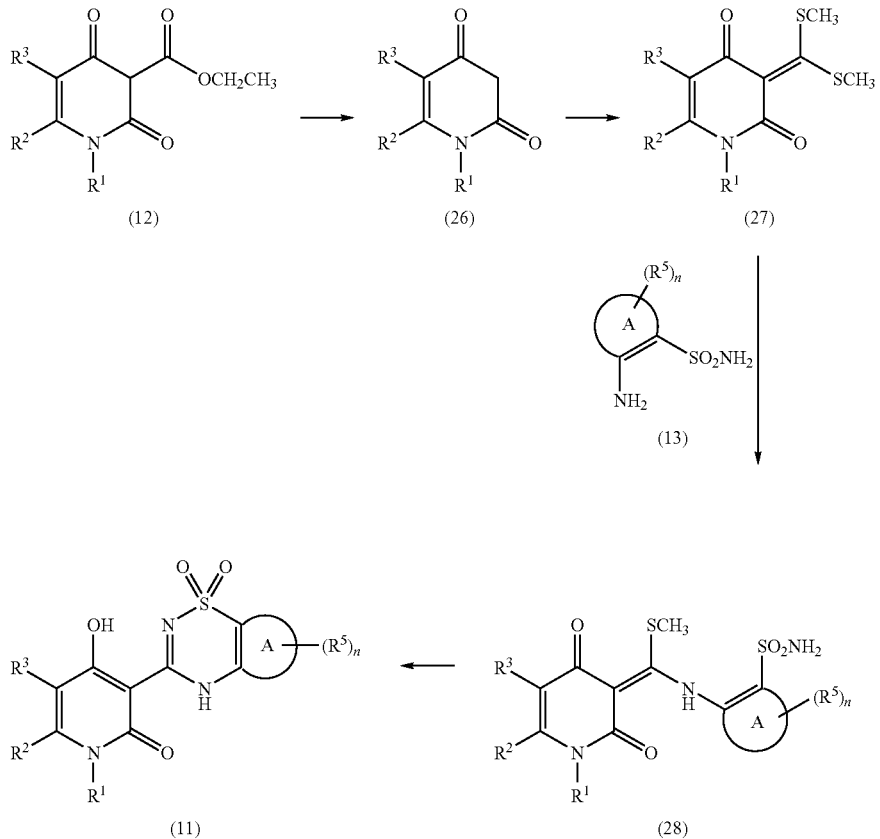

Compounds of formula (12) can be reacted with aqueous base solutions such as potassium hydroxide and the like under heated conditions to provide compounds of formula (26). Compounds of formula (26) can be reacted with a base in a solvent, or mixtures of solvents such as, but not limited to, N,N-dimethylformamide, tetrahydrofuran, diethyl ether, or methyl tert-butyl ether, and the like, followed by treatment with carbon disulfide at a temperature of about room temperature to about 70° C. Examples of the base include, but not limited to, sodium hydride, potassium hydride, lithium diisopropylamide, sodium hexamethyldisilazide and lithium hexamethyldisilazide. Subsequent treatment with a methylating reagent at a temperature of about 25° C. provides compounds of formula (27). Examples of the methylating agent include, but not limited to, methyl iodide, methyl triflate, dimethylsulfate, and the like, Alternatively, compounds of the formula (26) can be reacted with tris(methylthio)methyl methyl sulfate in the presence of a base in a solvent such as 1,4-dioxane or dimethylacetamide, and the like, at a temperature of about 25° C. to about 150° C. to give compounds of formula (27). Examples of the base include, but are not limited to, organic amine bases such as imidazole, 1-methylimidazole, 2-meth-

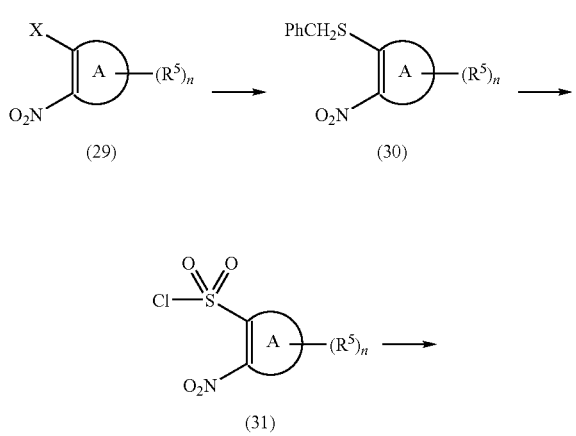

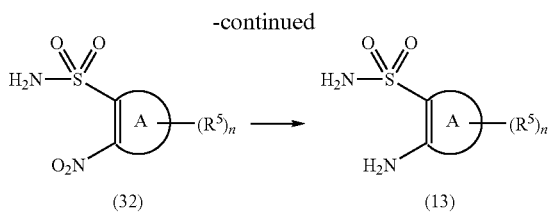

Compounds of the formula (29) wherein X is I, Br, Cl or F can be treated with alkyl thiols such as benzene methylthiol in the presence of a base such as sodium carbonate in solvents such as ethanol and the like under heated conditions to give compounds of the formula (30). Treatment of (30) with chlorine gas in hydrochloric acid or acetic acid provides compounds of the formula (31). Compounds of the formula (31) in solvents such as but not limited to dichloromethane, tetrahydrofuran or dioxane can be treated with ammonia or ammonium hydroxide to give compounds of the formula (32). Reduction of compounds of the formula (32) with iron powder and ammonium chloride in aqueous alcoholic solvents such as methanol or ethanol under heated conditions optionally with iron powder in acetic acid under heated conditions to provide compounds of the formula (13).

Compounds of formula (42) can be sulfonylated with a sulfonyl chloride of formula $R_aSO_2Cl$ in the presence of a base such as pyridine alone or an amine base such as triethylamine, diisopropylethylamine, and the like in a solvent or combination of solvents such as dichloromethane, tetrahydrofuran, or dioxane, to provide compounds of formula (46), Alternatively, compounds of formula (42) can be sulfamoylated in the presence of an amine base such as but not limited to triethylamine, or diisopropylethylamine, and the like, in a solvent or combination of solvents such as dichloromethane, tetrahydrofuran or dioxane, and the like, with compounds of formula (49) to give compounds of formula (47) Compounds of formula (49) can be obtained by treating chlorosulfonyl isocyanate and 2-chloroethanol in conditions that are well known in the art. Compounds of formula (47) can be treated further with an amine having the formula $R_aR_bNH$, (where $R_a$ and $R_b$ are as defined herein) in a solvent or combination of solvents such as dichloromethane, THF, or acetonitrile, and the like, under heating conditions to provide compounds of formula (48), Compounds of formula (42) can be sulfamoylated in the presence of an amine base such as triethylamine, or diisopropylethylamine, and the like, in a solvent or combination of solvents such as dichloromethane, tetrahydrofuran or dioxane, and the like, with compounds of formula (54) to give compounds of formula (48). Compounds of formula Scheme 12

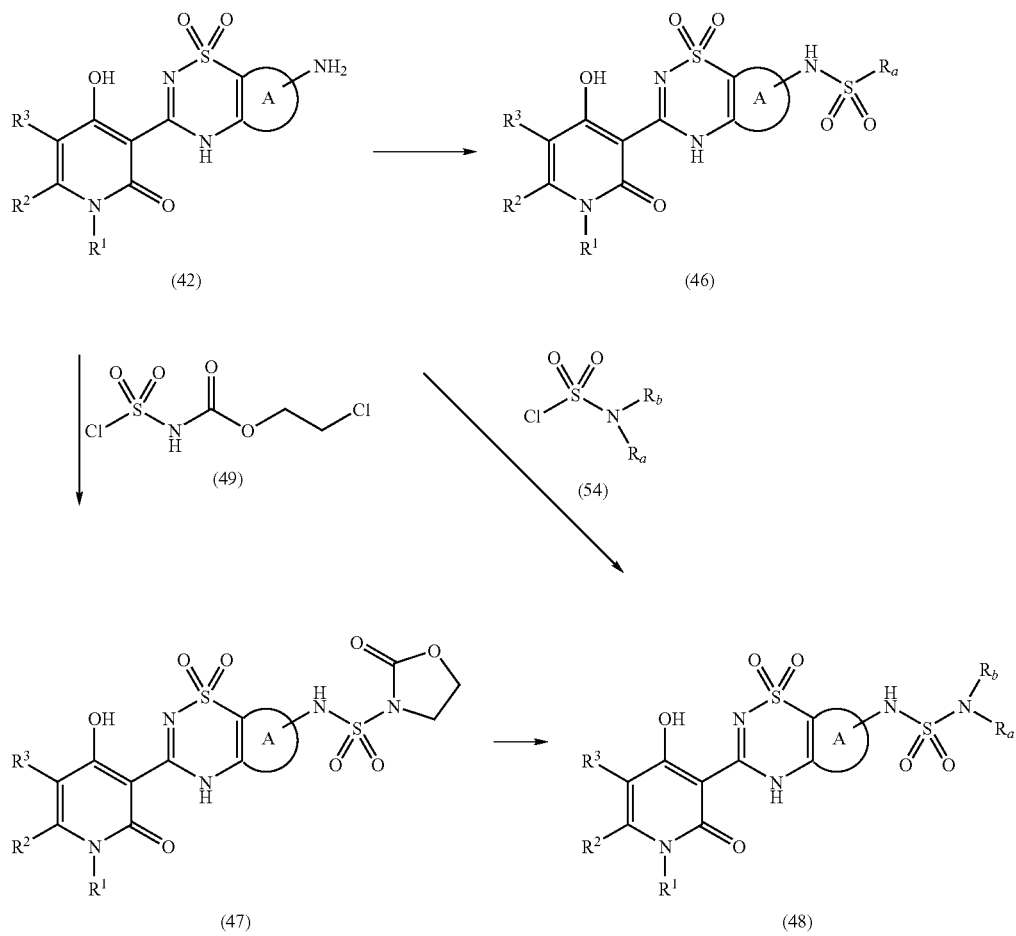

(54) can be obtained by treating an amine of the formula R$_a$R$_b$NH with sulfuryl chloride or by (a) treating an amine of the formula R$_a$R$_b$NH with chlorosulfonic acid, and (b) contacting the product of step (a) with a chlorinating agent such as phosphorous pentachloride and the like in conditions that are well known in the art.

Similarly, compounds of formula (11) wherein R$^5$ is -alkylNH$_2$ can be converted to compounds of formula (11) wherein R$^5$ is -alkylNHSO$_2$NR$_a$R$_b$ using the conditions for the transformation of compounds of formula (42) to compounds of formula (48). Compounds of formula (11) wherein R$^5$ is -alkylNH$_2$ can be converted to compounds of formula (11) wherein R$^5$ is -alkylNHSO$_2$R$_a$ can be achieved by employing the conditions for the transformation of compounds of formula (42) to compounds of formula (46)

triphenylphosphine, and the like, and diisopropylazodicarboxylate, 1,1'-(azadicarbonyl)piperidine, or diethylazodicarboxylate, and the like, in a solvent or combination of solvents such as dichloromethane or tetrahydrofuran to provide compounds of formula (52). Alternatively, compounds of formula (52) wherein R$_a$ is methyl can be obtained by methylating compounds of formula (51) with a methylating agent such as, but not limited to, methyl iodide, dimethyl sulfate, trimethysilyldiazomethane in conditions that are well known in the art. Transformation of compounds of formula (52) to compounds of formula (53) can be achieved by reaction with an acid such as trifluoroacetic acid or hydrochloric acid, or by hydrogenolysis conditions such as palladium on carbon under hydrogen gas.

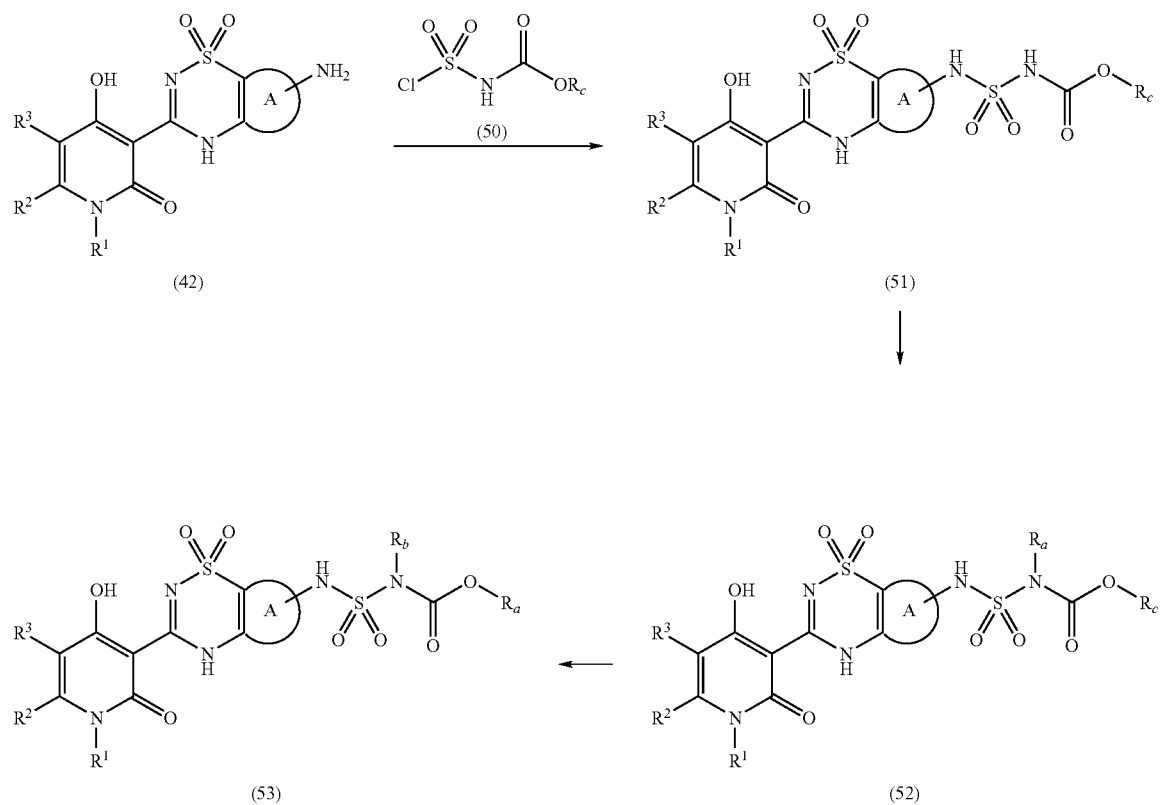

Scheme 13

Compounds of formula (42) can be sulfamoylated with a sulfamoyl chloride of formula R$_c$OC(O)NHSO$_2$Cl (50), in the presence of an amine base such as pyridine, triethylamine or diisopropylethylamine, and the like, in a solvent or combination of solvents such as dichloromethane, tetrahydrofuran, diethyl ether, benzene, or acetonitrile, and the like, to provide compounds of formula (51). Compounds of formula (50) can be prepared by treating an alcohol of formula R$_c$OH with chlorosulfonyl isocyanate in a solvent or combination of solvents such as dichloromethane, carbon tetrachloride, diethyl ether, benzene, or toluene, and the like. Compounds of formula (51) can be treated further with an alcohol having the formula R$_a$OH in the presence of tri-n-butylphosphine or Similarly, compounds of formula (11) wherein R$^5$ is -alkylN$_2$ can be converted to compounds of formula (11) wherein R$^5$ is -alkylNHSO$_2$NHCOOR$_c$ by the conditions for the transformation of compounds of formula (42) to compounds of formula (51).

Compounds of formula (11) wherein R$^5$ is -alkylNH$_2$ can be converted to compounds of formula (11) wherein R$^5$ is -alkylNHSO$_2$N(R$_a$)COOR$_c$ by the conditions employed for the conversion of (51) to (52).

Compounds of formula (11) wherein R$^5$ is -alkylNH$_2$ can be converted to compounds of formula (11) wherein R$^5$ is -alkylNHSO$_2$NR$_a$R$_b$ by the conditions employed for the conversion of (52) to (53).

It should be understood that the above-described embodiments and the following examples are given by way of illustration, not limitation. Various changes and modifications within the scope of the present invention will become apparent to those skilled in the art from the present description.

EXAMPLES

Example 1

Preparation of 1-Cyclobutylamino-4-hydroxy-1H-quinolin-2-one

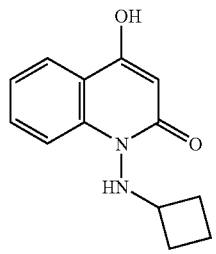

Part A. Preparation of 2-(N'-benzylidene-hydrazino)-benzoic acid.

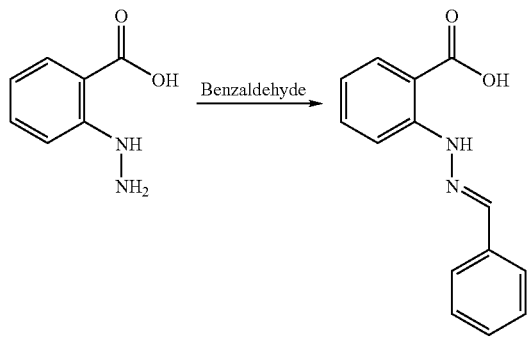

To a solution of 2-hydrazino-benzoic acid mono hydrochloric acid salt (13.66 g, 72.42 mmol) dissolved in water (580 mL) and ethanol (125 mL) was added a solution of benzaldehyde (7.35 mL, 72.42 mmol) in ethanol (20 mL) dropwise at room temperature. The reaction mixture was stirred at room temperature for an additional 3 hours. The resulting solid was collected by filtration and dried in a vacuum oven to provide 12.0 g (69%) of 2-(N'-benzylidene-hydrazino)-benzoic acid as a yellow solid.

Part B. Preparation of 2-(N'-benzylidene-hydrazino)-benzoic acid methyl ester.

Method A:

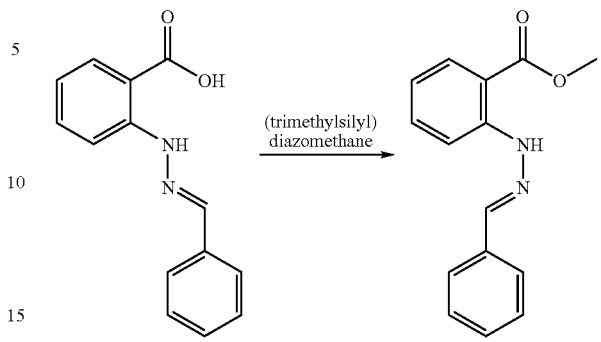

To a round-bottomed flask containing a solution of the product from Part A (12.0 g, 49.95 mmol) dissolved in a solution of methanol (60 mL) and tetrahydrofuran (60 mL) was affixed with an addition funnel to the top. The round-bottomed flask was then placed in an ice bath, and vented to a mineral oil bubbler. The addition funnel was then charged with a solution of (trimethylsilyl)diazomethane (2.0 M in diethyl ether, 50 mL, 100 mmol), which was added dropwise over 20 minutes to the flask. Upon complete addition the reaction mixture was capped and allowed to stir at room temperature for 16 hours. The resultant mixture was then concentrated under vacuum and subjected to column chromatography on silica gel using 2% ethyl acetate in hexanes as eluent to provide 11.0 g (87%) of 2-(N'-benzylidene-hydrazino)-benzoic acid methyl ester.

Method B:

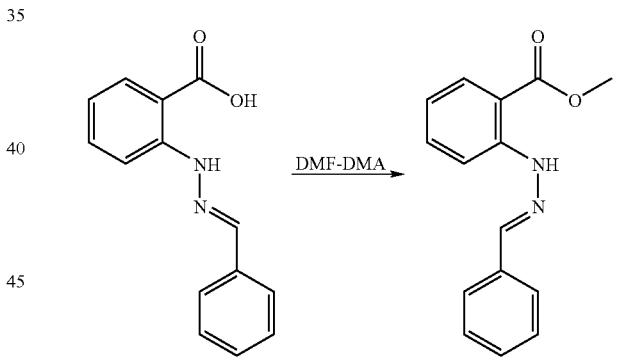

To a round-bottomed flask containing a solution of the product from Part A (12.0 g, 49.95 mmol) was added tetrahydrofuran (348 mL), followed by dimethylformamide dimethyl acetal (DMF-DMA, 13.2 mL, 99.9 mmol, 2 eq). The solution was heated to reflux for 10 hours. At completion of the reaction, solvent was switched to toluene (100 mL), washed with half-saturated NaCl solution (3×20 mL), saturated NaCl solution (20 mL). Solvent was removed under reduced pressure and product was crystallized from EtOAc/MeOH to provide 11.7 g (92%) of 2-(N'-benzylidene-hydrazino)-benzoic acid methyl ester. MP 66.5-67.5° C. $^1$H NMR (400 MHz, DMSO-$d_6$) δ ppm 3.87 (s, 3H), 6.83 (td, J=7.55, 1.10 Hz, 1H), 7.33-7.44 (m, 3H), 7.50-7.54 (m, 1H), 7.69-7.75 (m, 3H), 7.85 (dd, J= 8.03, 1.58 Hz, 1H), 8.19 (s, 1H), 11.00 (s, 1H). $^{13}$C NMR (100 MHz, DMSO-$d_6$)δ ppm 51.82 (CH$_3$), 108.71 (C), 112.96 (CH), 117.27 (CH), 125.79 (2×CH), 128.14 (2×CH), 128.29(CH), 130.11 (CH), 134.14 (CH), 134.49 (C), 140.64 (CH), 146.14 (C), 166.92 (C).

Part C. Preparation of 2-[N'-benzylidene-N-(2-methoxy-carbonyl-acetyl)-hydrazino]-benzoic acid methyl ester.

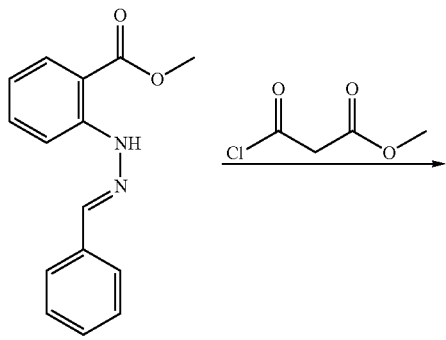

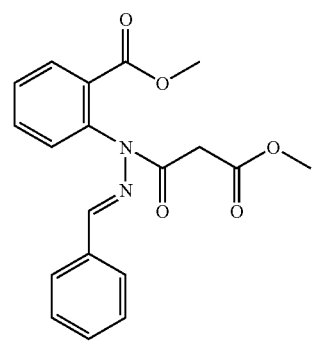

To the product from Part B (21.62 g, 89.99 mmol) dissolved in toluene (150 mL) was added methyl 3-chloro-3-oxopropionate (9.65 mL, 89.99 mmol). The mixture was then heated to reflux for 3 hours, allowed to cool to room temperature, the toluene solvent removed under vacuum and the resultant oil left under vacuum for 16 hours. The resulting solid formed was collected and washed with ether to provide 24.68 g (77%) of 2-[N'-benzylidene-N-(2-methoxycarbonyl-acetyl)-hydrazino]-benzoic acid methyl ester.

Part D. Preparation of 1-(benzylidene-amino)-2,4-dioxo-1,2,3,4-tetrahydro-quinoline-3-carboxyiic acid methyl ester.

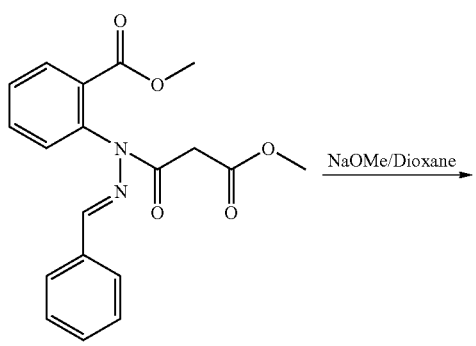

-continued

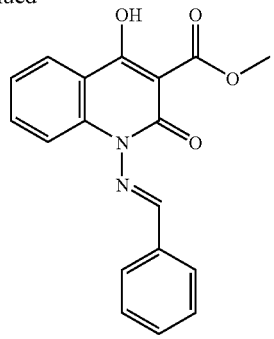

The product from Part C (20 g, 56.43 mmol) was suspended in a solution of sodium methoxide in methanol (0.5M, 112.9 mL, 56.43 mmol) and heated to 50° C. for 3 hours. The mixture was allowed to cool to room temperature, then poured into a solution of water (300 mL), which was then acidified to pH=1 with a 2N aqueous hydrochloric acid solution which caused a yellow solid to form. This solid was then collected by filtration and dried in a vacuum oven to provide 17 g (94%) of 1-(benzylidene-amino)-2,4-dioxo-1,2,3,4-tetrahydro-quinoline-3-carboxylic acid methyl ester as a yellow solid.

Part E. Preparation of 1-amino-4-hydroxy-1H-quinolin-2-one

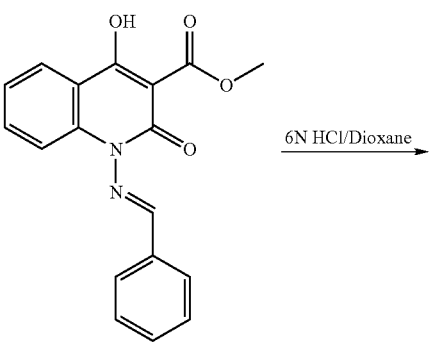

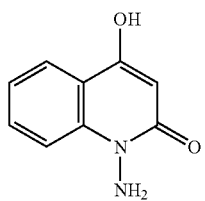

The product from Part D (14.4 g, 44.68 mmol) and potassium hydroxide (34.53 g, 616.55 mmol) were dissolved in a mixture of dioxane (60 mL) and water (200 mL), A short-path distillation column was attached and the solution heated to 115° C. in order to remove (distill off) the dioxane (60 mL) from the mixture The solution was then partially cooled and an additional 60 mL of dioxane added to the solution and distilled off. This was done 2 more times (4×60 mL dioxane total) and the resulting aqueous solution was extracted with a mixture of 1/1: EtOAc/Et₂0 (200 mL) and the to the resultant aqueous solution was added a solution of 12N HCl solution until the pH of the solution was 2, This caused a solid to form, which was collected and dried in a vacuum oven to provide 6.8 g (86%) of 1-amino-4-hydroxy-1H-quinolin-2-one as a yellow solid.

Part F. Preparation of 1-cyclobutylideneamino-4-hydroxy-1H-quinolin-2-one.

Method A:

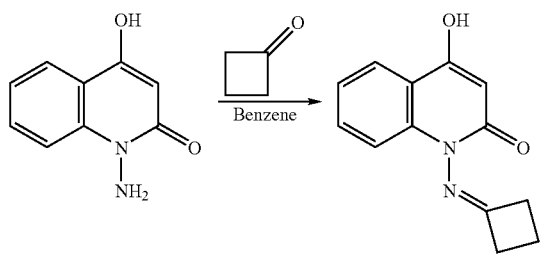

To a suspension of the product from Part E (5.6 g, 31.79 mmol, 1 eq) and trifluoroacetic acid (0.12 mL, 1.59 mmol) in benzene (55 mL) was added cyclobutanone (5.94 mL, 79.47 mmol, 2.5 eq) and a dean-stark tube attached. The mixture was then heated to reflux and over the next hour water was collected in the dean-stark tube The solution was cooled to room temperature, then an additional amount of cyclobutanone (2.38 mL, 31.79 mmol, 1.0 eq) was added and the mixture again heated to reflux for 30 min. After cooling again to room temperature, the mixture was concentrated under vacuum to provide 6.92 g (95%) of 1-cyclobutylideneamino-4-hydroxy-1H-quinolin-2-one as a light green solid.

Method B:

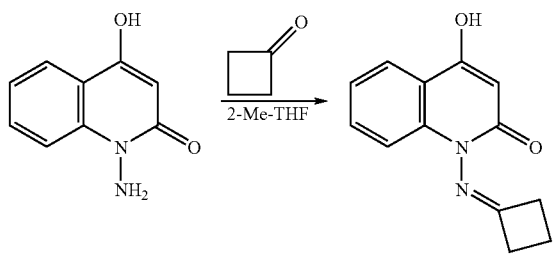

To a suspension of the product from Part E (10.6 g, 56.8 mmol, 94 wt % purity) and trichloroacetic acid (1.9 g, 11.4 mmol, 0.2 eq) in 2-methyltetrahydrofuran (113 mL) was added cyclobutanone (8.5 mL, 113.5 mmol, 2.0 eq). The reaction mixture was heated to reflux with a Dean-Stark trap attached. The suspension was heated to reflux and stirred under reflux for 16 h. The suspension was cooled to 5° C. and stirred for 1 h., The suspension was then filtered. The product was dried at 40° C. under vacuum for 12 h to give 11.3 g (93 wt % purity=81% wt-adjusted yield) of 1-cyclobutylideneamino-4-hydroxy-1H-quinolin-2-one as an off-white solid. $^1$H NMR [(CD$_3$)$_2$SO] δ 1.94 (2H, m), 2.68 (2H, m), 3.19 (2H, m), 5.89 (1H, s), 7.22 (1H, m), 7.35 (1H, dd), 7.56 (1H, m), 7.87 (1H, dd), 11.38 (1H, br s); $^{13}$C NMR [(CD$_3$)$_2$SO] δ 12.9, 34.2, 36.0, 97.8, 113.6, 114.7, 121.1, 122.5, 130.6, 137.4, 156.2, 159.8, 182.3. MS-ESI: m/z 229 (M+H)$^+$ and m/z 251 (M+Na)$^+$.

Part G. Preparation of 1-cyclobutylamino-4-hydroxy-1H-quinolin-2-one

Method A:

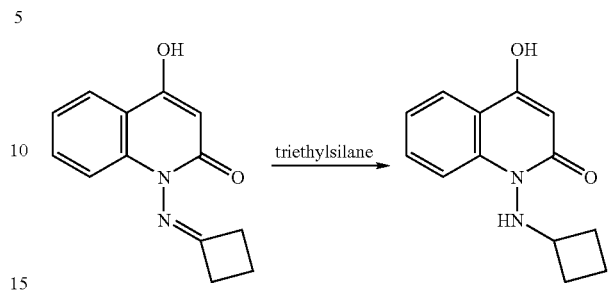

To the product from Part F (0.25 g, 1.096 mmol) dissolved in trifluoroacetic acid (3 mL) was added triethylsilane (0.368 mL, 2.30 mmol) and the mixture stirred at room temperature for 1 hour. To this mixture was added a solution of hexanes (10 mL), the mixture shaken and the trifluoroacetic acid layer separated and concentrated under high vacuum to yield 0.21 g (83%) of 1-cyclobutylamino-4-hydroxy-1H-quinolin-2-one as an oil.

Method B:

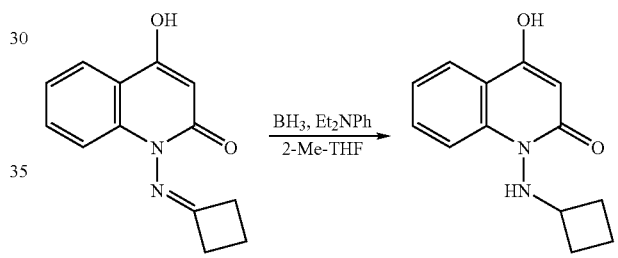

To a three-necked flask with the product from Part F were charged hydrazone (6.85 g, 30.0 mmol) and THF (102 ml), the resulting mixture was cooled to 15° C. To the mixture was added BH$_3$.Et$_2$NPh (4.2 g, 24.0 mmol) dropwise keeing the reaction temperature below 25° C. The resulting mixture was stirred at room temperature until less than 1% of starting material remains. Methanol (14 ml) was added slowly to quench the borane reagent. The resulting mixture was stirred at room temperature for 30 min. The organic solvents (MeOH and THF) were removed under vacuum to about 35 ml. MeOH (70 ml) was added and the resulting mixture was concentrated to about 35 ml. More MeOH (28 ml) was added to the mixture and the resulting mixture was heated to reflux (~65° C.), 2N HCl (170 ml) solution was then added slowly keeping the temperature above 60° C., The resulting mixture was heated to 80° C. for 1 h, cooled slowly to room temperature, stirred at room temperature for 2 h, and filtered. The mother liquor was circulated to rinse the flask. The wet cake was dried in a vacuum oven at 45° C. overnight to obtain 6.29 product (90%) of 1-cyclobutylamino-4-hydroxy-1H-quinolin-2-one as a white solid. $^1$H NMR [(CD$_3$)$_2$SO] δ1.50 (1H, m), 1.63 (1H, m), 1.96 (4H, m), 3.62 (1H, m), 5.91 (1H, s), 6.23 (1H, d), 7.17 (1H, m), 7.58 (1H, m), 7.82 (2H, m), 11.40 (1H, br s); $^{13}$C NMR [(CD$_3$)$_2$SO] δ14.5, 28.3, 54.5, 96.9, 113.9, 114.7, 120.5, 122.3, 130.4, 139.4, 160.0, 160.9.

Example 2A

Preparation of 2-Amino-4-(methanesulfonylaminomethyl)-thiophene-3-sulfonic acid amide (Method A).

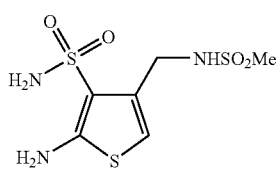

Part A. Preparation of 4-bromo-thiophene-3-carboxylic acid ethyl ester.

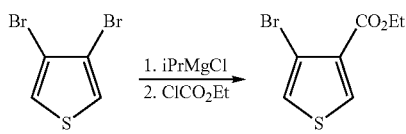

To a 0° C. solution of 3,4-dibromothiophene (1.0 Kg, 4.13 mol) in tetrahydrofuran (7.4 Kg) was added iPrMgCl (2.0 M solution in tetrahydrofuran, 2.58 Kg, 5.17 mol) keeping the temperature below 5° C. The resulting mixture was stirred at 0-5° C. for 5 hours. To the cooled Grignard solution was added ethyl chloroformate (896 g, 5.17 mol) dropwise keeping the temperature below 10° C. The resulting mixture was warmed to room temperature, and stirred for 16 hours. Water (200 mL) was added to the reaction mixture, and the resulting mixture was stirred at room temperature for 10 min The majority of the tetrahydrofuran was then removed under vacuum and ethyl acetate (4.5 Kg) was added to the mixture followed by 1N aqueous hydrochloric acid. The layers were separated, and the organic layer was washed with 12% brine (5.0 Kg) The solvent was removed under vacuum to give a yellow oil, which was filtered to remove salts to provide 956 g (98% yield) of 4-bromo-thiophene-3-carboxylic acid ethyl ester, which was used in the next step without further purification. $^1$H NMR (400 MHz, CDCl$_3$): δ 8.10 (d, 1H, J=3.5 Hz), 7.30 (d, 1H, J=3.6 Hz), 4.34 (q, 2H, J=7.10 Hz), 1.38 (t, 3H, J=7.20 Hz); $^{13}$C NMR (400 MHz, CDCl$_3$): δ14.49, 60.95, 110.49, 124.86, 130.93, 133.67, 160.68.

Part B, Preparation of 4-bromo-5-nitro-thiophene-3-carboxylic acid ethyl ester.

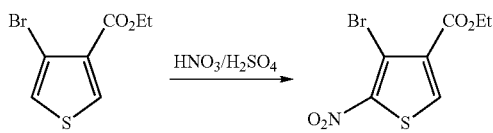

To a flask containing sulfuric acid (1900 mL) at −10 to −15° C. was added the product from Part A (265 g, 1.13 mol) at a rate to maintain the temperature at −10° C. To this mixture was added a mixture of fuming nitric acid (75 g, 1.19 mol) and sulfuric acid (350 mL) while maintaining the temperature at −10° C. The reaction mixture was then carefully poured, in portions, into a mixture of water (1 L) and ice (12 Kg), and the product immediately precipitated during the addition. The product was isolated by filtration and the wet cake was washed with water (5 L), 10% NaHCO$_3$ (5 L), followed by water (5 L), and petroleum ether (4 L), and dried in a vacuum oven to provide 302 g of the crude title product. This crude material was then recrystallized from ethanol/t-butyl methyl ether to provide 235 g (74%) of 4-bromo-5-nitro-thiophene-3-carboxylic acid ethyl ester. $^1$H-NMR (DMSO-d$_6$): 8.68 (s, 1H), 4.32 (q, 2H, J=7.09), 1.34 (t, 3H, J=7.07); $^{13}$C-NMR (DMSO-d$_6$); 159.11, 147.13, 138.77, 131.17, 112.57, 61.25, 14.06. Melting point: 94-95° C.

Part C. Preparation of 4-benzylsulfanyl-5-nitro-thiophene-3-carboxylic acid ethyl ester.

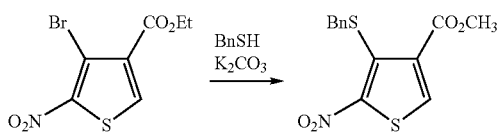

The product from Part B (400 g, 1.43 mol) and ethanol (5.6 L) were charged to a 12 L 3-neck round-bottomed flask and the yellow slurry was cooled to 12-14° C. Potassium carbonate (211.2 g, 1.53 mol) was added as a solution in water (800 mL) all at once. The temperature increased to 16° C., most of the solids dissolved and the solution became pink/red in color. Benzyl mercaptan (189.8 g, 1.53 mol) was added via addition funnel over 1.75 h. The temperature was maintained at 16-20° C. during the addition. After a rinse with ethanol (50 mL), the slurry (product precipitated during addition) was mixed at ambient temperature for an additional 2.5 h. Water (5 L) was added over 40 min, and the slurry was stirred at ambient temperature for 1.5 h. The product was isolated by filtration, rinsed with ethanol/water (1/1, 2×1 L) followed by cold heptane (2×1 L). The product was dried at 40° C. under vacuum to provide 4-benzylsulfanyl-5-nitro-thiophene-3-carboxylic acid ethyl ester (430.8 g, 93%).

Part D. Preparation of (4-benzylsulfanyl-5-nitro-thiophen-3-yl)-methanol.

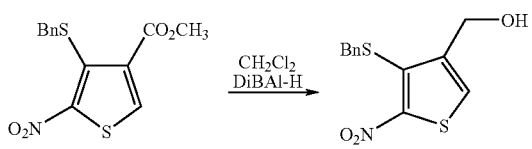

To a flask equipped with an addition funnel was added the product from Part C (5.0 g, 15.46 mmol) and dichloromethane (50 mL). The mixture was then cooled and maintained at −43° C. (dry ice/acetonitrile) when diisobutylaluminum hydride (DIBAL-H, 1M in CH$_2$Cl$_2$, 32.5 ml, 32.5 mmol) was slowly added over 45 minutes. After the addition was complete, the mixture was allowed to stir at −43° C. for 2 hours. The dry ice/acetonitrile bath was replaced with an ice bath and then the mixture was slowly quenched with 1M aqueous HCl (100 mL). The layers were separated and the organic layer was filtered through celite, concentrated under vacuum and subjected to purification by silica gel column chromatography (5% to 50% ethyl acetate/hexanes) to provide 3.28 g (75%) of (4-benzylsulfanyl-5-nitro-thiophen-3-yl)-methanol as a yellow-orange colored oil that solidifies upon standing. $^1$H NMR (300 MHz, DMSO-d$_6$) δ ppm 4.26 (s, 2H) 4.33 (dd, J=5.52, 1.10 Hz, 2H) 7.14- 7.29 (m, 5H) 7.78 (s, 1H).

Part E. Preparation of 3-benzylsulfanyl-4-chloromethyl-2-nitro-thiophene.

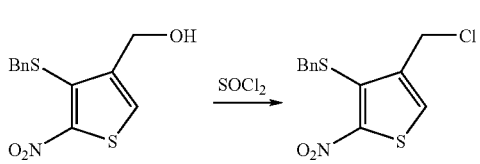

A solution of the product from Part D (35.59 g, 126.5 mmol) in toluene (175 mL) was cooled to 6° C. and DMF (0.925 g, 12.65 mmol) was added. Then a solution of thionyl chloride (16.25 g, 136.59 mmol) in toluene (17 mL) was added over 18 min. The solution was then warmed to room temperature and mixed for 1.5 h at room temperature. The reaction was quenched by addition of 10% sodium carbonate (71 mL). The majority of the aqueous phase was removed and the remaining solution was filtered through celite. The rest of the aqueous phase was removed then the organic solution concentrated to provide 32.46 g (85.6%) of 3-benzylsulfanyl-4-chloromethyl-2-nitro-thiophene as an oil.

Part F. Preparation of N-tert-bntyl ester-N-(4-benzylsulfanyl-5-nitro-thiophen-3-ylmethyl)-methanesulfonamide.

Method A:

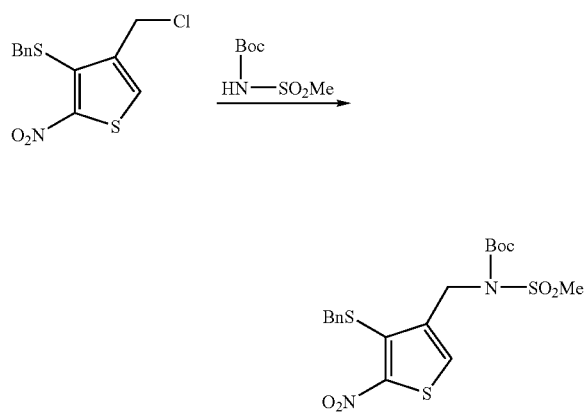

The product from Part E (32.46 g, 108.27 mmol) was dissolved in dimethyl acetamide (162 mL) and to the solution was added N-tert-butyl ester-methanesulfonamide (22.3 g, 114.22 mmol) and potassium carbonate (10.51 g, 76.04 mmol). The resulting solution was heated to 55 ° C. for 16 h. To the cooled reaction mixture was added ethyl acetate (444 mL) and the solution was washed with a 7% aqueous sodium chloride (3×444 mL) solution. The solvent was removed under vacuum and the residue was dissolved in ethanol. The product crystallized and was isolated by filtration and washed with cold ethanol to provide 39 g (80%) of N-tert-butyl ester-N-(4-benzylsulfanyl-5-nitro-thiophen-3-ylmethyl-methanesulfonamide as a light yellow solid. $^1$H-NMR(DMSO-d$_6$) δ 1.42 (9H, s), 3.41 (3H, s), 4.19 (2H, s), 4.63 (2H, s), 7.1-7.3 (5H, m), 7.62 (1H, s); $^{13}$C-NMR (DMSO-d$_6$) δ 27.50, 39.24, 41.76, 44.99, 84.09, 126.92, 127.40, 127.93, 128.26, 131.33, 136.21, 141.48, 150.16, 150.81; DCI-MS 476 (M+18).

Method B:

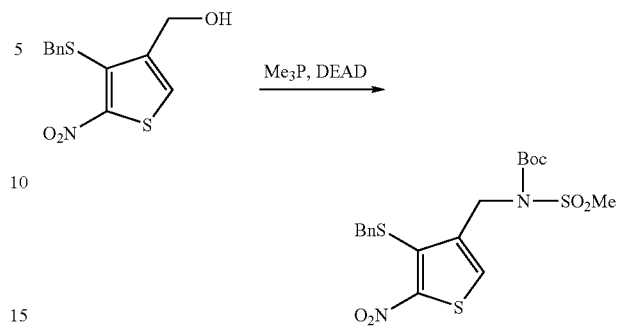

To a solution of N-Boc methanesulfonamide (12.00 g, 61.5 mmole) and 1M of trimethylphosphine (61.5 mL, 61.5 mmole) in THF was added (4-benzylsulfanyl-5-nitro-thiophen-3-yl)-methanol (11.5 g, 40.9 mmole) in 135 mL THF over 15 min at ~25° C. The resulting solution was stirred at ~25° C. for ~10 min., and 26.7 g of 40% DEAD solution in toluene (26.7 g, 61.4 mmole) added slowly over ~10 min (slightly exothermic, water bath cooling). The reaction mixture was stirred at ~25° C. overnight or until the starting material was consumed as indicated by HPLC. The reaction mixture was concentrated to dryness, and ethyl acetate (200 mL) and 5% NaHCO$_3$ aq. Solution (200 mL) added. The upper organic was washed with 5% NaHCO$_3$ (200 mL×2), and 25% brine (200 mL). The organic was dried over MgSO4, filtered. The filtrate was concentrated to ~50-60 mL volume (some solid), diluted with heptane (50 mL). The solid was filtered off, rinsed with ethyl acetate: heptane (1:1, 20 mL). The filtrate was concentrated to ~40 mL volume, chromatographed om a silica gel column (250 g), eluting with heptane :acetone (4:1), The main fractions of product were pooled, and concentrated to dryness to yield an oil (18.0 g), which was crystallized from abs ethanol to give 14.1 g product of N-tert-butyl ester-N -(4-benzylsulfanyl-5-nitro-thiophen-3-ylmethyl)-methanesulfonamide as a light yellow solid.

Part G. Preparation of 4-[(N-tert-butyl ester-methanesulfonyl-amino)-methyl]-2-nitro-thiophene-3-sulfonyl chloride.

Method A:

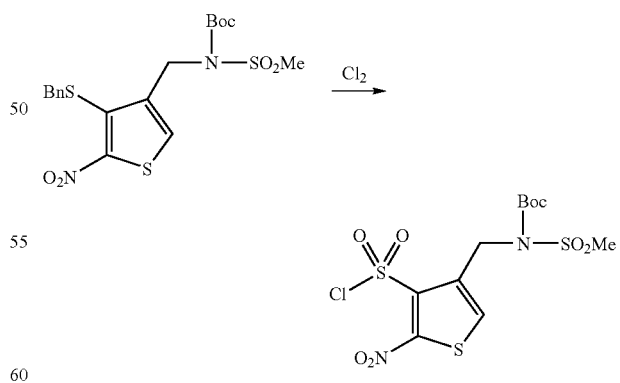

The product from Part F (18.0 g, 39.3 mmole) was dissolved in a mixture of dichloromethane: acetic acid: water (225 mL: 75 mL: 75 mL). The resulting mixture was cooled down to −5° C. Chlorine gas (minimum 3 eq.) was bubbled slowly through the mixture for a few minutes at the internal temperature of <5° C. and the mixture stirred at 0° C. for 1 h.

the lower organic phase was then separated and washed with 25% brine (200 mL). The organic phase was dried over sodium sulfate, filtered, and concentrated to approx. 30 mL volume. Heptane (100 mL) was added slowly. The resulting slurry was stirred at room temperature for 1 h, filtered, rinsed with heptane (30 mL), and dried under vacuum to provide 14.0 g, (82%) of 4-[(N-tert-butyl ester-methanesulfonyl-amino)-methyl]-2-nitro-thiophene-3-sulfonyl chloride as a solid, $^1$H-NMR(CDCl$_3$) δ 1.51 (9H, s), 3.40 (3H, s), 5.07 (2H, s), 7.55 (1H, s); $^{13}$C-NMR(CDCl$_3$) δ 28.15, 42.40, 46.88, 86.11, 123.95, 134.28, 138.64, 150.34; DCI-MS 452 (M+18).

Method B:

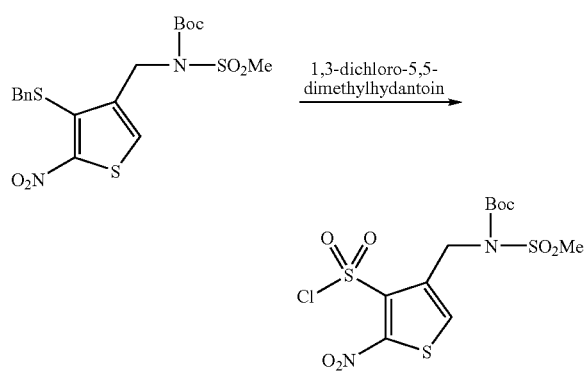

The product from Part F (18.4 g, 40.1 mmole) was dissolved in a mixture CH$_2$Cl$_2$: HOAc: H$_2$O (140 mL: 20 mL: 40 mL). The resulting mixture was cooled down to 10° C. 1,3-Dichloro-5,5-dimethylhydantoin (24.0 g, 121 mmole) in 80 mL of CH$_2$Cl$_2$ was added portionwise at ~10° C. and the mixture stirred at 10° C. for 20 h. 100 mL of 5% sodium metabisulfite solution was added slowly at <25° C., followed by addition of 100 mL of 20% potassium phosphate dibasic solution. The lower organic phase was separated and used directly in the next step without further purification. However, an analytical sample of 4-(N-t-butoxycarbonylmethanesulfonylamino-methyl)-2-nitro-thiophene-3-sulfonyl chlorid was prepared by crytaliization from heptane; Mp ~75° C. (decomposed, uncorrected); $^1$H-NMR (CDCl$_3$) δ 1.51 (9H, s), 3.40 (3H, s), 5.07 (2H, s), 7.55 (1H, s); $^{13}$C-NMR(CDCl$_3$) δ 28.15, 42.40, 46.88, 86.11, 123.95, 134.28, 138.64, 150.34; DCI-MS 452 (M+18).

Part H Preparation of 4-[(N-tert-butyl ester-methanesulfonyl-amino)-methyl]-2-nitro-thiophene-3-sulfonic acid amide.

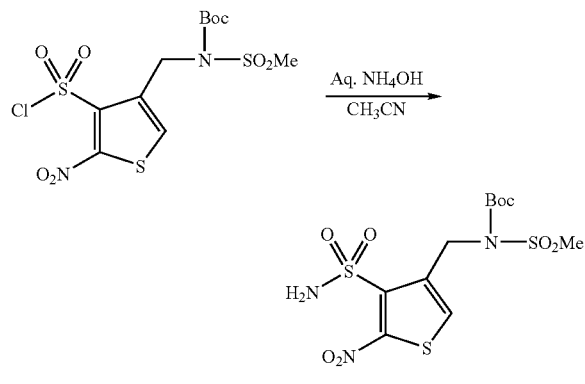

To a 500 mL flask were charged the product from Part G (13.95 g, 32.0 mmole), and acetonitrile (200 mL). The solution was cooled down to −5° C., and 7.0 mL of concentrated ammonium hydroxide aqueous solution was added dropwise at <5° C. The orange colored slurry was mixed at 0° C. for 1 h, then concentrated to 50 mL volume. The mixture was diluted with ethyl acetate (200 mL), 5% sodium bicarbonate (100 mL) and 25% brine (100 mL), The upper organic phase was washed with 25% brine (150 mL), dried over magnesium sulfate, and filtered. The filtrate was concentrated to dryness. The crude product was chromatographed on silica gel (300 g), eluting with heptane: acetone (3:1) to (2:1) to provide 9.7 g (73%) of 4-[(N-tert-butyl ester-methanesulfonyl-amino)-methyl]-2-nitro-thiophene-3-sulfonic acid amide as a solid. $^1$H-NMR(DMSO-d$_6$) δ 1.44 (9H, s), 3.49 (3H, s), 4.93 (2H, s), 7.57 (1H, s), 7.93 (2H, s); $^{13}$C-NMR(DMSO-d$_6$) δ 27.51, 41.79, 46.58, 84.19, 125.48, 137.28, 137.32, 150.06; DCI-MS 433 (M+18).

Part I. Preparation of 4-(methanesulfonylamino-methyl)-2-nitro-thiophene-3-sulfonic acid amide.

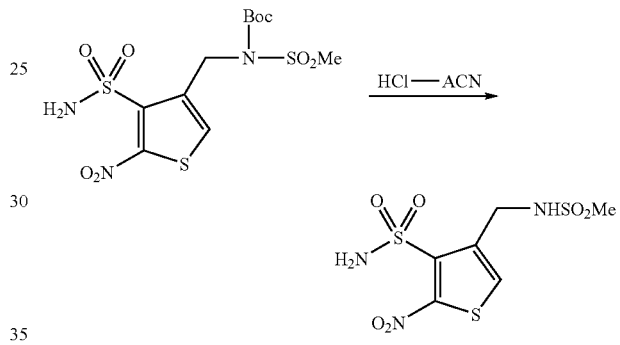

To the product from Part H (9.7 g, 23.3 mmol) in acetonitrile (200 mL) was added 22.0 mL of concentrated hydrochloric acid solution at room temperature. The reaction mixture was stirred at room temperature for 8 hr. The light-yellow solution was concentrated to 40 mL volume. Isopropyl acetate (150 mL), and 25% brine (100 mL) were added The upper organic phase was separated, and the lower aqueous phase extracted with 2-propanol (75 mL×2). The combined organic extracts were washed carefully with a mixture of 5% sodium bicarbonate (100 mL), and 25% brine (100 mL). The organic solution was dried over magnesium sulfate, filtered, and concentrated to 40-50 mL volume. The slurry was stirred at room temperature for 5 hr, and 0° C. for 2h. The solid was collected by filtration, then dried at 35° C. under vacuum overnight to provide 5.9 g (80%) of 4-(methanesulfonylamino-methyl)-2-nitro-thiophene-3-sulfonic acid amide. H-NMR(DMSO-d$_6$) δ 2.96 (3H, s), 4.35 (2H, s), 7.62 (2H, s, br), 7.86 (1H, s), 7.88 (2H, s, br); $^{13}$C-NMR(DMSO-d$_6$) □39.94, 42.01, 127.22, 137.33, 137.79, 149.63; DCI-MS 333 (M+18).

Part J. Preparation of 2-amino-4-(methanesulfonylamino-methyl)-thiophene-3-sulfonic acid amide.

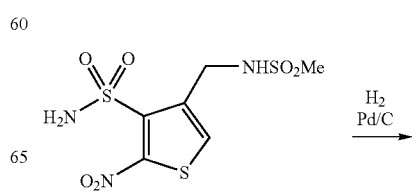

-continued

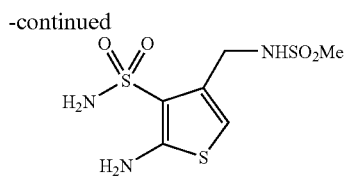

The product from Part I (5.90 g, 18.73 mmol) was hydrogenated with 5.90 g of 10% Pd/C in tetrahydrofuran (170 mL) at 25-30° C. overnight. The reaction mixture was filtered, and rinsed with tetrahydrofuran (50 mL). The filtrate was concentrated to 30 mL volume, The resulting suspension was stirred at 25° C. for 2 h, and diluted with hexane (30 mL). The off-white solid that formed was filtered, rinsed with hexane (20 mL), and dried at 25° C. under vacuum to provide 5.00 g (93%) of 2-amino-4-(methanesulfonylamino-methyl)-thiophene-3-sulfonic acid amide. $^1$H-NMR(DMSO-d$_6$) δ 2.90 (3H, s), 4.16 (2H, d, J=6.4 Hz), 6.25 (1H, s), 6.62 (2H, s), 7.14 (2H, s), 7.27 (1H, t, J=6.4 Hz); $^{13}$C-NMR (DMSO-d$_6$) δ 39.80, 41.77, 103.10, 110.81, 133.96, 157.66; ESI-MS 308 (M+23), 286 (M+1); Anal. Calcd for C$_6$H$_{11}$N$_3$O$_4$S$_3$: C, 25.25; H, 3.89; N, 14.73; S, 33.71. Found: C, 25.37; H, 3.74; N, 14.42; S, 33.36.

Example 2B

Preparation of 2-Amino-4-(methanesulfonylamino-methyl)-thiophene-3-sulfonic acid amide (Method B).

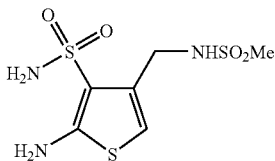

Part A. Preparation of 4-Bromothiophene-3-carbonitrile.

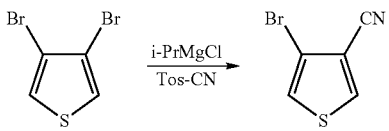

To a three-necked flask was charged THF (8.3 L) and dibromothiophene (435.5 g, 1.8 mol), the solution was cooled to 0° C., to the solution was added iPrMgCl (2.0 M solution in THF, 1125 ml, 2.25 mol) slowly keeping the temperature below 5° C., The resulting mixture was stirred at 0~5° C. until HPLC indicate that the s m, was less than 1%. To the cooled reaction mixture was added a solution of TsCN (416 g, 2.25 mol) in THF (850 ml) dropwise keeping temperature below 5° C. The resulting mixture was stirred at 0° C. until the intermediate Grignard was consumed. To the reaction mixture was added H2O (100 ml) and the resulting mixture was stirred for 10 min. The THF was partially removed under vacumm (to about 800 ml). EtOAc (5.0 L) was added to the mixture followed by 1N HCl (4.0 L), the resulting mixture was stirred for 10 min. The organic layer was separated, washed with 5% NaHCO3 (4.0 L) followed by 12% brine (4.0 L). The organic layer was then treated with carbon (40 g) and dried over Na2SO4 and filtered through a filter agent. The filtrate was concentrated to obtain the product, which was further dried under high vacuum to give 332 g of product as beige solid (94.3% weight adjusted yield, HPLC purity of 96.5% pa). A small sample of the product was further purified by crystallization with EtOAc/Heptane to obtain analytical standard. $^1$H NMR (400 MHz, CDCl$_3$): δ 7.94 (d, 1H, J=3.3 Hz), 7.35 (d, 1H, J=3.3 Hz); $^{13}$C NMR (400 MHz, CDCl$_3$): δ 112.23, 113.51, 114.58, 124.89, 136.35.

Part B. Preparation of 4-Bromo-5-nitrothiophene-3-carbonitrile.

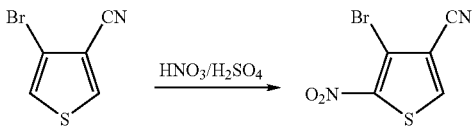

To a 3 L of jacketed RB-flask equipped with a mechanical stirrer was added conc, H$_2$SO$_4$ (1500 mL). The content was cooled with a circulation bath to −20° and to the flask was added the product from Part A (149 g, 792.34 mmol) slowly (the process is not very exothermic) maintaining internal temperature below −10° C. To the above reaction mixture was then added a mixture of fuming nitric acid (45 mL, reagent grade, fuming, >90) and sulfuric acid (200 mL) slowly (exothermic) keeping the internal temperature slightly below −10° C. After the addition was completed, the circulation bath was disconnected and the reaction mixture was slowly warmed to ambient temperature within 3 hours. The reaction completion was monitored by HPLC. Upon completion of the reaction, the reaction mixture was poured into a mixture of water (1 L) and ice (14 Kg) in portions with vigorous mechanical stirring. The solid product precipitated out and ice (14 Kg) was added in portions, alternating with the addition of the reaction mixture. The solid product was filtered, washed with water (2×1 L), half saturated aqueous NaHCO$_3$ solution (2 L), followed by another water wash (2 L), and a petroleum ether wash (1 L), dried on filter under nitrogen flow, and further dried in vacuum oven at 45° C. overnight to give 184.7 g of crude 4-bromo-5-nitrothiophene-3-carbonitrile (98% weight adjusted yield, purity 97.3% pa). The crude product (184.7 g) was mixed with a mixture of MTBE-heptane-ab.EtOH (10:10:1, 1847 mL). The suspension was heated to reflux (61° C.), held at reflux for 30 min, then slowly cooled to ambient temperature. The product was collected by filtration, washed once with heptane (2 L), dried under nitrogen for 3 hours, and then further dried in vacuum oven at 45° C. for 4 hours to give 175 g of purified 4-bromo-5-nitrothiophene-3-carbonitrile (95% yield). MP: 176-178° C. $^1$H-NMR (DMSO-d$_6$): 8.99 (s, 1H). $^{13}$C-NMR (DMSO-d$_6$): 142.66 (CH), 142.66, 114.72, 113.89, 112.40. Elemental analysis: Calcd for C$_5$H$_1$BrN$_2$O$_2$S: C, 25.77%; H, 0.43%; N, 12.02%; Br, 34.29%; S, 13.76%. Found: C, 25.70%; H, 0.15%; N, 11.84%; Br, 34.01%; S, 13.86%.

Part C. Preparation of 4-(Benzylthio)-5-nitrothiophene-3-carbonitrile.

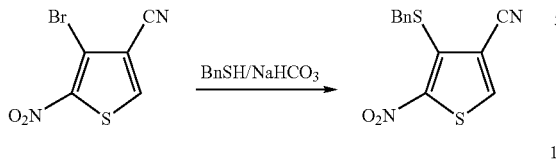

To a suspension of the product from Part B (16.7 g, 71.7 mmol) in THF (83 mL) was added a solution of K$_2$CO$_3$ (10.9 g, 78.8 mmol) in H$_2$O (67 mL). The resulting slurry was cooled to 10-15° C. and a solution of benzyl mercaptan (9.8 g, 78.8 mmol) in THF (51 mL) was added over 40 minutes via addition funnel. After stirring at RT for 1.5 h, the reaction mixture was diluted with EtOAc (160 mL) and a pH 7 buffer (160 mL). The layers were separated and the organic phase was dried over Na$_2$SO$_4$ and concentrated in vacuo. The crude material was taken up in EtOH (150 mL). The solution was mixed at RT and the product gradually crystallized. After mixing for 4 h, H$_2$O (150 mL) was added over 20 minutes and the slurry was stirred an additional 1.5 h. The product was isolated by filtration to give of 4-(benzylthio)-5-nitrothiophene-3-carbonitrile as a yellow solid (19.55 g, 98%). $^1$H NMR (DMSO-D6): 8.87 (s, 1H), 7.28 (m, 5H), 4.54 (s, 2H).

Part D. Preparation of 4-Cyano-2-nitro-thiophene-3-sulfonic acid amide.

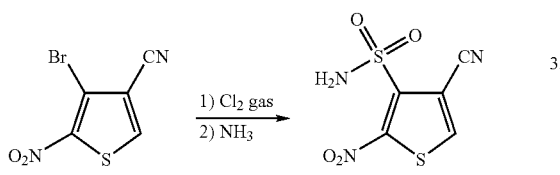

Chlorine gas (106.1 g, 1.50 mol) was slowly bubbled into a suspension of the product from Part C (100.0 g, 361.9 mmol) in HOAc (800 mL) and H$_2$O (200 mL) over 70 minutes at 0-8° C. The reaction mixture was purged with nitrogen then H$_2$O (350 mL) was added over 20 minutes and the slurry was cooled to 0-5° C. The product was isolated by filtration and dried at RT to give 79.39 g of the sulfonyl chloride, which was used directly in the next step without isolation. A solution of thiophenesulfonyl chloride (134.80 g, 0.5335 mol) in THF (1150 mL) was added to a solution of THF (3350 mL) containing ammonia (22.56 g, 1.325 mol) at ca. −50° C. over 1.5 hr. to give 4-cyano-2-nitro-thiophene-3-sulfonic acid amide. The excess ammonia and solvent were removed under reduced pressure starting to give a thick slurry. Residual THF was chased with MeOH (500 mL) under reduced pressure, and the residue treated with MeOH (700 mL) to give a dark slurry The slurry was mixed at 0 to 10° C. for 35 min. and the solid collected by filtration (the crude product was analyzed by HPCL to give a 81% yield). The crude product solid was further purified by rinsing with ice-cold MeOH-water (1:1 v/v, 2×100 mL) followed by water (1×200 and 1×250 mL). The solid was dried on the filter to afford 79.80 g of 4-Cyano-2-nitro-thiophene-3-sulfonic acid amide (64.1% yield, with 14.25 g of the product lost to the filtrate). $^1$H NMR (DMSO-d6): δ=8.90 (s, 1H), 8.22 (br s, 2H). $^{13}$C NMR (DMSO-d6): δ=149.5, 142.1, 140.7, 112.3, 109.7.

Part E. Preparation of 2-Amino-4-cyanothiophene-3-sulfonamide.

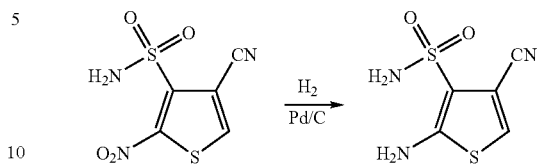

A solution of the product from Part D (77 g, 330.1 mmol) in THF (1500 mL) was treated with 10% Pd on carbon (77 g) at 40 psi hydrogen pressure at room temperature for 32 hr. The mixture was filtered and the solvent removed under reduced pressure to give a solid (66.60 g). The solid was placed under oil pump vacuum at room temperature to afford 2-amino-4-cyanothiophene-3-sulfonamide (65.85 g, 98.1% yield). The solid (59.97 g) was further purified by treating with refluxing absolute EtOH (1000 mL) for 3.75 hr, then cooling and filtering at 1.4° C. and drying on the funnel at room temperature to a constant wt. to give a total of 53.39 g of purified 2-amino-4-cyanothiophene-3-sulfonamide in three crops (79.6% yield). $^1$H NMR (DMSO-d6): δ=7.48 (s, 1H), 7.33 (br s, 2H), 6.92 (br s, 2H). $^{13}$C NMR (DMSO-d6): δ=159.6, 121.2, 113.8, 111.4, 106.3.

Part F. Preparation of 2-Amino-4-(aminomethyl)thiophene-3-sulfonamide,

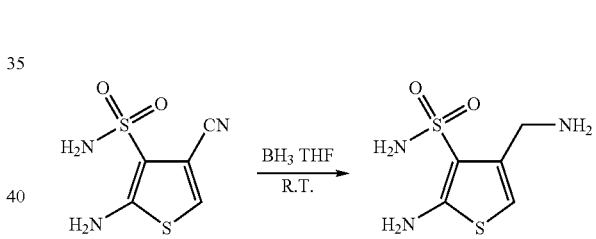

To a solution of the product from Part E (10.00 g, 49.20 mmol) in THF (100 mL) was added borane-methyl sulfide complex (BMS, 2.0 M in THF, 70.21 g, 164.24 mmol) over 3 minutes at ambient temperature. The reaction was stirred for 30 minutes and the reaction completion was monitored by HPLC, Upon completion of the reaction, the solvent was distilled until a thick slurry was obtained. The mixture was cooled to 15° C. and MeOH (75 mL) was added dropwise while maintaining the temperature at <40° C. The resulting solution was concentrated and the residue was chase with MeOH (2×100 mL) at atmospheric pressure to a volume of ca, 50 mL, The reaction was cooled to 14° C. and MeOH-HCl (2M, 74 mL) was added over 6 minutes to give an orange slurry. To this slurry was added MeOH (150 mL) and the mixture was concentrated in vacuo to an oil. The oil was chased with MeOH (2×100 mL) to give 13.41 g of crude product as an oil that solidified on cooling. A portion of this dihydrochloride was purified via column chromatography to afford analytical sample of 2-amino-4-(aminomethyl)thiophene-3-sulfonamide, ($^1$H NMR (DMSO-D6): 6.54 (s, 2H), 6.22 (s, 1H), 4.59 (vbr s, 3H), 3.66 (s, 2H), Part G. Preparation of 2-Amino-4-(methylsulfonamidomethyl)thiophene-3-sulfonamide.

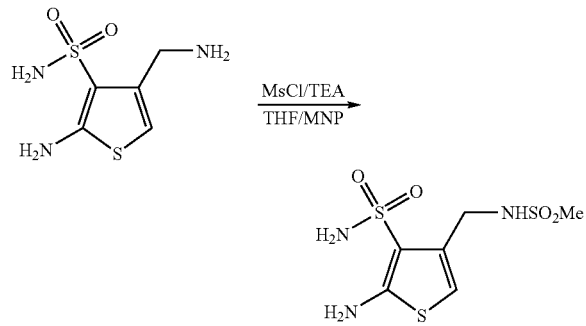

Methanesulfonyl chloride (323.4 mg, 2.823 mmol) was added to a solution of the product from Part F (500.3 mg, 2.414 mmol) in THF (5.0 mL), NMP (1.0 mL), and triethylamine (TEA, 0.841 mL, 6.03 mmol) over 23 minutes at ambient temperature. The reaction mixture was stirred at ambient temperature for 1.0 hour. THF (10 mL) was added to the slurry, and the mixture was stirred for 1.0 hour then filtered. The filter cake was washed with THF (10 mL) and the combined liquors concentrated in vacuo to give an oil. Residual THF was chased with dichloromethane (2×10 mL) in vacuo to afford 1.546 g of a clear oil. A portion of this oil (1.273 g) was dissolved in EtOAc (12.7 mL) and washed with 7% NaCl solution (4×4.2 mL) The organic phase was concentrated until solid NaCl began to form. EtOAc (10 mL) was added and the mixture was filtered. The filtrate was concentrated in vacuo to ca. 2.5 mL volume at which time 2-amino-4-(methylsulfonamidomethyl) thiophene-3-sulfonamide began crystallizing out as platelets. The combined aqueous was extracted with EtOAc (2×5 mL). The resulting organic phase was added to the EtOAc from above, Dichloromethane (2.5 mL) was added to the combined organic phase followed by the addition of heptane (2.5 mL) over 27 minutes. The resulting slurry was mixed at −12 to 0° C. for 50 minutes then filtered. The filter cake was dried on the funnel with a nitrogen flow to give 356.2 mg of light-beige solid ($^1$H NMR (DMSO-D6): 7.27 (t, 1H), 7.14 (s, 2H), 6.62 (s, 2H), 6.25 (s, 1H), 4.17 (d, 2H), 2.90 (s, 3H).

Example 3

Preparation of N-[(3-{1-[(cyclobutyl)amino]-4-hydroxy-2-oxo -1,2-dihydro-quinolin-3-yl}-1,1-dioxo-1,4-dihydro-1λ[6]-thieno[2,3-e][1,2,4]thiadiazin-7-yl) methyl]methane sulfonamide (Compound I)

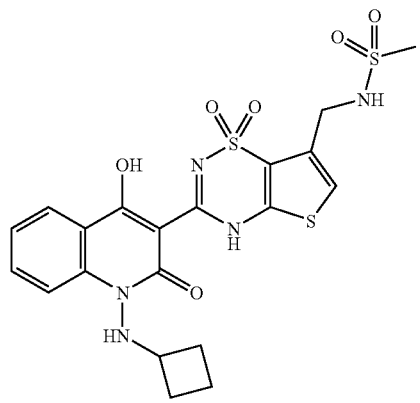

Part A. Preparation of (Bis-methylsulfanyl-methylene)-methyl-sulfonium tetrafluoroborate.

Dimethyl sulfate (22.84 mL, 240 mmol) and dimethyl trithiocarbonate (26.48 mL, 240 mmol) were added to acetonitrile (80 mL). The resultant dark yellow solution was heated to 90° C. for 2 hours. The mixture was then allowed to cool to 55° C. and then a solution of tetrafluoroboric acid (54% in diethyl ether, 48 mL) was added over 5 min time. The resultant solution was stirred for an additional 15 min, followed by pouring it into a solution of ice-cold diethyl ether (600 mL), The white solid that formed was collected and washed with diethyl ether (3×50 mL) and dried in a vacuum oven to provide (bis-methylsulfanyl -methylene)-methyl-sulfonium tetrafluoroborate salt (47.3 g, 83%) as a colorless solid.

Part B. Preparation of N-[3-{1-[(cyclobutyl)amino]-4-hydroxy-2-oxo-1,2-dihydro-quinolin -3-yl}-1,1-dioxo-1,4-dihydro-1λ[6]-thieno[2,3-e][1,2,4]thiadiazin-7-yl)methyl]methane-sulfonamide.

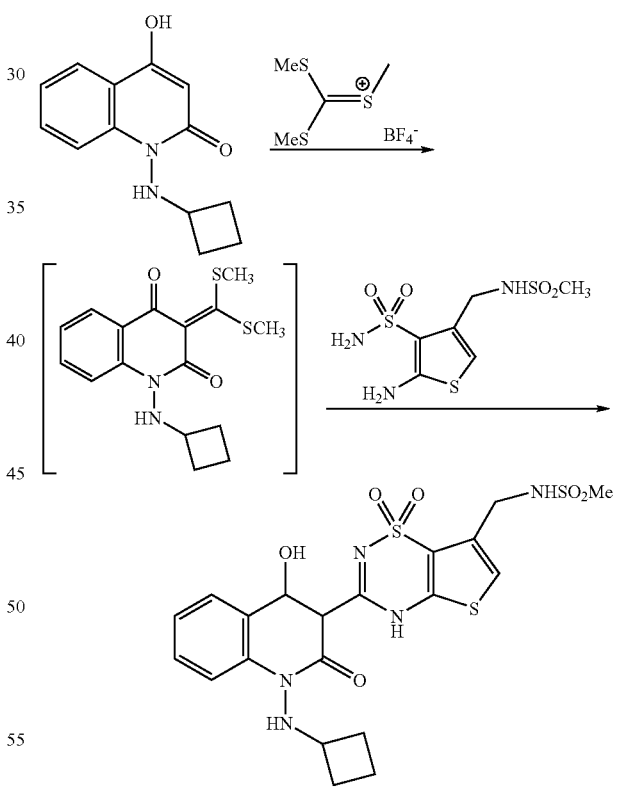

The product from Example 1 (18.0 g, 78.3 mmol) was dissolved in dioxane (157 mL) and then diethyl isopropylamine (80.5 g, 626.4 mmol) added, then the solution cooled to 0° C. followed by the addition of (bis-methylsulfanyl-methylene)-methyl-sulfonium tetrafluoroborate salt (52.4 g, 218.3 mmol) in portions. The resultant solution was stirred at room temperature for 2 hours, followed by the addition of ethyl acetate (500 mL) and water (500 mL). The mixture was extracted and the resultant organic layer separated then dried over magnesium sulfate. The organic solution was then concentrated under vacuum to provide an orange oil which was dissolved in acetonitrile (150 mL) and added dropwise over 20 min to a solution of the product from Example 2A or Example 2B (18.18 g, 63.8 mmol) in acetonitrile (100 mL) heated to 85° C. The resultant solution was heated at 85° C. for an additional 2.5 hours, then allowed to cool to room temperature and sit overnight without stirring. After 24 hours a solid had formed, which was collected and washed with acetonotrile (2×50 mL), then dried under vacuum to provide 27.0 g (80%) of N-[(3-{1-[(cyclobutyl)amino]-4-hydroxy-2-oxo-1,2-dihydro-quinolin-3-yl}-1,1-dioxo -1,4-dihydro-1$\lambda^6$-thieno[2,3-e][1,2,4]thiadiazin-7-yl)methyl] methane-sulfonamide (i.e., Compound I) as a solid, $^1$H-NMR(300 MHz, DMSO-$d_6$) δ 14.46 (bs, 1H), 8.15 (m, 1H), 8.05 (d, J=8.4 Hz, 1H), 7.86 (m, 1H), 7.75 (t, J=6.3 Hz, 1H), 7.42 (m, 2H), 6.45 (bs, 1H), 4.30 (d, J=5.1 Hz, 2H), 3.76 (m, 1H), 2.99 (s, 3H), 2.03 (m, 4H), 1.57 (m, 2H); ESI-MS 524 (M+H)+.

Example 4

Preparation of N-[(3-{1-[(Cyclopropylmethyl)amino]-4-hydroxy-2-oxo-1,2-diliydroquinolin-3-yl}-1,1-dioxido-4H-thieno[2,3-e][1,2,4]thiadiazin-7-yl)methyl]methane-sulfonamide (Compound II).

Compound II was prepared according to the procedure described in Example 353 of U.S. patent application Ser. No. 10/699,513, the entire content of which is incorporated herein by reference. The procedure is provided below:

2-(N'-Benzylidene-hydrazino)-benzoic acid (5.0 g, 20.81 mmol) in 1:1 tetrahydrofuran and methanol (50 mL) was reacted with a solution of trimethylsilyl diazomethane in hexanes (2.0M, 12 mL, 25.0 mmol) at 0° C. for 1 hour then stirred at 25° C. for 48 hours. The solvent was removed under vacuum to give methyl 2-[2-benzylidenehydrazino]benzoate as a solid (6.00 g, 100%). $^1$H NMR (300 MHz, DMSO-$d_6$) δ ppm 3.87 (s, 3H) 6.84 (td, J=7.54, 1.10 Hz, 1H) 7.41 (m, 3H) 7.54 (m, 1H) 7.74 (m, 3H) 7.86 (dd, J=8.09, 1.47 Hz, 1H) 8.21 (s, 1H) 11.02 (s, 1H), Methyl 2-[2-benzylidenehydrazino]benzoate (5.29 g, 20.81 mmol) in toluene (80 mL) was reacted with ethyl chlotomalonate (2.68 mL, 25.0 mmol) at reflux for 4 hours. The reaction mixture was cooled to 25° C. and concentrated under vacuum The residue was triturated with diethyl ether and hexanes (3:1) to give methyl 2-[2-benzylidene-1-(3-ethoxy-3-oxopropanoyl)hydrazino]benzoate (5.17 g, 70%), MS (DCI) m/z 355 (M+H)+. $^1$H NMR (300 MHz, DMSO-$d_6$) δ ppm 3.32 (s, 2H) 3.69 (s, 3H) 3.73 (s, 3H) 7.16 (s, 1H) 7.32 (dd, J=7.72, 1.10 Hz, 1H) 7.40 (m, 3H) 7.63 (m, 2H) 7.70 (td, J=7.63, 1.29 Hz, 1H) 7.85 (td, J=7.72, 1.47 Hz, 1H) 8.10 (dd, J=7.72, 1.47 Hz, 1H).

Methyl 2-[2-benzylidene-1-(3-ethoxy-3-oxopropanoyl)hydrazino]benzoate (5.17 g, 14.59 mmol) in ethanol (100 mL) was reacted with sodium ethoxide (21% by weight in ethanol, 5.50 mL, 14.60 mmol) at 25° C. then heated at 50° C. for 1 hour. After cooling to 25° C., the reaction mixture was poured into water, acidified to pH 4 with 1M hydrochloric acid and extracted with ethyl acetate. The organic layer was dried over anhydrous sodium sulfate, filtered and the solvent removed under vacuum to give ethyl 4-hydroxy-2-oxo-1-{[phenylmethylene]amino}-1,2-dihydroquinoline-3-carboxylate (4.51 g, 96%). MS (DCI) m/z 323 (M+H)+. $^1$H NMR (300 MHz, DMSO-$d_6$) δ ppm 3.73 (s, 3H) 7.21 (m, 1H) 7.56 (m, 5H) 7.95 (m, 2H) 8.03 (d, J=7.72 Hz, 1H) 9.08 (s, 1H).

To a solution of 25% by weight aqueous potassium hydroxide (200 mL) and 1,4-dioxane (50 mL) heated to 90-100° C. was added portion wise ethyl 4-hydroxy-2-oxo-1-{[phenylmethylene]amino}-1,2-dihydroquinoline-3-carboxylate (6.72 g, 20.0 mmol). The reaction mixture was heated at reflux for 90 minutes allowing distillation to occur and additional water and dioxane (30 mL each) were added to the reaction vessel to reach the original volume. The mixture was refluxed for an additional 90 minutes with distillation, cooled, washed with 200 mL of 1:1 diethyl ether/ethyl acetate, acidified with concentrated hydrochloric acid to pH 2 and the resulting solid was collected by filtration, washed with water and dried to constant mass to give 1-amino-4-hydroxyquinolin-2(1H)-one as a tan sold (3.22 g, 91% yield), MS (DCI) m/z 177 (M+H)+. $^1$H NMR (300 MHz, DMSO-$d_6$) δ 5.56 (s, 2H) 5.94 (s, 1H) 7.20 (t, J=7.54 Hz, 1H) 7.62 (m, 1H) 7.85 (m, 2H) 11.33 (s, 1H).

To the suspension of 1-amino-4-hydroxyquinolin-2(1H)-one (1.033 g, 5.86 mmol) in methanol (58 mL) was added acetic acid (0.29 mL) and cyclopropylcarboxaldehyde (482 □L, 6.45 mmol) followed by the addition of sodium cyanoborohydride (744.6 mg, 11.85 mmol) at room temperature. The suspension was stirred at room temperature overnight and quenched with half saturated brine (100 mL) and sodium bicarbonate (425 mg, 5.06 mmol). The mixture was extracted with ethyl acetate (300 mL) and the organic layer was separated and washed with half saturated brine (2×50 mL) The combined aqueous layers were extracted with dichloromethane (2×100 mL). The combined organic solution was dried with magnesium sulfate, filtered and concentrated, to give (1-[(cyclopropylmethyl)amino]-4-hydroxyquinolin -2(1H)-one) which was used without any purification. $^1$H NMR (300 MHz, DMSO-$d_6$) δ 0.09 (m, 2H) 0.40 (m, 2H) 0.95 (m, 1H) 2.70 (t, J=6.43 Hz, 2H) 5.91 (s, 1H) 6.10 (t, J=6.07 Hz, 1H) 7.21 (m, 1H) 7.62 (t, J=7.17 Hz, 1H) 7.87 (m, 2H) 11.42 (br s, 1H).

To the suspension of 1-[(cyclopropylmethyl)amino]-4-hydroxyquinolin-2(1H)-one (984.4 mg, 4.28 mmol) in 1,4-dioxane (40 mL) was added pyridine (2.8 mL, 34.6 mmol) and tris(methylthio)methyl methyl sulfate (prepared using the procedures in SYNTHESIS, 22-25, 1988; M. Barbero, S. Cadamuro, I. Degani, R, Fochi, A. Gatti, V, Regondi) (2.26 g, 8.55 mmol) at room temperature. The suspension was put in a preheated oil bath at 55° C. and stirred for 15 minutes. To the solution was added another portion of tris(methylthio)methyl methyl sulfate (2.26 g, 8.55 mmol) and the mixture was stirred at 55° C. for 15 minutes and cooled to room temperature. The mixture was concentrated in vacuo and the residue was diluted with dichloromethane and loaded on a silica gel column and eluted with dichloromethane, 2% ethyl acetate/dichloromethane and then 5% ethyl acetate/dichloromethane to give 3-[bis(methylthio)methylene]-1-[(cyclopropylmethyl)amino] quinoline -2,4(1H, 3H)-dione (852.1 mg, 60%). $^1$H NMR(300 MHz, DMSO-$d_6$) δ 0.15 (m, 2H) 0.42 (m, 2H) 0.98 (m, 1H) 2.61 (s, 6H) 2.73 (t, J=6.43 Hz, 2H) 6.05 (t, J=5.88 Hz, 1H) 7.15 (m, 1H) 7.64 (m, 1H) 7.76 (d, J=8.09 Hz, 1H) 7.98 (m, 1H).

Methyl 4-(benzylthio)-5-nitrothiophene-3-carboxylate was prepared according to the procedure as described in Stanetty, P. et. al., JOURNAL OF HETEROCYCLIC CHEMISTRY, 36, 761-765 (1999).

Methyl 4-(benzylthio)-5-nitrothiophene-3-carboxylate (5g, 16.2 mmol) in dichloromethane (150 mL) at −40° C. was reacted with diisobutylaluminum hydride (1 M in dichloromethane, 36 mL, 2.2 equivalents) added dropwise. The reaction was stirred for 15 minutes after complete addition, quenched with 10% aqueous sodium potassium tartrate solution and stirred at 25° C. for 1 hour. The organic layer was separated, filtered through celite ® (dratomaceous earth) and the filtrate was concentrated under reduced pressure. The resulting oil was purified by flash chromatography on silica gel with a Biotage-40s column eluting with 2:98 methanol/dichloromethane to give [4-(benzylthio)-5-nitrothien-3-yl]methanol as an oil, (4.32 g, 95%). $^1$H NMR (300 MHz, CDCl$_3$) δ ppm 4.21 (s, 2H), 4.39 (s, 2H), 7.11 (m, 3H), 7.23 (m, 2H) 7.40 (s, 1H).

[4-(benzylthio)-5-nitrothien-3-yl]methanol (3.9g, 13.9 mmol) in dichloromethane (8 mL) was reacted with diisopropylethylamine (7.42 mL, 3 equivalents) and methoxymethyl chloride (2.38 mL, 2.25 equivalents) at 25° C. 16 hours. The reaction was concentrated under reduced pressure and the residue purified by flash chromatography on silica gel using a Biotage-40m column eluting with dichloromethane to give 3-(benzylthio)-4-[(methoxymethoxy)methyl]-2-nitrothiophene as a yellowish oil, (4.32 g, 94%). $^1$H NMR (300 MHz, CDCl$_3$) δ ppm 3.36 (s, 3H), 4.20 (s, 2H), 4.34 (s, 2H), 4.62 (s, 2H), 7.13 (m, 3H), 7.21 (m,2H), 7.40 (s, 1H)

3-(Benzylthio)-4-[(methoxymethoxy)methyl]-2-nitrothiophene (4 g, 12.3 mmol) in dichloromethane (70 mL) and 1 N aqueous hydrochloric acid (35 mL) at 0° C. was reacted with chlorine gas bubbled in slowly over a period of 0.5 hour, then stirred for an additional 1 hour. The reaction mixture was purged with nitrogen gas to remove excess chlorine and treated with solid sodium bisulfite (11 g) added slowly to the mixture with stirring for 5 minutes. Dichloromethane (15 mL) and water (15 mL) were added, the organic layer was separated and eluted through 40 g of 50:50 mixture of MgSO$_4$/Na$_2$SO$_4$. The filtrate was concentrated under reduced pressure. A solution of the concentrate (4.7 g) in dichloromethane (100 mL) at −40° C. was bubbled with ammonia gas over a period of 10 minutes. The reaction mixture was stirred for an additional 15 minutes, purged with nitrogen gas to dispel the excess ammonia and concentrated under reduced pressure. The concentrate was purified by flash chromatography on silica gel using a Biotage-40s column eluting with 5:95 methanol/ dichloromethane to give 4-[(methoxymethoxy)methyl]-2-nitrothiophene-3-sulfonamide as an oil (2.3 g, 66%). $^1$H NMR (300 MHz, CDCl$_3$) δ ppm 3.31 (m, 3H), 4.70 (s, 2H), 4.73 (s, 2H), 7.85 (m, 2H), 7.88 (s, 1H).

4-[(Methoxymethoxy)methyl]-2-nitrothiophene-3-sulfonamide (1.8 g, 6.4 mmol) was reacted with iron powder (1.43 g, 4 equivalents) in acetic acid (70 mL) at 50° C. for 7.5 hours then concentrated under reduced pressure. A slurry of the residue in 5% methanol/dichloromethane (60 mL) and water (6 mL) was filtered through silica gel (20 g) and further rinsed with 5% methanol/dichloromethane (300 mL). The filtrate was concentrated under reduced pressure and the residue purified by flash chromatography on silica gel using a Biotage-12s column eluting with 2.5:97.5 methanol: dichloromethane to give 2-amino -4-[(methoxymethoxy)methyl]thiophene-3-sulfonamide (1 g, 62%). $^1$H NMR (300 MHz, DMSO-d$_6$) δ ppm 3.30 (s, 3H), 4.53 (s, 2H), 4.66 (s, 2H), 6.28 (s, 1H), 6.61 (s, 2H), 6.94 (s, 2H).

A solution of 3-[bis(methylthio)methylene]-1-[(cyclopropylmethyl)amino] quinoline -2,4(1H, 3H)-dione (500.3, 1.5 mmol) and the product of 2-amino-4-[(methoxy methoxy) methyl]thiophene-3-sulfonamide (377.62 mg, 1.5 mmol) in dioxane (15 mL) was stirred at reflux for 1.5 hours and concentrated under reduced pressure. The residue was purified by chromatography on silica gel eluting with 0% to 10% ethyl acetate/dichloromethane to give 1-[(cyclopropylmethyl)amino]-4-hydroxy-3-{7-[(methoxymethoxy)methyl]-1,1-dioxido-4H-thieno[2,3-e][1,2,4]thiadiazin-3-yl}quinolin -2(1H)-one (384.7 mg, 52%). $^1$H NMR (300 MHz, DMSO-d$_6$) δ 0.15 (m, 2H) 0.42 (m, 2H) 1.01 (m, 1H) 2.84 (d, J=6.99 Hz, 2H) 4.64 (s, 2H) 4.71 (s, 2H) 6.36 (br s, 1H) 7.42 (m, 2H) 7.86 (m, 1H) 8.07 (d, J=8.46 Hz, 1H) 8.16 (m, 1H)

To 1-[(cyclopropylmethyl)amino]-4-hydroxy-3-{7-[(methoxymethoxy)methyl]-1,1-dioxido-4H -thieno[2,3-e][1,2,4]thiadiazin-3-yl}quinolin-2(1H)-one (384.7 mg, 0.78 mmol) was added a solution of hydrogen chloride in dioxane (4N, 7.8 mL) at 0° C. The solution warmed to room temperature and stirred for 5.5 hours and concentrated under reduced pressure. This solid was suspended in dichloromethane (7.8 mL) and to the suspension was added 1,8-diazabicyclo[5.4.0]undec-7-ene (0.6 mL, 4.01 mmol) and diphenylphosphoryl azide (0.85 mL, 3.94 mmol) at room temperature and stirred overnight. The solution was concentrated in vacuo. The residue was purified by chromatography, eluting with 1% triethylamine/dichloromethane to give a triethylamine salt of 3-[7-(azidomethyl)-1,1-dioxido -4H-thieno[2,3-e][1,2,4]thiadiazin-3-yl]-1-[(cyclopropylmethyl)amino]-4-hydroxyquinolin-2(1H)-one (357 mg, 79%). MS (ESI$^-$) m/z 470 (M–H)$^-$. 1H NMR (300 MHz, DMSO-d$_6$) δ 0.22 (m, 2H) 0.46 (br d, J=7.35 Hz, 2H) 1.01 (m, 1H) 4.52 (s, 2H) 5.98 (t, J=6.62 Hz, 1H) 7.24 (s, 1H) 7.40 (m, 1H) 7.56 (m, 1H) 8.05 (m, 1H).

To the solution of 3-[7-(azidomethyl)-1,1-dioxido-4H-thieno[2,3-e][1,2,4]thiadiazin-3-yl]-1-[(cyclopropylmethyl) amino]-4-hydroxyquinolin-2(1H)-one (357 mg, 0.62 mmol) in pyridine (4.6 mL) and concentrated ammonium hydroxide (3 mL) was added triphenylphosphine (397 mg, 1.51 mmol) at room temperature. The solution was stirred at room temperature overnight and concentrated under reduced pressure. The residue was diluted with 30% hexane/toluene and the solid was filtered to give 3-[7-(aminomethyl)-1,1-dioxido-4H -thieno[2,3-e][1,2,4]thiadiazin-3-yl]-1-[(cyclopropylmethyl)amino]-4-hydroxyquinolin-2(1H)-one (250 mg, 90%). MS (ESI$^-$) m/z 446 (M+H)$^+$. $^1$H NMR (300 MHz, DMSO-d$_6$) δ 0.21 (m, 2H) 0.46 (br d, J=8.09 Hz, 2H) 1.00 (m, 1H) 4.12 (s, 2H) 5.98 (t, J=6.43 Hz, 1H) 7.12 (m, 1H) 7.22 (s, 1H) 7.58 (m, 1H) 772 (d, J=7.72 Hz, 1H) 8.04 (m, 1H).

To the suspension of the triethylamine salt of 3-[7-(aminomethyl)-1,1-dioxido-4H-thieno[2,3-e][1,2,4]thiadiazin-3-yl]-1-[(cyclopropylmethyl)amino]-4-hydroxyquinolin-2 (1H)-one (85.26 mg, 0.16 mmol) in N,N-dimethylformamide (1.6 mL) was added triethylamine (48 □L, 0.34 mmol) and then methanesulfonyl chloride (13.3 □L, 0.17 mmol) at room temperature. The solution was stirred at room temperature for 20 minutes and concentrated in vacuo. The residue purified by reverse phase chromatography, eluting with 20% to 95% acetonitrile/0.1% triflouroacetic acid in water to give N-[(3-{1-[(cyclopropylmethyl)amino]-4-hydroxy-2-oxo-1,2-dihydroquinolin-3-yl}-1,1-dioxido-4H-thieno[2,3-e][1,2,4]thiadiazin-7-yl)methyl]methanesulfonamide (compound II) (39.86 mg, 49%). MS (ESI$^+$) m/z 524 (M+H)$^+$. $^1$H NMR (300 MHz, DMSO-d$_6$) δ 0.15 (m, 2H) 0.42 (m, 2H) 1.01 (m, 1H) 2.84 (d, J=7.35 Hz, 2H) 2.99 (s, 3H) 4.29 (d, J=6.25 Hz, 2H) 6.37 (br s, 1H) 7.41 (m, 2H) 7.75 (t, J=6.25 Hz, 1H) 7.87 (m, 1H) 8.08 (d, J=8.09 Hz, 1H) 8.16 (m, 1H) 14.46 (m, 1H).

Example 5

Preparation of N-{3-[1-(Cyclobutylamino)-4-hydroxy-2-oxo-1,2-dihydro quinolin-3-yl]-1,1-dioxido-4H-1,2,4-benzothiadiazin-7-yl}methanesulfonamide (Compound III).

Compound III was prepared according to the procedure described in Example 432 of U.S. patent application Ser. No. 10/699,513, the entire content of which is incorporated herein by reference. The procedure is provided below:

A solution of 1-amino-4-hydroxyquinolin-2(1H)-one (0.516 g, 2.9 mmol) and cyclobutanone (1.05 g, 15.0 mmol) in acetic acid (0.90 g, 15.0 mmol) and methanol (20 mL) was treated portion wise with sodium cyanoborohydride (0.94 g, 15.0 mmol), stirred for 48 hours and concentrated. The residue was treated with 0.5 M aqueous sodium bicarbonate, acidified to pH 2 with 1 M hydrochloric acid and extracted with ethyl acetate. The ethyl acetate was washed with brine, dried over sodium sulfate, filtered and concentrated, The crude material was chromatographed on silica gel eluting with 3:2 hexane/ethyl acetate to give 1-(cyclobutylamino)-4-hydroxyquinolin-2(1H)-one (0.400 g, 60%). MS (ESI$^+$) m/z 231 (M+H)$^+$. $^1$H NMR (300 MHz, DMSO-$d_6$) δ 1.52 (m, 1H) 1.63 (m, 1H) 1.96 (m, 4H) 3.64 (m, 1H) 5.91 (s, 1H) 6.26 (d, J=6.62 Hz, 1H) 7.20 (t, J=8.09 Hz, 1H) 7.61 (m, 1H) 7.84 (m, 2H) 11.42 (s, 1H).

A solution of 1-(cyclobutylamino)-4-hydroxyquinolin-2 (1H)-one (0.115 g, 0.5 mmol) and tris(methylthio)methyl methyl sulfate (prepared using the procedures in SYNTHESIS, 22-25, 1988; M Barbero, S. Cadamuro, 1 Degani, R. Fochi, A. Gatti, V. Regondi) (0.27 g, 1.0 mmol) in pyridine (0.316 g, 4.0 mmol) and dioxane (5.0 mL) was heated at 60° C. for 30 minutes. Additional tris(methylthio)methyl methyl sulfate was added (0.27 g, 1.0 mmol) and heating continued for 30 minutes. The mixture was cooled to 25° C. and partitioned between ethyl acetate and water. The ethyl acetate layer was washed with water, brine, dried over sodium sulfate, filtered and concentrated. The crude material was chromatographed on silica gel eluting with 95/5 dichloromethane/ethyl acetate to give 3-[bis(methylthio)methylene]-1-(cyclobutylamino) quinoline-2,4(1H, 3H)-dione (0.146 g, 87% yield). MS (ESI$^+$) m/z 335 (M+H)$^+$. $^1$H NMR (300 MHz, DMSO-$d_6$) δ 1.54 (m, 1H) 1.66 (m, 1H) 1.99 (m, 4H) 2.61 (s, 6H) 3.62 (m, 1H) 6.18 (d, J=6.25 Hz, 1H) 7.15 (t, J=7.54 Hz, 1H) 7.63 (m, 1H) 7.72 (d, J=8.09 Hz, 1H) 7.98 (dd, J=7.91, 1.29 Hz, 1H).

A mixture of 2,5-diamino-benzenesulfonamide (0.288 g, 0.0015 mol, 1 eq.), dichloromethane (5 mL), and pyridine (5 mL) was stirred at 0° C. Methanesulfonyl chloride (119 μL, 0.0015 mol, 1 eq.) was added dropwise over 3 minutes. The reaction mixture was warmed to 25° and stirred for 18 hours. The reaction mixture was evaporated under reduced pressure and the residue was chromatographed on silica gel using a step gradient of 0-4% methanol in dichloromethane to yield 2-amino-5-[(methylsulfonyl)amino]benzenesulfonamide (68% yield). $^1$H NMR (300 MHz, DMSO-$d_6$) δ 2.87 (s, 3H) 3.39 (s, 1H) 5.80 (s, 1H) 6.78 (d, J=8.82 Hz, 1H) 7.13 (dd, J=8.64, 2.39 Hz, 1H) 7.29 (s, 2H) 7.45 (d, J=2.57 Hz, 1H) 9.21 (m, 1H), MS (ESI$^+$) m/z=266 (M+H)$^+$.

A mixture of 2-amino-5-[(methylsulfonyl)amino]benzenesulfonamide (0.195 g, 0.585 mmol, 1.5 eq.) and 3-[bis (methylthio)methylene]-1-(cyclobutylamino)quinoline-2,4 (1H, 3H)-dione (0.100 g, 0.390 mmol, 1.5 eq.) in anhydrous dioxane (10 mL) was heated for 1 hour at 120° C. After cooling to 25° C., the reaction mixture was treated with methanol (20 mL) and diethyl ether (20 mL) and the precipitated product collected by vacuum filtration to yield N-{3-[1-(cyclobutylamino)-4-hydroxy-2-oxo-1,2-dihydroquinolin-3-yl]-1,1-dioxido-4H-1,2,4-benzothiadiazin-7-yl}methane sulfonamide (compound III) (25 mg, 12% yield). $^1$H NMR (300 MHz, DMSO-$d_6$) δ 1.69 (m, 2H) 2.13 (m, 4H) 3.10 (s, 3H) 3.77 (m, 1H) 6.57 (s, 1H) 7.44 (t, J=7.35 Hz, 1H) 7.65 (m, 3H) 7.89 (t, J=7.35 Hz, 1H) 8.06 (d, J=8.46 Hz, 1H) 8.16 (d, J=7.72 Hz, 1H) 10.31 (s, 1H) 14.16 (s, 1H) 15.03 (s, 1H). MS (ESI$^+$) m/z=504 (M+H)$^+$.

Example 6

Comparison of Pharmacokinetic Profiles of Compounds I, II, and III

Compounds I, II and III were prepared as a solution in a DMSO: PEG-400 vehicle at a concentration of 5 mg/mL shortly before oral dosing.

Male Sprague-Dawley derived rats, weighing 250-350 grams, were obtained from Charles River Laboratories, Inc. (Wilmington, Mass.). The animals were fasted overnight prior to dosing and throughout the study period, but were allowed water ad libitum. Animals were allowed chow ad libitum post 12 hr.

Each study used a group of 3 rats. Each rat received a 5 mg/kg (1 mL/kg) oral dose of compound I, II or III administered by gavage. At selected time points after dosing, groups of three rats were euthanized with $CO_2$ and exsanguinated by cardiac puncture. The entire liver tissue from each animal was removed and placed in a labeled plastic container. Groups of rats were sacrificed 1, 12 and 24 hours after drug administration. The liver samples were stored on ice (about 4° C.), and then assayed for the concentration of each compound using high performance liquid chromatographic procedures, FIG. 1 and Table 1 show that 24 hours after oral dosing, the liver concentration of compound I is about 8-20 times higher than those of compounds II and III.

TABLE 1

Liver Concentrations of Compounds after a 5 mg/kg Oral Dose in Rats

| compound | Liver Concentration after Oral Dosing (μg/g) | | |
|---|---|---|---|
|  | 1 hour | 12 hours | 24 hours |
| I | 18.72 | 19.16 | 2.42 |
| II | 18.92 | 7.92 | 0.12 |
| III | 8.79 | 4.14 | 0.28 |

The 50% inhibitory concentration ($EC_{50}$) of compound I, when tested using HCV replicon assays, is about 2.5 nM. Therefore, the concentration of compound I in liver 24 hours after oral dosing is more than 1,800-fold higher than the compound's $EC_{50}$ value. In contrast, the $EC_{50}$ multiples of compounds II and III (i.e., the ratios of the post 24-hour liver concentrations of compound II or III over their respective $EC_{50}$ values) are significantly lower than that of compound I.

Example 7

Antiviral Activity of Combination of Compound I with VX-950

The effect of compound I on HCV replicon was evaluated alone or in combination with other anti-HCV agents. HCV 1b- N replicon cells were passaged in the presence of compound I, compound VX-950, interferon alpha (IFN), or combinations thereof, but in the absence of neomycin. In untreated control cells, the HCV RNA level was relatively stable over 2 months passage. Although the HCV RNA levels significantly reduced during treatment with any of the individual compounds or agents at concentrations 10 to 20-fold above their respective EC$_{50}$, none of them eliminated the HCV RNA from the replicon cells The EC50 values represent the 50% inhibitory concentrations of these compounds/agents in replicon cell assays.

The combination of IFN with either compound I or VX-950 appeared additive, but neither combination completely eliminated HCV RNA from replicon cells. However, the mechanisms of action of IFN in the treatment of HCV in vivo are complicated and may involve both direct and indirect antiviral effects, the latter of which is not assessed in the replicon cell assay.

In marked contrast, the combination of compounds I and VX-950 at concentrations 10 times above each respective EC$_{50}$ successfully reduced HCV RNA to undetectable levels. After passage 6, cells treated with this combination were treated with neomycin to select any colonies with replication of the replicon sufficient to confer the neomycin-resistant phenotype to the host cell. No colonies were observed, suggesting complete elimination of HCV replicon RNA from the cells.

To further assess the antiviral effect of the combination of compound I with other HCV inhibitors, each compound/agent alone and combinations from 4-fold to 1/8 of EC$_{50}$ were tested for inhibition of HCV using a checkerboard titration pattern (two-fold serial dilutions). Synergy, additivity and antagonism were evaluated using the Bliss independence model. Synergistic antiviral effect was observed at low concentrations of compounds I and VX-950. Additivity was observed at higher concentrations of either compound. The combination of I with IFN was additive at the majority of the concentrations and synergistic at low concentration combinations. These results suggest that a combination of I with another an-HCV compound acting on a different target in vivo can result in significantly enhanced antiviral activity.

The foregoing description of the present invention provides illustration and description, but is not intended to be exhaustive or to limit the invention to the precise one disclosed. Modifications and variations are possible in light of the above teachings or may be acquired from practice of the invention. Thus, it is noted that the scope of the invention is defined by the claims and their equivalents.

What is claimed is:

1. A process for preparation of a compound, a stereoisomer of the compound, a tautomer of the compound, or a pharmaceutically acceptable salt of the compound, stereoisomer, or tautomer, wherein:

the compound corresponds to formula (I):

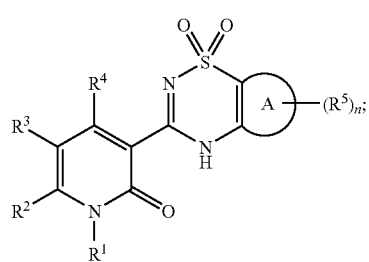

(I)

A is thienyl;

R$^1$ is cyclobutyl-N(R$_a$)—, wherein the cyclobutyl is optionally substituted with 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_e$), —SR$_c$, —S(O)R$_c$, —S(O)$_2$R$_c$, —OR$_c$, —N(R$_c$)(R$_e$), —C(O)R$_c$, —C(O)OR$_c$, and —C(O)NR$_c$R$_e$;

as to R$^2$ and R$^3$:

R$^2$ and R$^3$ are independently selected from the group consisting of hydrogen, alkenyl, alkynyl, alkoxyalkyl, alkoxycarbonyl, alkyl, aryl, arylalkyl, heteroaryl, heterocycle, heteroarylalkyl, cyano, halo, —N(R$_a$)(R$_b$), R$_a$R$_b$NC(O)—, —SR$_a$, —S(O)R$_a$, —S(O)$_2$R$_a$, and R$_a$C(O)—, wherein each such substituent is optionally substituted with 1, 2, or 3 substituents independently selected from the group consisting of R$_a$, alkyl, alkenyl, alkynyl, oxo, halo, cyano, nitro, haloalkyl, -(alkyl)(OR$_k$), -(alkyl)(NR$_a$R$_b$), —SR$_a$, —S(O)R$_a$, —S(O)$_2$R$_a$, —OR$_k$, —N(R$_a$)(R$_b$), —C(O)R$_a$, —C(O)OR$_a$, and —C(O)NR$_a$R$_b$, or, alternatively, R$^2$ and R$^3$, together with the carbon atoms to which they are attached, form a five- or six-membered ring selected from the group consisting of aryl, cycloalkyl, heteroaryl, and heterocycle, wherein each such substituent is optionally substituted with m independently selected R$^6$ substituents;

R$^4$ is selected from the group consisting of alkoxy, aryalkoxy, aryloxy, halo, hydroxy, R$_a$R$_b$N—, N$_3$—, and R$_e$S—, wherein each such substituent is optionally substituted with or 2 substituents independently selected from the group consisting of halo, nitro, cyano, —OH, —NH$_2$, and —COOH;

as to R$^5$:

at least one R$^5$ is R$_a$SO$_2$N(R$_f$)alkyl-, and each additional R$^5$ is independently selected from the group consisting of alkenyl, alkoxy, alkyl, alkynyl, aryl, arylalkyl, arylcarbonyl, aryloxy, azidoalkyl, formyl, halo, haloalkyl, halocarbonyl, heteroaryl, heteroarylalkyl, heterocycle, heterocyclealkyl, hydroxyalkyl, cycloalkyl, cyano, cyanoalkyl, nitro, R$_a$R$_b$N—, R$_a$C(O)—, R$_a$S—, R$_a$(O)S—, R$_a$(O)$_2$S—, R$_a$R$_b$-Nalkyl-, R$_a$(O)SN(R$_f$)—, R$_a$SO$_2$N(R$_f$)—, R$_a$(O)SN(R$_f$)alkyl-, R$_a$SO$_2$N(R$_f$)alkyl-, R$_a$R$_b$NSO$_2$N(R$_f$)—, R$_a$R$_b$NSO$_2$N(R$_f$)alkyl-, R$_a$R$_b$NC(O)—, R$_k$OC(O)—, R$_k$OC(O)alkyl-, R$_k$Oalkyl-, R$_a$R$_b$NSO$_2$—, R$_a$R$_b$NSO$_2$alkyl-, (R$_b$O)(R$_a$)P(O)O—, and —OR$_k$, wherein each such substituent is optionally substituted with 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$, and —C(O)NR$_c$R$_d$;

each R$_6$ is independently selected from the group consisting of alkyl, alkenyl, alkynyl, halo, cyano, nitro, haloalkyl, haloalkoxy, aryl, heteroaryl, heterocycle, arylalkyl, heteroarylalkyl, heterocyclealkyl, -(alkyl)(OR$_k$), -(alkyl)(NR$_a$R$_b$), —SR$_a$, —S(O)R$_a$, —S(O)$_2$R$_a$, —OR$_k$, —N(R$_a$)(R$_b$), —C(O)R$_a$, —C(O)OR$_a$, and —C(O)NR$_a$R$_b$, wherein each such substituent is optionally substituted with 1, 2, or 3 substituents independently selected from the group consisting of alkyl, alkenyl, alkynyl, oxo, halo, haloalkyl, cyano, nitro, —OR$_a$, —NR$_a$R$_b$, —SR$_a$, —SOR$_a$, —SO$_2$R$_a$, —C(O)R$_a$, —C(O)NR$_a$R$_b$, and —NC(O)R$_a$;

as to R$_a$ and R$_b$:

each R$_a$ and R$_b$ is independently selected from the group consisting of hydrogen, alkenyl, alkyl, alkylsulfanylalkyl, aryl, arylalkenyl, arylalkyl, cyanoalkyl, cycloalkenyl, cycloalkenylalkyl, cycloalkyl, cycloalkylalkyl, cycloalkylalkenyl, formylalkyl, haloalkyl, heteroaryl, heteroarylalkenyl, heteroarylalkyl, heterocycle, heterocyclealkenyl, heterocyclealkyl, hydroxyalkylcarbonyl, nitroalkyl, $R_cR_dN-$, $R_pO-$, $R_pO$alkyl-, $R_cR_dN$alkyl-, $R_cR_dNC(O)$alkyl-, $R_cSO_2-$, $R_cSO_2$alkyl-, $R_cC(O)-$, $R_cC(O)$alkyl-, $R_cOC(O)-$, $R_cOC(O)$alkyl-, $R_cR_d-N$alkylC(O)—, $R_cR_dNC(O)-$, $R_cR_dNC(O)O$alkyl-, and $R_cR_dNC(O)N(R_e)$alkyl-, wherein each such substituent is optionally substituted with 1 or 2 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), $—SR_c$, $—S(O)R_c$, $—S(O)_2R_c$, $—OR_c$, $—N(R_c)(R_d)$, $—C(O)R_c$, $—C(O)OR_c$, and $—C(O)NR_cR_d$, or alternatively, $R_a$ and $R_b$, together with the nitrogen atom to which they are attached, form a three- to six-membered ring selected from the group consisting of heteroaryl and heterocycle, wherein the heteroaryl and heterocycle are optionally substituted with 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), -alkylSO$_2$NR$_c$R$_d$, -alkylC(O)NR$_c$R$_d$, $—SR_c$, $—S(O)R_c$, $—S(O)_2R_c$, $—OR_c$, $—N(R_c)(R_d)$, $—C(O)R_c$, $—C(O)OR_c$, and $—C(O)NR_cR_d$; as to $R_c$ and $R_d$:

each $R_c$ and $R_d$ is independently selected from the group consisting of hydrogen, $—NR_fR_h$, $—OR_f$, $—CO(R_f)$, $—SR_f$, $—SOR_f$, $—SO_2R_f$, $—C(O)NR_fR_h$, $—SO_2NR_fR_h$, C(O)OR$_f$, alkenyl, alkyl, alkynyl, cycloalkyl, cycloalkylalkyl, cycloalkenyl, cycloalkenylalkyl, aryl, arylalkyl, haloalkyl, heteroaryl, heteroarylalkyl, heterocycle, and heterocycloalkyl, wherein each such substituent is optionally substituted with 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_f$), -(alkyl)($NR_fR_h$), $—SR_f$, $—S(O)R_f$, $—S(O)_2R_f$, $—OR_f$, $—N(R_f)(R_h)$, $—C(O)R_f$, $—C(O)OR_f$, $—C(O)NR_fR_h$, $—C(O)N(H)NR_fR_h$, $—N(R_e)C(O)OR_f$, $—N(R_e)SO_2NR_fR_h$, $—N(R_e)C(O)NR_fR_h$, -alkylN(R$_e$)C(O)OR$_f$, -alkylN(R$_e$)SO$_2$NR$_f$R$_h$, and -alkylN(R$_e$)C(O)NR$_f$R$_h$, or alternatively, $R_c$ and $R_d$, together with the nitrogen atom to which they are attached, form a three-to six-membered ring selected from the group consisting of heteroaryl and heterocycle, wherein the heteroaryl and heterocycle are optionally substituted with 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_f$), -(alkyl(NR$_f$R$_h$), $—SR_f$, $—S(O)R_f$, $—S(O)_2R_f$, $—OR_f$, $—N(R_f)(R_h)$, $—C(O)R_f$, $—C(O)OR_f$, and $—C(O)NR_fR_h$;

each $R_c$ is independently selected from the group consisting of hydrogen, alkenyl, alkyl, and cycloalkyl;

as to $R_f$ and $R_h$:

each $R_f$ and $R_h$ is independently selected from the group consisting of hydrogen, alkyl, alkenyl, aryl, arylalkyl, cycloalkyl, cycloalkylalkyl, cycloalkenyl, cycloalkenylalkyl, heterocycle, heterocyclealkyl, heteroaryl, and heteroarylalkyl, wherein each such substituent is optionally substituted with 1, 2, or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —NH$_2$, —N(H)(alkyl), —N(alkyl)$_2$, —S(alkyl), —S(O)(alkyl), —SO$_2$alkyl, -alkyl-OH, -alkyl-O-alkyl, -alkylNH$_2$, -alkylN(H)(alkyl), -alkylN(alkyl)$_2$, -alkylS(alkyl), -alkylS(O)(alkyl), -alkylSO$_2$alkyl, —N(H)C(O)NH$_2$, —C(O)OH, —C(O)O(alkyl), —C(O)alkyl, —C(O)NH$_2$, —C(O)NH$_2$, —C(O)N(H)(alkyl), and —C(O)N(alkyl)$_2$, or alternatively, $R_f$ and $R_h$, together with the nitrogen atom to which they are attached, form a three- to seven-membered ring selected from the group consisting of heterocycle and heteroaryl, wherein the heterocycle and heteroaryl are optionally substituted with 1, 2, or 3 substituents independently selected from the group consisting of alkyl, alkenyl, alkynyl, cyano, halo, oxo, nitro, aryl, arylalkyl, cycloalkyl, cycloalkenyl, heterocycle, heteroaryl, heteroarylalkyl, —OH, —O(alkyl), —NH$_2$, —N(H)(alkyl), —N(alkyl)$_2$, —S(alkyl), —S(alkyl), —S(O)(alkyl), -alkyl—OH, -alkyl-O-alkyl, -alkylNH$_2$, -alkylN(H)(alkyl), -alkylS(alkyl), alkylS(O)(alkyl), -alkylSO$_2$alkyl, -alkylN(alkyl)$_2$, —N(H)C(O)NH$_2$, —C(O)OH, —C(O)O(alkyl), —C(O)alkyl, —C(O)NH$_2$, —C(O)NH$_2$, —C(O)N(H)(alkyl), and —C(O)N(alkyl)$_2$;

each $R_k$ is independently selected from the group consisting of hydrogen, alkenyl, alkyl, aryl, arylalkyl, cyanoalkyl, cycloalkenyl, cycloalkenylalkyl, cycloalkyl, cycloalkylalkyl, formylalkyl, haloalkyl, heteroaryl, heteroarylalkyl, heterocycle, heterocyclealkyl, nitroalkyl, $R_aR_b$Nalkyl-, $R_a$Oalkyl-, $R_aR_b$NC(O)—, $R_aR_b$NC(O)alkyl, $R_aS-$, $R_aS(O)-$, $R_aSO_2-$, $R_a$Salkyl-, $R_a(O)$Salkyl-, $R_aSO_2$alkyl-, $R_aOC(O)-$, $R_aOC(O)$alkyl-, $R_aC(O)-$, and $R_aC(O)$alkyl-, wherein each such substituent is optionally substituted with 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)($OR_c$), -(alkyl)($NR_cR_d$), $—SR_c$, $—S(O)R_c$, $—S(O)_2R_c$, $—OR_c$, $—N(R_c)(R_d)$, $—C(O)R_c$, $—C(O)OR_c$, and $—C(O)NR_cR_d$;

each $R_p$ is independently selected from the group consisting of hydrogen, alkenyl, alkyl, aryl, arylalkyl, cyanoalkyl, cycloalkenyl, cycloalkenylalkyl, cycloalkyl, cycloalkylalkyl, formylalkyl, haloalkyl, heteroaryl, heteroarylalkyl, heterocycle, heterocyclealkyl, and nitroalkyl, wherein each such substituent is optionally substituted with 1, 2, or 3 substituents independently selected from the group consisting of alkyl, alkenyl, alkynyl, oxo, halo, cyano, nitro, haloalkyl, haloalkoxy, aryl, heteroaryl, heterocycle, arylalkyl, heteroarylalkyl, alkoxyalkoxyalkyl, -(alkyl)(OR$_c$), -(alkyl)(NR$_c$R$_d$), —SR$_c$, —S(O)R$_c$, —S(O)$_2$R$_c$, —OR$_c$, —N(R$_c$)(R$_d$), —C(O)R$_c$, —C(O)OR$_c$, and —C(O)NR$_c$R$_d$;

m is 1, 2, 3, or 4;

n is 1, 2, 3, or 4; and the process comprises:

(a) contacting a compound of formula (26)

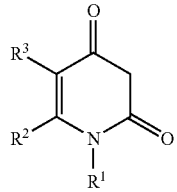
(26)

with a reagent selected from the group consisting of (1) carbon disulfide and a methylating agent, (2) tris(methylthio)methyl methyl sulfate, and (3) tris(methylthio)methyl methyl tetrafluoroborate, in the presence of a base, to provide a compound of formula (27)

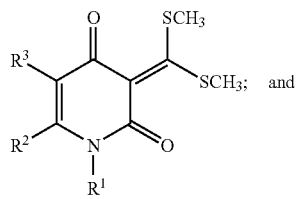
(27)

(b) contacting the compound of formula (27) with a compound of formula (13)

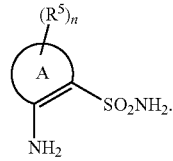
(13)

2. The process of claim 1, wherein the compound of formula (13) is 2-amino-4-(methane-sulfonylamino-methyl)-thiophene-3-sulfonic acid amide:

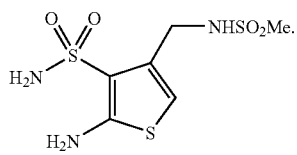
(13A)

* * * * *